(12) United States Patent
Khu et al.

(10) Patent No.: US 8,664,473 B2
(45) Date of Patent: Mar. 4, 2014

(54) METHODS AND COMPOSITIONS FOR PRODUCING ALUMINUM TOLERANT ALFALFA

(75) Inventors: Dong-Man Khu, Ardmore, OK (US); Rafael Reyno, Tawarembo (UY); E. Charles Bummer, Ardmore, OK (US); Joseph H. Bouton, Athens, GA (US); Maria J. Monteros, Ardmore, OK (US)

(73) Assignee: The Samuel Roberts Noble Foundation, Inc., Ardmore, OK (US)

( * ) Notice: Subject to any disclaimer, the term of this patent is extended or adjusted under 35 U.S.C. 154(b) by 343 days.

(21) Appl. No.: 12/987,796

(22) Filed: Jan. 10, 2011

(65) Prior Publication Data

US 2011/0203011 A1    Aug. 18, 2011

Related U.S. Application Data

(60) Provisional application No. 61/293,652, filed on Jan. 9, 2010.

(51) Int. Cl.
*A01H 1/02* (2006.01)
*C07K 14/415* (2006.01)
*A01H 5/00* (2006.01)
*A01H 5/10* (2006.01)
*A01H 5/08* (2006.01)

(52) U.S. Cl.
USPC ........... 800/267; 800/266; 800/278; 800/295; 800/268; 435/6.11; 435/430.1

(58) Field of Classification Search
None
See application file for complete search history.

(56) References Cited

PUBLICATIONS

Narasimhamoorthy et al. (Theor Appl Genet (2007) 114:901-913).*
Atanassov et al. (Plant Cell Tissue Organ Culture 3:149-162 (1984)).*
Gupta et al. (Current Science, vol. 80, (2001), pp. 524-535).*
Meksem et al. (Mol. Genet. Genomics, (2001), pp. 207-214).*
Sledge et al. (Theor. Appl. Genet. (2005), pp. 980-992).*
Collard et al. (Euphytica (2005), pp. 169-196).*
Song et al. (PNAS (1995), pp. 7719-7723).*
Luo et al. (PNAS (2004), pp. 7040-7045).*
Frisch et al. (Genetics (2005), pp. 909-917).*
Agarwal et al. (Plant Cell Report (2008), pp. 617-631).*
Khu et al., "QTL mappig of aluminum tolerance in tetraploid alfalfa," Joint Meeting of the 41$^{st}$ North American Alfalfa Improvement Conference & 20$^{th}$ Trifolium Conference, Dallas, Texas, Jun. 2, 2008 (Abstract).

* cited by examiner

*Primary Examiner* — David T Fox
*Assistant Examiner* — Jared Shapiro
(74) *Attorney, Agent, or Firm* — Dentons US LLP

(57) ABSTRACT

The invention relates to alfalfa plants and lines having aluminum tolerance. The invention also relates to parts of alfalfa plants from lines having aluminum tolerance, including seeds capable of growing aluminum tolerant alfalfa plants. Methods for the use and breeding of aluminum tolerant alfalfa plants are also provided.

22 Claims, 27 Drawing Sheets

ALtet4  LG 3

Altet-4  LG 4

95-608 LG1

95-608- LG-2

95-608 LG 3

95-608   LG4

95-608   LG 5

95-608   LG 6

95-608   LG 7

95-608   LG 8

METHODS AND COMPOSITIONS FOR PRODUCING ALUMINUM TOLERANT ALFALFA

This application claims the priority of U.S. Provisional Application No. 61/293,652, filed Jan. 9, 2010, the entire disclosure of which is incorporated herein by reference.

FIELD OF THE INVENTION

The invention relates to methods and compositions for producing alfalfa plants that tolerate the presence of aluminum in soil.

BACKGROUND OF THE INVENTION

Alfalfa (*Medicago sativa* subsp. *sativa*) is the most important forage legume in the United States. Alfalfa is tetraploid, having 4 homoeologous chromosomes for each of the 8 different chromosomes, for a total of 32 chromosomes. It is highly desirable for hay production and pasture for livestock because it produces more protein per hectare than grain or oilseed crops, and requires little or no nitrogen fertilizer because of its ability to carry out symbiotic nitrogen fixation. However, alfalfa is very sensitive to aluminum toxicity.

Aluminum toxicity causes similar symptoms in many plant species. Micromolar concentrations of $Al^{+3}$ can damage the root system, sometimes within minutes of exposure. Damage to the root system then significantly reduces yields due to an insufficient intake of water and other nutrients (Kochian, 1995; Kochian et al., 2004). Heavy applications of limestone and P fertilizer are commonly used to prevent yield loss, but these amendments are often not economical or practical.

SUMMARY OF THE INVENTION

In a first aspect, there is provided a method for producing an aluminum tolerant alfalfa line comprising introgressing at least one chromosomal locus from a more aluminum tolerant alfalfa plant into a less aluminum tolerant alfalfa line. For example, a tolerant alfalfa plant may display a reduction in one or more symptoms of aluminum toxicity relative to a control plant when the plant is in contact with aluminum (e.g., a 10%, 25%, 50%, 75% or 90% reduction). Symptoms of aluminum toxicity that may be reduced in resistant plants include, but are not limited to, reduction or inhibition of root growth, increase in susceptibility to drought, nutrient deficiency, decreased yield, and leaf chlorosis and/or necrosis. In certain embodiments, the chromosomal locus from the more aluminum tolerant alfalfa plant maps between markers 6-MITC343-140 and 6-3d03.atc.5-1-244 on linkage group 6 or between loci 2-AW310-353 and 1-AW11-214 on linkage group 2 (e.g., on linkage group 6 between 60.3 and 68.7 cM or on linkage group 2 between 46.4 and 65.3 cM). For example, the chromosomal locus may be linked to a marker selected from the group consisting of 6-MITC343-140 and 6-3d03.atc.5-1-244 on linkage group 6 or between loci 2-AW310-353 and 1-AW11-214 on linkage group 2. In some aspects the chromosomal locus may be linked to 6-MTIC343-143 on linkage group 6. In other aspects, the chromosomal locus may be between loci 2-AW310-333 and 2-AW310-351 on linkage group 2. In still other aspects, the chromosomal locus may be linked to u-BG218-295 on linkage group 2.

In some aspects, a method according to the invention comprises: (a) crossing a plant within the *Medicago* genus having aluminum tolerance with a *Medicago sativa* plant lacking aluminum tolerance to form a first population (b) selecting one or more members of said population having aluminum tolerance; and (c) backcrossing progeny obtained to plants of a *Medicago sativa* variety otherwise lacking the aluminum tolerance to obtain an introgressed variety comprising aluminum tolerance. In certain embodiments, steps (b) and (c) may be repeated until an aluminum tolerance trait has been introgressed into the genetic background of a plant line that initially lacked aluminum tolerance such that the introgressed plant comprises less than about 50%, 25%, 10%, 5% or 1% genomic material from the initial aluminum tolerant plant. In some embodiments, the initial cross of step (a) further comprises using embryo rescue to form said first population. In certain embodiments, the steps are repeated about 1, 2, 3, 4, 5, 6 or more times.

In certain aspects, a less aluminum tolerant alfalfa line is an agronomically elite line. For example, the less aluminum tolerant alfalfa line may be a commercial *Medicago sativa* line, such as a line that is used to produce alfalfa hay or silage. The less aluminum tolerant alfalfa line may be a hybrid or inbred line. In certain specific embodiments, the less aluminum tolerant alfalfa line is any commercial variety that is well known to one skilled in the art.

In some aspects, the more aluminum tolerant plant is another member of the *Medicago* genus, other than *Medicago sativa* L., such as *Medicago truncatula* or *Medicago trifolium*. The plant may be a wild plant, or a hybrid or inbred line. In certain embodiments, the more aluminum tolerant alfalfa plant is *Medicago sativa* subs. *caerulea* accession PI464724-25. In certain other embodiments the more aluminum tolerant alfalfa plant is a plant other than *Medicago sativa* subs. *caerulea* accession PI464724-25.

In a further aspect, there is provided a method for introgressing aluminum tolerance into an alfalfa line by marker-assisted selection using a marker linked to a chromosomal locus from an aluminum tolerant alfalfa plant. In certain embodiments, the marker may be a marker that detects chromosomal insertions, deletions or other polymorphisms, such as simple sequence repeats and single nucleotide polymorphisms (SNPs). In certain embodiments, a marker for use according to the invention is between markers 6-MITC343-140 and 6-3d03.atc.5-1-244 on linkage group 6 or between loci 2-AW310-353 and 1-AW11-214 on linkage group 2, inclusive. For example, the marker may be the 6-MTIC343-14, 6-MITC343-140, 6-3d03.atc.5-1-244, 2-AW310-353, 2-AW310-333, 2-AW310-351, u-BG218-295 or 1-AW11-214 marker.

In still a further aspect, there is provided an alfalfa line produced by methods according to the invention, wherein the line comprises aluminum tolerance and is agronomically elite. Progeny of such plants comprising aluminum tolerance and an agronomically elite phenotype are also included as part of the invention.

In yet a further aspect, the invention provides an alfalfa plant comprising aluminum tolerance wherein the plant is agronomically elite. For example, the alfalfa plant may be an inbred or hybrid plant. A tolerant alfalfa plant may display a reduction in one or more symptom of aluminum toxicity. Symptoms that may be reduced in a tolerant plant include, but are not limited to, reduction or inhibition of root growth, increase in susceptibility to drought, nutrient deficiency, decreased yield, and leaf chlorosis and/or necrosis. Progeny of such plants comprising aluminum tolerance and an agronomically elite phenotype are also included as part of the invention. Likewise, seeds of plants according to the invention are also provided wherein the seeds produce agronomically elite plants comprising aluminum tolerance. Transgenic alfalfa plants are also provided as part of the instant invention.

In certain embodiments, the invention provides parts of a plant according to the invention. Plant parts included but are not limited to a leaf, an ovule, pollen or a cell.

In a further aspect, a plant according to the invention comprises at least one chromosomal locus mapping between 6-MITC343-140 and 6-3d03.atc.5-1-244 on linkage group 6 or between loci 2-AW310-353 and 1-AW11-214 on linkage group 2 from an aluminum tolerant parent plant. For example, the chromosomal locus may be linked to a marker selected from the group consisting of 6-MITC343-140 and 6-3d03.atc.5-1-244 on linkage group 6 or between loci 2-AW310-353 and 1-AW11-214 on linkage group 2. In some aspects the chromosomal locus may be linked to 6-MTIC343-143 on linkage group 6. In other aspects, the chromosomal locus may be between loci 2-AW310-333 and 2-AW310-351 on linkage group 2. In still other aspects, the chromosomal locus may be linked to u-BG218-295 on linkage group 2.

Plants according to the invention may be homozygous or heterozygous for a chromosomal locus linked to an aluminum tolerance phenotype. In further embodiments, the invention provides a seed of a plant according to the invention wherein the seed comprises a chromosomal locus linked to aluminum tolerance.

In still a further aspect, an alfalfa plant according to the instant invention comprises at least one additional trait of agronomic interest.

In yet another aspect, a tissue culture of regenerable cells of an alfalfa plant according to the invention is provided. The tissue culture may be capable of regenerating alfalfa plants capable of expressing all of the physiological and morphological characteristics of the starting plant (e.g., aluminum tolerance), and of regenerating plants having substantially the same genotype as the starting plant. The regenerable cells in such tissue cultures may be derived, for example, from embryos, meristems, cotyledons, pollen, leaves, anthers, roots, root tips, pistil, flower, seed or stalks. In still further embodiments, the invention provides alfalfa plants regenerated from a tissue culture of the invention wherein the plants comprise aluminum tolerance.

In a further aspect, the present invention provides a method of producing progeny of a plant according to the invention, the method comprising the steps of: (a) preparing a progeny plant derived from an aluminum tolerant plant, wherein said preparing comprises crossing a plant according to the invention with a second plant; and (b) crossing the progeny plant with itself or a second plant to produce a seed of a progeny plant of a subsequent generation. In further embodiments, the method may additionally comprise: (c) growing a progeny plant of a subsequent generation from said seed of a progeny plant of a subsequent generation and crossing the progeny plant of a subsequent generation with itself or a second plant; and repeating the steps for an additional 3-10 generations to produce further progeny plants. The derived plant may be an inbred line, and the aforementioned repeated crossing steps may be defined as comprising sufficient inbreeding to produce the inbred line. In the method, it may be desirable to select particular plants resulting from step (c) for continued crossing according to steps (b) and (c). By selecting plants having one or more desirable traits, an aluminum tolerant plant is obtained which possesses some of the desirable traits of the line/hybrid as well as potentially other selected traits.

In still a further aspect there is provided a method of vegetatively propagating an alfalfa plant according to the invention comprising the steps of: (a) collecting tissue capable of being propagated from a plant according to the invention; (b) cultivating said tissue to obtain proliferated shoots; (c) rooting said proliferated shoots to obtain rooted plantlets; and, optionally, (d) growing plants from the rooted plantlets.

In certain aspects, the present invention provides a method of producing food or feed comprising: (a) obtaining a plant according to the invention, wherein the plant has been cultivated to maturity, and (b) collecting plant tissue from the plant. Plants according to the invention comprise, in certain aspects, a commercial alfalfa variety comprising aluminum tolerance. Accordingly, alfalfa produced from such plants may be of any variety.

In further aspects, the invention provides a method of making a commercial product comprising obtaining alfalfa according the invention and producing a commercial product therefrom.

Embodiments discussed in the context of methods and/or compositions of the invention may be employed with respect to any other method or composition described herein. Thus, an embodiment pertaining to one method or composition may be applied to other methods and compositions of the invention as well.

As used herein the terms "encode" or "encoding" with reference to a nucleic acid are used to make the invention readily understandable by the skilled artisan, however these terms may be used interchangeably with "comprise" or "comprising" respectively.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Figure 1:
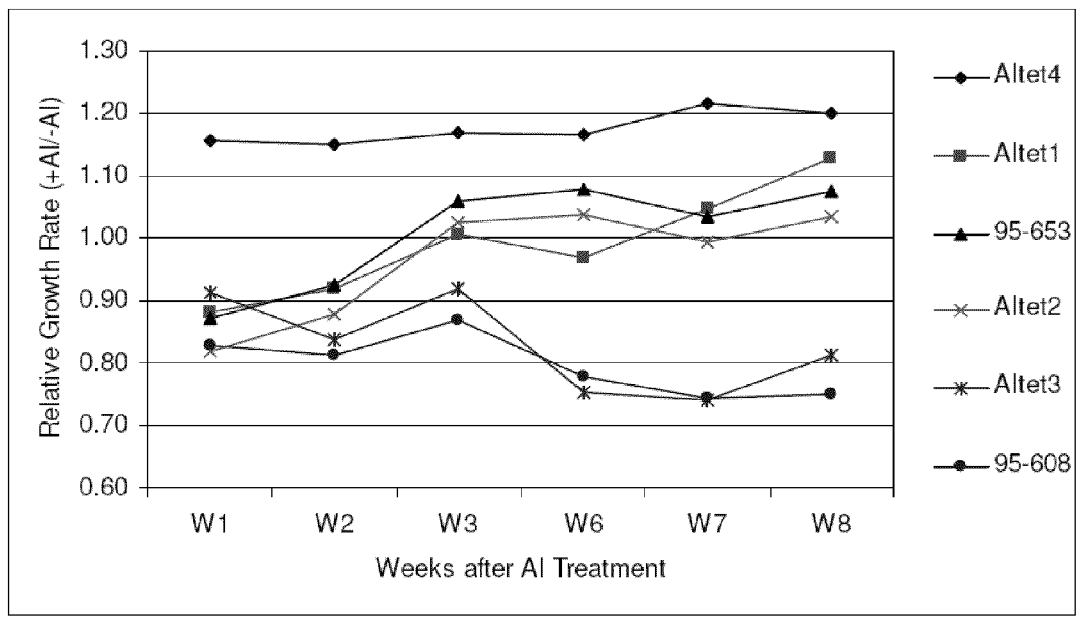
FIG. 1: Callus relative growth ratio (callus growth in medium with aluminum/callus growth in medium without aluminum) of six genotypes grown in Blaydes callus induction medium with and without aluminum.

The invention provides alfalfa exhibiting tolerance to aluminum. Such plants can be referred to as aluminum tolerant alfalfa varieties. Methods of producing aluminum tolerant alfalfa plants are also provided. Also disclosed herein are methods of use and derivatives of the aluminum tolerant alfalfa plants.

The aluminum tolerant *Medicago sativa* alfalfa plants of the invention may bear one or more alleles conferring aluminum tolerance that have been introduced from other members of the *Medicago* genus employing techniques described herein. According to the invention, such traits may be introduced, for the first time, into agronomically elite varieties. The resulting aluminum tolerant alfalfa plants of the present invention may thus display vigorous growth and other desirable properties for cultivation.

The invention also provides methods for introgression of aluminum tolerance into an alfalfa line. Through multiple rounds of backcrossing, chromosomal loci linked to aluminum tolerance may be introgressed into any other genotype according to the invention. This allows production of agronomically elite plants with aluminum tolerance. The backcrossing allows recovery of a starting genotype together with the desired aluminum tolerance alleles. For example, aluminum tolerant lines may comprise a genome that is 80%, 85%, 90%, 95%, 98% or more *Medicago sativa* L. sequence from any particular background. Aluminum tolerant plants according to the invention may be defined, in certain embodiments, as "locus converted plants," wherein essentially all of the desired morphological and physiological characteristics of a variety are recovered in addition to the characteristics of the single locus transferred into the variety via a backcrossing or by genetic transformation. Such lines may be heterozygous for chromosomal loci linked to aluminum tolerance or may be homozygous for such loci. Homozygous lines may have particular use, for example, as parents for selfing to produce inbred seed or crossing with a second elite alfalfa line for generating hybrid alfalfa seed.

Introgression of aluminum tolerance in accordance with the invention may be effected by marker assisted selection. In particular, the invention provides genetic markers genetically linked to alleles conferring aluminum tolerance. Thus, tracking of markers linked to these loci allows efficient identification of progeny plants harboring aluminum tolerance. High-throughput breeding techniques using marker assisted selection can be used to rapidly introgress loci into an agronomically elite background and thereby produce commercially viable aluminum tolerant lines.

As used herein, an "agronomically elite" alfalfa plant or line refers to plants or varieties exhibiting traits appropriate for commercial production, which are well known to those of skill in the art. For example, agronomically elite plants are capable of producing a commercial scale hay or silage yield. In certain aspects, agronomically elite plants and lines produce alfalfa of uniform size, color and quality. Agronomically elite lines may also exhibit desirable hardiness traits, such as disease resistance, cold tolerance, environmental stress tolerance, persistence, forage quality and nutrient utilization or use traits such as improved harvestability.

As used herein, a "control alfalfa plant" is any alfalfa plant susceptible to aluminum (aluminum susceptible), including typical commercially available and wild relatives of modern alfalfa plants. A control alfalfa plant is also grown under similar environmental conditions to a test plant according to the present disclosure.

As used herein, a "hybrid alfalfa plant" includes a plant resulting directly or indirectly from crosses between populations, breeds or cultivars within the species *Medicago sativa*. This also refers to plants resulting directly or indirectly from crosses between different species within the *Medicago* genus (e.g., interspecific hybrids resulting from crosses between *Medicago sativa* and *Medicago truncatula* or crosses between *Medicago sativa* and *Medicago trifolium*).

As used herein an "aluminum tolerant alfalfa plant" displays an increased tolerance to aluminum, or a decrease in the development of symptoms of aluminum susceptibility, when compared to the parental *Medicago sativa* plant or a control alfalfa line grown under similar environmental conditions.

As used herein, a descendent or progeny of a particular plant includes not only, without limitation, the products of any initial cross (be it a backcross or otherwise) between two plants, but all descendants whose pedigree traces back to the original cross. In an aspect of the present invention, the descendent contains about 50%, 25%, 12.5%, 6%, 3%, 1% or less nuclear DNA from an aluminum tolerant alfalfa plant and expresses that genetic material to provide at least a portion of the plant's aluminum tolerance.

Aluminum tolerant alfalfa plants also include alfalfa cultivars, lines or varieties having tolerance to aluminum, referred to herein as aluminum tolerant alfalfa cultivars, aluminum tolerant alfalfa lines, or aluminum tolerant alfalfa varieties respectively. Aluminum tolerant alfalfa cultivars, aluminum tolerant alfalfa lines, or aluminum tolerant alfalfa varieties may have been bred and selected for at least aluminum tolerance and may also have been selected for other desirable traits.

As used herein, a "female parent" refers to an alfalfa plant that is the recipient of pollen from a male donor line, which successfully pollinates an egg. A female parent can be any alfalfa plant that is the recipient of pollen. Such female parents can be male sterile, for example, because of genetic male sterility, cytoplasmic male sterility, or because they have been subject to emasculation of the stamens. Genetic or cytoplasmic male sterility can be manifested in different manners, such as sterile pollen, malformed or stamenless flowers, positional sterility, and functional sterility.

As used herein, "cytoplasmic male sterility" refers to plants that are not usually capable of breeding from self-pollination, but are capable of breeding from cross-pollination.

As used herein, "linkage" or "genetic linkage" is a phenomenon wherein alleles on the same chromosome tend to segregate together more often than expected by chance if their transmission was independent.

As used herein, a "marker" is an indicator for the presence of at least one phenotype, genotype, or polymorphism. Markers include, but are not limited to, single nucleotide polymorphisms (SNPs), cleavable amplified polymorphic sequences (CAPS), amplified fragment length polymorphisms (AFLPs), restriction fragment length polymorphisms (RFLPs), simple sequence repeats (SSRs), simple sequence length polymorphisms (SSLPs), insertion(s)/deletion(s) (IN-DEL(s)), and random amplified polymorphic DNA (RAPD) sequences. A marker may be codominant and completely heritable (both alleles at a locus in a diploid heterozygote are readily detectable), with no environmental variance component, i.e., heritability of 1. A "nucleic acid marker" as used herein means a nucleic acid molecule that is capable of being a marker for detecting a polymorphism, phenotype, or both associated with aluminum tolerance. A "molecular marker" as used herein means a nucleic acid molecule that is capable of being a marker for detecting a polymorphism, phenotype, or both associated with aluminum tolerance. Genetic maps and markers for use in alfalfa are known in the art (Brummer et al., 1993; Echt et al., 1993; Kiss et al., 1993; Brower et al., 2000; Robins et al., 2008; Robins et al., 2007).

As used herein, a "desirable trait" or "desirable traits" that may be introduced into aluminum tolerant alfalfa plants by breeding may be directed to the alfalfa plant. Desirable alfalfa plant traits that may be independently selected include, but are not limited to, plant vigor, leaf shape, leaf length, leaf color, plant height, time to maturity, adaptation to field growth, persistance, forage quality, and resistance to one or more diseases or disease causing organisms. Any combination of desirable alfalfa traits may be combined with aluminum tolerance.

The present invention provides for one or more aluminum tolerant alfalfa plants. The aluminum tolerance of any alfalfa plant provided herein can be a tolerance to high concentrations of aluminum or a tolerance to low concentrations of aluminum, wherein either the high or low concentration of aluminum would cause symptoms in a non-aluminum-tolerant alfalfa plant. The aluminum tolerance of an alfalfa plant provided herein can be measured by any means available in the art.

In one aspect, the aluminum tolerance of an alfalfa plant is determined using a callus or tissue culture assay. The assay may comprise inducing callus formation, transferring one part of the induced callus to a growth medium comprising aluminum, and a second part of the callus to a growth medium which does not comprise aluminum. The growth medium may be Blaydes callus induction medium, and the callus may be grown in controlled growth chambers at 25° C. and with an 18-hour light photoperiod. The assay may further comprise weighing the callus. The assay may further comprise comparing the relative weights or amount of growth between the two parts of the callus.

In another aspect, the aluminum tolerance of an alfalfa plant is determined using a whole-plant culture media assay. The assay may comprise growing vegetatively propagated alfalfa clones or stem cuttings in culture media comprising 400 µM $CaCl_2$, 1.4% gel rite, 0 or 50 µM $Al^{+3}$ in the form of $AlCl_3$, and pH 7.0 or 4.0 adjusted using 1 N HCl, and the alfalfa may be grown in controlled-environment growth chambers at 25° C. with an 18-hour light photoperiod.

Root growth may be quantified using winRHIZO software (Regent Instruments, Québec, Canada) to determine aluminum tolerance. For example, total root length, lateral root numbers and branching may be quantified. The absolute root growth and ratio of root characteristics (biomass, length and branching) after 3 weeks of growth in either aluminum-containing media or aluminum-free media may also be used for determining aluminum tolerance.

In another aspect, the alfalfa plants and lines provided herein demonstrate little or no aluminum toxicity symptoms after treatment with aluminum. In some aspects, an aluminum tolerant alfalfa genotype demonstrates aluminum toxicity symptoms in less than 10%, 9%, 8%, 7%, 6%, 5%, 4%, 3% 2%, or 1% of alfalfa plants of that genotype.

Aluminum tolerant alfalfa plants may exhibit a delay in the onset of aluminum toxicity symptoms relative to a non-tolerant control alfalfa plant. In some embodiments, the aluminum tolerant alfalfa plants exhibit a delay of 1, 2, 3, 4, 5, 6, 7, 8, 9, 10, 11, 12, 13, 14, or more days in the onset of aluminum toxicity symptoms relative to a control alfalfa plant. In other embodiments, the aluminum tolerant alfalfa plants exhibit a delay of at least 7 or more days, 10 or more days, or 14 or more days in the onset of aluminum toxicity symptoms relative to a control alfalfa plant.

In one aspect, the alfalfa plant is a seedling at the time of aluminum exposure. In some aspects, the alfalfa plant is a seedling at the trifoliate leaf stage of development at the time of aluminum exposure. In one aspect, aluminum toxicity symptoms can be measured at any time after aluminum exposure of an alfalfa plant. In other aspects, symptoms can be measured 2, 3, 4, 5, 6, 7, 8, 9, 10, 11, 12, 13, 14, 15, 16, 17, 18, 19, 20, 21, or more days after exposure. In another aspect, the alfalfa plant is any age of plant at the time of exposure.

In another aspect, the alfalfa plant is a callus at the time of aluminum exposure. In some aspects, the callus has been allowed to form for about two weeks in Blaydes callus induction medium before exposure. In one aspect, aluminum toxicity symptoms can be measured at any time after aluminum exposure of an alfalfa callus. In other aspects, symptoms can be measured 2, 3, 4, 5, 6, 7, 8, 9, 10, 11, 12, 13, 14, 15, 16, 17, 18, 19, 20, 21, or more weeks after exposure. In another aspect, the alfalfa callus is any age of callus at the time of exposure.

In another aspect, the alfalfa plant is a vegetatively propagated alfalfa clone or stem cutting at the time of aluminum exposure. In some aspects, the vegetatively propagated alfalfa clone or stem cutting has been allowed to develop in medium comprising 400 µM $CaCl_2$, 1.4% gel rite, 0 or 50 µM $Al^{+3}$ in the form of $AlCl_3$ before exposure. In one aspect, aluminum toxicity symptoms can be measured at any time after aluminum exposure of an alfalfa plant. In other aspects, symptoms can be measured 2, 3, 4, 5, 6, 7, 8, 9, 10, 11, 12, 13, 14, 15, 16, 17, 18, 19, 20, 21, or more days after exposure. In another aspect, the alfalfa plant is any age of plant at the time of exposure.

Aluminum tolerant alfalfa plants of the present invention may exhibit an increase in callus relative growth ratios after exposure to aluminum when compared to the relative growth rate of a control alfalfa callus exposed to aluminum. In one aspect, the aluminum tolerant alfalfa callus exhibit a 1%, 2%, 5%, 10%, 15%, 20% or more increase in callus relative growth ratio relative to a control alfalfa plant after exposure to aluminum.

The present invention provides for a seed of an alfalfa plant capable of producing an aluminum tolerant alfalfa plant. In one aspect, the aluminum tolerant alfalfa plant can be an open-pollinated variety, a hybrid parent inbred line, or a male sterile line.

The aluminum tolerant alfalfa plants of the present invention can be aluminum tolerant alfalfa lines adapted for field alfalfa production or any other growing environment. In one aspect, the aluminum tolerant alfalfa plants of the present invention are adapted for open field alfalfa production.

The present invention also provides for an intra-specific hybrid alfalfa plant having aluminum tolerance developed from aluminum tolerant alfalfa plants. In another aspect, those intra-specific hybrid alfalfa plants exhibit aluminum tolerance after exposure to aluminum.

Agronomically elite alfalfa plants appropriate for use in a commercial production field represent various aspects of the present invention. In one aspect, certain alfalfa traits, including, for example, hay or silage quality, may be important to the commercial value of the crop.

A further aspect of the invention relates to tissue cultures of the aluminum tolerant alfalfa plants described herein. As used herein, the term "tissue culture" indicates a composition comprising isolated cells of one or more types, or a collection of such cells organized into parts of a plant. Tissue culture includes, but is not limited to, compositions comprising protoplasts and calli. Tissue culture also includes, but is not limited to, compositions comprising plant cells that are present in intact plant tissues, or parts of plants, such as embryo, leaf, peduncle, pedicel, anther, meristem, tip and segments of root, stump and stem, explants, and the like. In one aspect, a tissue culture comprises embryos, protoplasts, meristematic cells, pollen, leaves, anthers or cells derived from immature tissues of these plant parts. Means for preparing and maintaining plant tissue cultures are well known in the art. Examples of processes of tissue culturing and regeneration of alfalfa are described in, for example, Parrot and Bouton, Crop Sci., (1990) 30:387-389. In some aspects, tissue culture of the aluminum tolerant alfalfa plants described herein relates to the culture of protoplasts, calli, or plant cells, that are isolated from, or present in, intact parts of the aluminum tolerant alfalfa plants described herein. In another aspect, tissue culture refers to the culture of protoplasts, calli, or plant cells, that are isolated from, or present in, intact parts of one or more aluminum tolerant alfalfa plants selected from the group consisting of Altet1, Altet2, Altet3 and/or Altet4 and aluminum tolerant descendants thereof, including those produced by crosses or backcrosses. In yet another aspect, tissue culture of the aluminum tolerant alfalfa plants described herein relates to the culture of protoplasts, calli, or plant cells, that are isolated from, or present in, intact parts of the aluminum tolerant plants described herein.

Once aluminum tolerant alfalfa plants are produced, the plants themselves can be cultivated in accordance with conventional procedures. Aluminum tolerant descendants of aluminum tolerant alfalfa plants may be obtained through sexual reproduction. The seeds resulting from sexual reproduction can be recovered from the aluminum tolerant alfalfa plants and planted or otherwise grown as a means of propagation. Aluminum tolerant descendants may also be obtained from aluminum tolerant alfalfa plants through asexual reproduction. Protoplast or propagules (e.g., cuttings, scions or rootstocks) can be recovered from aluminum tolerant alfalfa plants, or parts thereof, and may be employed to propagate aluminum tolerant alfalfa plants.

The present invention also provides for and includes a container of alfalfa seeds in which alfalfa plants grown from greater than 50% of the seeds have resistance or partial aluminum tolerance. In another aspect, alfalfa plants grown from greater than 55%, 60%, 65%, 70%, 75%, 80%, 85%, 90%, 95%, 98%, or 99% of the alfalfa seeds in the container have aluminum tolerance. Another aspect of the invention relates to seeds from an alfalfa plant selected from the group consisting of Altet1, Altet2, Altet3, Altet4 and aluminum tolerant descendents thereof, wherein alfalfa plants grown from about 50%, or greater than 50%, of the seeds have resistance or partial aluminum tolerance.

The container of alfalfa seeds can contain any number, weight or volume of seeds. For example, a container can contain about, or greater than about, 10, 25, 50, 100, 200, 300, 400, 500, 600, 700, 800, 900, 1000, 1500, 2000, 2500, 3000, 3500, 4000 or more seeds. In another aspect, a container can contain about, or greater than about, 1 gram, 5, 10, 15, 20, 25, 50, 100, 250, 500, or 1,000 grams of seeds. Alternatively, the container can contain about or at least, or greater than, about 1 ounce, 2, 3, 4, 5, 6, 7, 8, 9, 10 ounces, 1 pound, 2, 3, 4, 5, 6, 7, 8, 9, 10, 11, 12 pounds or more of seeds.

Containers of alfalfa seeds can be any container available in the art. For example, a container can be a box, a bag, a packet, a pouch, a tape roll, a foil, a pail, or a tube.

One aspect of the invention relates to dried, or otherwise processed alfalfa hay, produced by an alfalfa plant having a genome that comprises at least one genetic locus giving rise to aluminum tolerance when expressed in an alfalfa plant. Processed alfalfa can be in the form of, but is not limited to, hay, silage, haylage, fermented hay, or greenchop. In some aspects, the dried, or otherwise processed alfalfa, is from an alfalfa plant selected from one or more of the group consisting of Altet1, Altet2, Altet3 and/or Altet4, and aluminum tolerant descendents thereof.

The present invention includes and provides for *Medicago sativa* plants having at least one allele for a aluminum tolerance trait. The aluminum tolerant alfalfa plants can be either heterozygous or homozygous for the aluminum tolerance trait. In one embodiment, the aluminum tolerance trait can be linked to variations in a single gene (e.g., linked to one or more alleles of a single gene). In another embodiment, the aluminum tolerance trait can be linked to variations at one or one or more quantitative trait loci (QTL). In a yet another embodiment, the aluminum tolerant alfalfa plants are homozygous for the aluminum tolerance trait. In one aspect, the genetic loci derived from a aluminum tolerant alfalfa plant can be identified using genetic markers.

The present invention provides for an aluminum tolerant alfalfa plant having less than or equal to 50% of its genome derived from a non-M. sativa aluminum tolerant plant that can be crossed directly, or indirectly (e.g., through tissue culture manipulation, or through the use of a bridging species) with *Medicago sativa*. The present invention also provides for descendents of alfalfa plants having aluminum tolerance.

One aspect of the present invention provides for an aluminum tolerant alfalfa plant that contains a genetic marker or a complement to a genetic marker linked to one or more aluminum tolerance loci. Another aspect of the invention is an alfalfa plant that contains at least 1, 2, 3, or 4 sequences complementary to markers linked to a aluminum tolerance locus. In another aspect, an alfalfa plant can contain sequence complementary to any combination of markers linked to the aluminum tolerance locus.

As used herein linkage of two loci, including a marker sequence and an allele imparting a desired trait such as aluminum tolerance, may be genetic or physical or both. In one aspect of the invention, a nucleic acid marker and genetic locus conferring aluminum tolerance are genetically linked and, for example, are located less than 50 cM from one another. In particular embodiments, the marker and locus may exhibit a LOD score of greater than 2.0, as judged by interval mapping for the aluminum tolerance trait based on maximum likelihood methods described by Lander and Botstein, Genetics, 121:185-199 (1989), and implemented in the software package MAPMAKER (default parameters). In other embodiments, the marker and region conferring aluminum tolerance are genetically linked and exhibit a LOD score of greater than 3.0, or a LOD score of greater than 3.5, or a LOD score of about 4.0 based upon interval mapping.

In another aspect, the nucleic acid marker is genetically linked at a distance of between about 0 and about 49 centimorgans (cM) to the aluminum tolerance locus. In other embodiments, the distance between the nucleic acid marker and the aluminum tolerance locus is between about 0 and about 30 cM, or between about 0 and about 20 cM, or between about 0 and about 15 cM, or between about 0 and about 10 cM, or between about 0 and about 5 cM, or less.

In another aspect, the nucleic acid molecule may be physically linked to an aluminum tolerance locus. In some aspects, the nucleic acid marker specifically hybridizes to a nucleic acid molecule having a sequence that is within about 30 Mbp, or about 20 Mbp, or about 15 Mbp, or about 10 Mbp, or about 5 Mbp of an aluminum tolerance locus.

As used herein, two nucleic acid molecules are said to be capable of hybridizing to one another if the two molecules are capable of forming an anti-parallel, double-stranded nucleic acid structure. Conventional stringency conditions are described by Sambrook et al., *Molecular Cloning*, A Laboratory Manual, 2nd Ed., Cold Spring Harbor Press, Cold Spring Harbor, N.Y. (1989) and by Haymes et al., *Nucleic Acid Hybridization, A Practical Approach*, IRL Press, Washington, D.C. (1985). Departures from complete complementarity are therefore permissible, as long as such departures do not completely preclude the capacity of the molecules to form a double-stranded structure. Thus, in order for a nucleic acid molecule to serve as a primer or probe it need only be sufficiently complementary in sequence to be able to form a stable double-stranded structure under the particular solvent and salt concentrations employed.

Appropriate stringency conditions which promote DNA hybridization, for example, 6.0×sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1-6.3.6. In some embodiments, hybridization conditions can be high, moderate or low stringency conditions. High stringency conditions, for example, typically include a wash step at 65° C. in 0.2×SSC.

The specificity of hybridization can be affected by post-hybridization washes. For example, the salt concentration in the wash step can be selected from a low stringency of about 2.0×SSC at 50° C. to a moderate stringency of about 1.0×SSC at 50° C. to a high stringency of about 0.2×SSC at 50° C. In addition, the temperature in the wash step can be increased from low stringency conditions at room temperature, about 22° C., to moderate stringency conditions at about 50° C., to high stringency conditions at about 65° C. Both temperature and salt concentration may be varied, or either the temperature or the salt concentration may be held constant while the other variable is changed. In some aspects, the wash step can be performed for 5, 10, 15, 20, 25, 30, or more minutes. In another aspect, the wash step is performed for about 20 minutes. In yet another aspect, the wash step can be repeated 1, 2, 3, 4, or more times using the selected salt concentration, temperature, and time. In another aspect, the wash step is repeated twice.

A genetic marker profile of a plant may be predictive of the agronomic traits of a hybrid plant produced using that plant as a parent. For example, if an inbred plant having a known genetic marker profile and phenotype is crossed with a second inbred plant having a known genetic marker profile and phenotype, it is possible to predict the phenotype of the $F_1$ hybrid based on the combined genetic marker profiles of the parent inbred plants. Methods for prediction of hybrid performance from genetic marker data are disclosed in U.S. Pat. No. 5,492,547, the disclosure of which is specifically incorporated herein by reference in its entirety. Such predictions may be made using any suitable genetic marker, for example, SSRs, INDELs, RFLPs, AFLPs, SNPs, or isozymes.

Additional markers, such as SSRs, AFLP markers, RFLP markers, RAPD markers, phenotypic markers, SNPs, isozyme markers, or microarray transcription profiles that are genetically linked to or correlated with aluminum tolerance can be utilized (Walton, *Seed World* 22-29 (July, 1993); Burow and Blake, *Molecular Dissection of Complex Traits*, 13-29, Eds. Paterson, CRC Press, New York (1988)). Methods to isolate such markers are known in the art. For example, locus-specific SSRs can be obtained by screening an alfalfa genomic library for SSRs, sequencing of "positive" clones, designing primers which flank the repeats, and amplifying genomic DNA with these primers.

The genetic linkage of marker molecules to aluminum tolerance can be established by a gene mapping model such as, without limitation, the flanking marker model reported by Lander and Botstein, Genetics, 121:185-199 (1989), and the interval mapping, based on maximum likelihood methods described by Lander and Botstein, Genetics, 121:185-199 (1989), and implemented in the software package MAPMAKER.

A maximum likelihood estimate (MLE) for the presence of a marker is calculated, together with an MLE assuming no trait effect, to avoid false positives. A $\log_{10}$ of an odds ratio (LOD) is then calculated as: LOD=$\log_{10}$ (MLE for the presence of a trait (MLE given no linked trait)).

The LOD score essentially indicates how much more likely the data are to have arisen assuming the presence of a resistance allele rather than in its absence. The LOD threshold value for avoiding a false positive with a given confidence, say 95%, depends on the number of markers and the length of the genome. Graphs indicating LOD thresholds are set forth in Lander and Botstein, Genetics, 121:185-199 (1989), and further described by Ars and Moreno-Gonzalez, *Plant Breeding*, Hayward, Bosemark, Romagosa (eds.) Chapman & Hall, London, pp. 314-331 (1993).

Selection of appropriate mapping or segregation populations is important in trait mapping. The choice of appropriate mapping population depends on the type of marker systems employed (Tanksley et al., *Molecular mapping plant chromosomes. Chromosome structure and function: Impact of new concepts*, J. P. Gustafson and R. Appels (eds.), Plenum Press, New York, pp. 157-173 (1988)). Consideration must be given to the source of parents (adapted vs. exotic) used in the mapping population. Chromosome pairing and recombination rates can be severely disturbed (suppressed) in wide crosses (adapted x exotic) and generally yield greatly reduced linkage distances. Wide crosses will usually provide segregating populations with a relatively large array of polymorphisms when compared to progeny in a narrow cross (adapted×adapted).

The present application provides a genetic complement of the alfalfa lines described herein. Further provided is a hybrid genetic complement, wherein the complement is formed by the combination of a haploid genetic complement from elite inbred alfalfa lines described herein and another haploid genetic complement. Means for determining such a genetic complement are well-known in the art.

As used herein, the phrase "genetic complement" means an aggregate of nucleotide sequences, the expression of which defines the phenotype of a plant, such as a *Medicago sativa* alfalfa plant or a cell or tissue of that plant. By way of example, a *Medicago sativa* alfalfa plant is genotyped to determine a representative sample of the inherited markers it possesses. Markers may be inherited in codominant fashion so that the presence of both alleles at a diploid or tetraploid locus is readily detectable, and they are free of environmental variation, i.e., their heritability is close to, or equal to, 1. This genotyping is may be performed on at least one generation of the descendant plant for which the numerical value of the trait or traits of interest are also determined. The array of single locus genotypes is expressed as a profile of marker alleles, two at each locus for a diploid plant. The marker allelic composition of each locus can be either homozygous or heterozygous. Homozygosity is a condition where both alleles at a locus are characterized by the same conditions of the genome at a locus (e.g., the same nucleotide sequence). Heterozygosity refers to different conditions of the genome at a locus. Potentially any type of genetic marker could be used, for example, simple sequence repeats (SSRs), insertion/deletion polymorphism (INDEL), restriction fragment length polymorphisms (RFLPs), amplified fragment length polymorphisms (AFLPs), single nucleotide polymorphisms (SNPs), and isozymes.

Considerable genetic information can be obtained from a completely classified $F_2$ population using a codominant marker system (Mather, Measurement of Linkage in Heredity: Methuen and Co., (1938)). An $F_2$ population is the first generation of self or sib pollination after the hybrid seed is produced. Usually a single $F_1$ plant is self or sib pollinated to generate a population segregating for the nuclear-encoded genes in a Mendelian (1:2:1) fashion.

In contrast to the use of codominant markers, using dominant markers often requires progeny tests (e.g., $F_3$ or back cross self families) to identify heterozygous individuals in the preceding generation. The information gathered can be equivalent to that obtained in a completely classified $F_2$ population. This procedure is, however, often prohibitive because of the cost and time involved in progeny testing. Progeny testing of $F_2$ individuals is often used in map construction where error is associated with single plant phenotyping, or when sampling the plants for genotyping affects the ability to perform accurate phenotyping, or where trait expression is controlled by a QTL. Segregation data from progeny test populations (e.g., $F_3$ or backcrossed or selfed families) can be used in trait mapping. Marker-assisted selection can then be applied to subsequent progeny based on marker-trait map associations ($F_2$, $F_3$), where linkage has not been completely disassociated by recombination events (i.e., linkage disequilibrium).

Recombinant inbred lines (RILs) (genetically related lines; usually >$F_5$) can be used as a mapping population. RILs can be developed by selfing F2 plants, then selfing the resultant F3 plants, and repeating this generational selfing process, thereby increasing homozygosity. Information obtained from dominant markers can be maximized by using RILs because all loci are homozygous or nearly so. Under conditions of tight linkage (i.e., about <10% recombination), dominant and co-dominant markers evaluated in RIL populations provide more information per individual than either marker type in backcross populations (Reiter et al., *Proc. Natl. Acad. Sci.* (U.S.A.) 89:1477-1481 (1992)). However, as the distance between markers becomes larger (i.e., loci become more independent), the information in RIL populations decreases dramatically when compared to codominant markers.

Backcross populations can be utilized as mapping populations. A backcross population (BC) can be created by crossing an $F_1$ to one of its parents. Typically, backcross populations are created to recover the desirable traits (which may include most of the genes) from one of the recurrent parental (the parent that is employed in the backcrosses) while adding one or a few traits from the second parental, which is often referred to as the donor. A series of backcrosses to the recurrent parent can be made to recover most of the recurrent parent's desirable traits. Thus a population is created consisting of individuals nearly like the recurrent parent, wherein each individual carries varying amounts or a mosaic of genomic regions from the donor parent. Backcross populations can be useful for mapping dominant markers particularly if all loci in the recurrent parent are homozygous and the donor and recurrent parent have contrasting polymorphic marker alleles (Reiter et al., *Proc. Natl. Acad. Sci.* (*U.S.A.*) 89:1477-1481 (1992)).

Information obtained from backcross populations using either codominant or dominant markers is less than that obtained from completely classified $F_2$ populations because recombination events involving one, rather than two, gametes are sampled per plant. Backcross populations, however, are more informative (at low marker saturation) when compared to RILs as the distance between linked loci increases in RIL populations (i.e., about 15% recombination). Increased recombination can be beneficial for resolution of tight linkages, but may be undesirable in the construction of maps with low marker saturation.

Near-isogenic lines (NIL) created by many backcrosses to produce an array of individuals that are nearly identical in genetic composition except for the trait or genomic region under interrogation can be used as a mapping population. In mapping with NILs, only a portion of the loci are polymorphic between the parentals are expected to segregate in the highly homozygous NIL population. Those loci that are polymorphic in a NIL population, however, are likely to be linked to the trait of interest.

Bulk segregant analysis (BSA) is a method developed for the rapid identification of linkage between markers and traits of interest (Michelmore, et al., *Proc. Natl. Acad. Sci. (U.S.A.)* 88:9828-9832 (1991)). In BSA, two bulk DNA samples are drawn from a segregating population originating from a single cross. These bulk samples contain individuals that are identical for a particular trait (e.g., resistant or susceptible to a particular pathogen) or genomic region but arbitrary at unlinked regions (i.e., heterozygous). Regions unlinked to the target trait will not differ between the bulked samples of many individuals in BSA.

In another aspect, the present invention provides a method of producing an aluminum tolerant alfalfa plant comprising: (a) crossing an aluminum tolerant alfalfa line with a second alfalfa line lacking aluminum tolerance to form a segregating population; (b) screening the population for aluminum tolerance; and (c) selecting one or more members of the population having said aluminum tolerance. In one aspect, plants are identified as aluminum tolerant prior to conducting one or more crosses. In one aspect, plants can be selected on the basis of partial or complete aluminum tolerance. In one aspect, the segregating population is self-crossed and the subsequent population is screened for resistance.

In another aspect, the present invention provides a method of introgressing aluminum tolerance into an alfalfa plant comprising: (a) crossing at least a first aluminum tolerant alfalfa line with a second alfalfa line to form a segregating population; (b) screening said population for aluminum tolerance; and (c) selecting at least one member of said population exhibiting aluminum tolerance. In one aspect, plants are identified as aluminum tolerant prior to conducting one or more crosses. In one aspect, the segregating population is self-crossed and the subsequent population is screened for resistance.

Aluminum tolerant alfalfa plants of the present invention can be part of, or generated from, a breeding program. The choice of breeding method depends on the mode of plant reproduction, the heritability of the trait(s) being improved, and the type of cultivar used commercially (e.g., $F_1$ hybrid cultivar, pure line cultivar, etc). Selected, non-limiting approaches for breeding the plants of the present invention are set forth below. A breeding program can be enhanced using marker-assisted selection, or marker-assisted backcrossing, of the descendents of any cross. It is further understood that any commercial and non-commercial cultivars can be utilized in a breeding program. Factors such as, for example, emergence vigor, vegetative vigor, stress tolerance, disease resistance, branching, flowering, seed size, forage quality, and/or forage yield will generally dictate the choice.

For highly heritable traits, a choice of superior individual plants evaluated at a single location will be effective, whereas for traits with low heritability, selection should be based on statistical analyses (e.g., mean values) obtained from replicated evaluations of families of related plants. Popular selection methods commonly include pedigree selection, modified pedigree selection, mass selection, and recurrent selection. In some embodiments a backcross or recurrent breeding program is undertaken.

The complexity of inheritance influences choice of the breeding method. Backcross breeding can be used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Breeding lines can be tested and compared to appropriate standards in environments representative of the commercial target area(s) for two or more generations. The best lines are candidates as parents for new commercial cultivars; those still deficient in traits may be used as parents for hybrids, or to produce new populations for further selection.

One method of identifying a superior plant is to observe its performance relative to other experimental plants and to a widely grown standard cultivar. If a single observation is inconclusive, replicated observations can provide a better performance estimate. A breeder can select and cross two or more parental lines, followed by repeated self or sib pollinating and selection, producing many new genetic combinations.

The development of new alfalfa lines requires the preparation and selection of alfalfa varieties, the crossing of these varieties and selection of superior hybrid crosses. The hybrid seed can be produced by manual crosses between selected male-fertile parents or by using male sterility systems. Hybrids can be selected for certain single gene traits such as flower color, seed yield or herbicide resistance that indicate that the seed is truly a hybrid. Additional data on parental lines, as well as the phenotype of the hybrid, influence the breeder's decision whether to continue with the specific hybrid cross.

Pedigree breeding and recurrent selection breeding methods can be used to develop cultivars from breeding populations. Breeding programs combine desirable traits from two or more cultivars or various broad-based sources into breeding pools from which cultivars are developed by selfing and selection of desired phenotypes into parent lines. These lines are used to produce new cultivars. New cultivars can be evaluated to determine which have commercial potential.

Pedigree breeding is used commonly for the improvement of self-pollinating crops. Two parents who possess favorable, complementary traits are crossed to produce an $F_1$. An $F_2$ population is produced by selfing one or several $F_1$'s. Selection of the best individuals in the best families is performed. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Backcross breeding and cross breeding have been used to transfer genes for a simply inherited, highly heritable trait into a desirable homozygous cultivar or inbred line, which is the recurrent parent. The source of the trait to be transferred is called the donor parent. The resulting plant obtained from a successful backcrossing program is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. After multiple backcrossing generations with selection, the resulting line is expected to have the attributes of the recurrent parent (e.g., cultivar) and the desirable trait transferred from the donor parent.

Cross breeding or backcross breeding of a aluminum tolerant alfalfa plant may be conducted where the other parent (second alfalfa plant) is aluminum tolerant or the other parent is not aluminum tolerant.

Alfalfa plants generated of the invention may be generated using a single-seed descent procedure. The single-seed descent procedure, in the strict sense, refers to planting a segregating population, then selecting one plant in this and each subsequent generation to self and create the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

Descriptions of other breeding methods that are commonly used for different traits and crops can be found in reference texts (e.g., Fehr, *Principles of Cultivar Development* Vol. 1, pp. 2-3 (1987)).

In one aspect of the present invention, the source of aluminum tolerance trait for use in a breeding program is derived from a plant selected from the group consisting of Altet1, Altet2, Altet3, Altet4 and aluminum tolerant descendants thereof. In another aspect, the source of the aluminum tolerance trait for use in a breeding program is derived from a plant selected from the group consisting of Altet4 and aluminum tolerant descendants thereof.

Another aspect of the invention is directed to an inbred alfalfa plant, wherein said resistance is exhibited when said plant is in contact with aluminum. In one embodiment the inbred plant is a aluminum tolerant alfalfa plant. Also included in the invention is an alfalfa plant having a genome, wherein said genome comprises one or more genetic loci conferring aluminum tolerance, wherein said one or more genetic loci associated with one or more genetic markers linked thereto.

In one aspect, additional sources of aluminum tolerance for use in a breeding program can be identified by screening alfalfa germplasm for aluminum tolerance. In a yet another aspect, alfalfa plants can be screened for aluminum tolerance by identifying germplasm exhibiting reduced aluminum toxicity relative to a control alfalfa plant after inoculation or infection. In one aspect, alfalfa plants can be screened for aluminum tolerance using a method as described in Example 2. In another aspect, alfalfa plants can be screened for aluminum tolerance using a method as described in Example 3.

In another aspect, additional sources of aluminum tolerance for use in a breeding program can be identified by screening with one or more molecular markers linked to a genetic locus conferring aluminum tolerance.

In another aspect, aluminum tolerant alfalfa plants, varieties, lines or cultivars can be used in breeding programs to combine aluminum tolerance with additional traits of interest. In one aspect, aluminum tolerance can be combined with any additional trait, including other disease resistant traits, yield traits, and hay quality traits. Breeding programs can also be used to combine aluminum tolerance with one or more disease resistant traits. In another aspect, the traits that are combined can be co-inherited in subsequent crosses.

The present invention also provides for parts of the aluminum tolerant alfalfa plants produced by a method of the present invention. Parts of alfalfa plants, without limitation, include plant cells or parts of plant cells, seed, endosperm, meristem, flower, anther, ovule, pollen, callus, flowers, stems, roots, stalks or leaves, scions, and root stocks. In one embodiment of the present invention, the plant part is a seed.

The invention further provides for parts of a aluminum tolerant alfalfa plant having a genome, which comprises at least one genetic locus giving rise to aluminum tolerance in the alfalfa plant. In another embodiment, parts of alfalfa plants are derived from an alfalfa plant selected from the group consisting of Altet1, Altet2, Altet3 and Altet4, and aluminum tolerant descendants thereof.

One aspect of the invention includes a aluminum tolerant alfalfa plant, or the hay or seeds thereof, wherein the alfalfa plant, or the hay or seeds thereof, expresses one, or two, or three, or more independently selected desirable traits in addition to aluminum tolerance. In other aspects of the invention, the plants bearing one or more desirable traits in addition to aluminum tolerance display a greater than 10%, or a greater than 30%, or a greater than 60%, or a greater than 80% reduction in of aluminum toxicity symptoms relative to a non-resistant control plant upon exposure to aluminum. Another aspect of the present invention is directed to a method of producing a aluminum tolerant alfalfa plant comprising: crossing a aluminum tolerant alfalfa plant, or a plant from a aluminum tolerant alfalfa line, cultivar or variety with a second plant lacking aluminum tolerance but capable of donating one or more of the aforementioned desirable traits.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Generation of Plant Materials

Al-4 is a known aluminum-tolerant alfalfa genotype, which is derived from PI464724-25 (Narasimhamoorthy et al., 2007a). Al-4 was crossed with individual genotypes from the synthetic non-dormant tetraploid variety CUF-101 (Lehman et al., 1983) producing progeny Altet1 through Altet4.

The aluminum-tolerant Altet4 was crossed with two alfalfa genotypes, 95-608 and NECS141, to create two mapping populations. 95-608 is derived from CUF-101. NECS141 is a semi-dormant breeding line derived from a cross of 5454, Oneica VR and Apica. At least 190 F1 individuals from each cross were randomly selected for each population. The two populations were designated 608Altet4 and NECS141Altet4 respectively.

Each individual genotype was aseptically germinated by soaking the seeds in 70% ethanol for five minutes followed by rinsing three times with sterile double distilled water for five minutes. Because of inbreeding depression in alfalfa, inbred lines are not widely used. Instead, stem cuttings are used to evaluate the same genotype across replications and treatments. All genotypes were clonally propagated using axillary meristems and/or terminal meristems subcultured in MS media (Murashige and Skoog, 1962) containing 2 mg/l of indole-3-butyric acid (IBA).

Example 2

Tissue-Culture (Callus) Assay for Evaluating Aluminum Tolerance

Aluminum tolerance was evaluated using callus. Callus formation was induced using modified Blaydes callus induction media for two weeks (Parrott and Bouton, 1990). The calli were grown in controlled environment growth chambers at 25° C. with an 18 hour light photoperiod. Half of a single 2-week old callus was transferred to Blaydes media with aluminum (+Al; pH 4.0 with 400 μM of $Al^{+3}$ supplied as $AlCl_3$) and the other half was transferred to Blaydes media without aluminum (−Al; pH 4.0) as described by Parrot and Bouton, 1990. Individual calli were weighed and transferred to fresh +Al and −Al media at one week intervals for 8 weeks after transfer to conditioned medium to determine the relative growth rate of each genotype. The experimental design was a randomized complete block design with three replications, each of which consisted of five individual calli per genotype per treatment.

Each individual genotype from the mapping populations 608Altet4 and NECS141Altet4 was evaluated for aluminum tolerance using this method.

Example 3

Whole-Plant Culture Media Assay for Evaluating Aluminum Tolerance

Vegetatively propagated alfalfa clones (stem cuttings) were used as replicates to evaluate aluminum tolerance. Terminal stem cuttings including the terminal bud were sterilized with 70% ethanol for 2 minutes and soaked in bleach for 2 minutes, then rinsed three times with double distilled sterile water for 5 minutes each time and transferred to MS media for growth. Stem cuttings were then transferred to least macro salt (LMS) media for 1 week to induce root formation and then transferred to MS media. Apical stem cuttings of these propagated plants were obtained from plants grown in vitro and transferred to LMS media to induce root formation for seven days. The most uniform rooted plants were selected and transferred to one of three conditions: i) media with 400 μM $CaCl_2$, 1.4% gel rite, and pH 7 without Al (Ca7); ii) media with 400 μM $CaCl_2$, 1.4% gel rite, and pH 4 without Al (Ca4); iii) media with 400 μM $CaCl_2$, 1.4% gel rite, and pH 4 with Al 50 μM $Al^{+3}$ in the form of $AlCl_3$ (CaAl50). Plants wer in controlled growth chambers at 25° C. and with an 18-hour light photoperiod.

Fourteen days after stem cuttings were transferred to Ca7, Ca4 or CaAl50 medium, roots were scanned using an HP scanner (Scanjet 3500C, with a black background at 600 dpi). Quantification of total root length, lateral root numbers and branching was performed using the winRHIZO software (Regent Instruments, Québec, Canada). The absolute root growth and ratio of root characteristics (biomass, length and branching) after growth in Ca7, Ca4, and CaAl50 was used as quantitative data for determining aluminum tolerance. Each individual genotype from the mapping populations 608Altet4 and NECS141Altet4 was evaluated for aluminum tolerance using this method.

Acid tolerance is controlled for by comparing the ratio of the root characteristics (root biomass, length and branching) between plants grown in Ca4 and Ca7 (pH4/pH7) while Al tolerance is represented with the ratio of root growth between CaAl50 and Ca7 (pH4+Al/pH7).

Example 4

Markers Used for Genotyping Plant Materials

Genomic DNA from the 608Altet4 and NECS141Altet4 mapping populations was extracted using DNeasy Plant Mini Kit (QIAGEN, CAT. No. 69104, Valencia, USA). A total of 2738 primer pairs distributed throughout the alfalfa linkage groups (Sledge et al., 2005), 125 SSR (simple sequence repeat) primer pairs developed from trichome ESTs (expressed sequence tags; www.trichome.noble.org/trichomeb/) (Table 1), and candidate genes involved in aluminum tolerance were used to evaluate polymorphism between the parental genotypes Altet4, 95-608 and NECS141, and to confirm the hybrid status of the mapping population F1 progeny.

TABLE 1

Alfalfa trichome EST-SSRs used to genotype the 608Altet4 and NECS141Altet4 mapping populations.

| Primer | Forward | Reverse |
|---|---|---|
| MsTri10009 | TGTAAAACGACGGCCAGTAAAGAATTTTAGTCTTTGCGAGAA (SEQ ID NO: 1) | CCGAGTGTGTTCGATAGCATT (SEQ ID NO: 2) |
| MsTri10030 | TGTAAAACGACGGCCAGTCGGCATTGATTTTCTTCACAA (SEQ ID NO: 3) | GCCTCAACCTAGTTCCAAACC (SEQ ID NO: 4) |
| MsTri10060 | TGTAAAACGACGGCCAGTATATCACCACTTAGCCGAGCC (SEQ ID NO: 5) | TGATCGAGATTTTGAGCCTGT (SEQ ID NO: 6) |
| MsTri10127 | TGTAAAACGACGGCCAGTAATTCCCAATTCTCATTCGTG (SEQ ID NO: 7) | GGGAAACCATTTCGTACCCTA (SEQ ID NO: 8) |
| MsTri10184 | TGTAAAACGACGGCCAGTGCTTTAACCGATTCAGTTTCTCTC (SEQ ID NO: 9) | TCATCACATGACGAAGCTCAG (SEQ ID NO: 10) |
| MsTri10235 | TGTAAAACGACGGCCAGTCCTTAACACATTTTTGCTTCA (SEQ ID NO: 11) | TTGCCATCGTAGAAAATGGTC (SEQ ID NO: 12) |
| MsTri10316 | TGTAAAACGACGGCCAGTGGTATGTTCGGATCTTGGTGA (SEQ ID NO: 13) | CAACAGCTCCCTGAAAAACAG (SEQ ID NO: 14) |
| MsTri10349 | TGTAAAACGACGGCCAGTTGTACTTGCAGGGTGTTTTCA (SEQ ID NO: 15) | AACTTTCATTCTAATGCCACA (SEQ ID NO: 16) |
| MsTri10409 | TGTAAAACGACGGCCAGTTGGTTACAACCACGGTGGAG (SEQ ID NO: 17) | TGATCAGTTTTGAGTTTTGTC (SEQ ID NO: 18) |

TABLE 1-continued

Alfalfa trichome EST-SSRs used to genotype the
608Altet4 and NECS141Altet4 mapping populations.

| Primer | Forward | Reverse |
|---|---|---|
| MsTri10456 | TGTAAAACGACGGCCAGTTTATCATGTGCAGACAATACC (SEQ ID NO: 19) | TGTCGTCTTTTGACCATTTCC (SEQ ID NO: 20) |
| MsTri10472 | TGTAAAACGACGGCCAGTAAGAGAAAGAAGGGGAACG (SEQ ID NO: 21) | CTCTTACTCTTCCTCACCGGC (SEQ ID NO: 22) |
| MsTri10581 | TGTAAAACGACGGCCAGTGTCTGCTGCTCCAGCTAAGAA (SEQ ID NO: 23) | CCTTGGCAGCTACAGGTACAG (SEQ ID NO: 24) |
| MsTri10584 | TGTAAAACGACGGCCAGTCCAAATATCTTCGCTCTTCCA (SEQ ID NO: 25) | TCACATCAGCCCTAACATTCC (SEQ ID NO: 26) |
| MsTri10592 | TGTAAAACGACGGCCAGTGGTTGAAATCGACATGAGAGG (SEQ ID NO: 27) | GATTAAACATACATGCAACATTGA (SEQ ID NO: 28) |
| MsTri10615 | TGTAAAACGACGGCCAGTGCTGTTGGTGCTCTTGCTACT (SEQ ID NO: 29) | TTCTGAGCAGGAATCAAAGGA (SEQ ID NO: 30) |
| MsTri10646 | TGTAAAACGACGGCCAGTCAGGAAAACTTGAAGAAGCAGA (SEQ ID NO: 31) | TCCATGGTATTTTGGTAAAACTC (SEQ ID NO: 32) |
| MsTri10649 | TGTAAAACGACGGCCAGTACAACCCCATTTCCAACTTTC (SEQ ID NO: 33) | GGATATCCTGGTGGAGGGTAA (SEQ ID NO: 34) |
| MsTri10665 | TGTAAAACGACGGCCAGTCCAATGCAGTTCGGTAATCC (SEQ ID NO: 35) | CCTCCAGGTCTAAGTCCCATT (SEQ ID NO: 36) |
| MsTri10686 | TGTAAAACGACGGCCAGTTGTTCTCCTCTCTTCGTCTCTTG (SEQ ID NO: 37) | CCAACACTTTAAGCCTCCAAA (SEQ ID NO: 38) |
| MsTri10688 | TGTAAAACGACGGCCAGTAGTGTTGGTTTCCTTGAATTTT (SEQ ID NO: 39) | GTAGCGGGCGCTATTTCGT (SEQ ID NO: 40) |
| MsTri10743 | TGTAAAACGACGGCCAGTAACCAGAGAAAAATCCAACCA (SEQ ID NO: 41) | CCGGTTCTGTTTGGTAGTGAA (SEQ ID NO: 42) |
| MsTri10745 | TGTAAAACGACGGCCAGTGCCTTTTATCGGCTGATTTCT (SEQ ID NO: 43) | TCCTATCCAGTTACGGATCATTTT (SEQ ID NO: 44) |
| MsTri10801 | TGTAAAACGACGGCCAGTTCACAAAACAAACCCTTCTTCT (SEQ ID NO: 45) | GGAGCAAACATTCTACCACCA (SEQ ID NO: 46) |
| MsTri10860 | TGTAAAACGACGGCCAGTATCGACAGGTACCGGAACAG (SEQ ID NO: 47) | CATCATTCATTCCTCCAGCTC (SEQ ID NO: 48) |
| MsTri10866 | TGTAAAACGACGGCCAGTTAAGGGTTCATGCTCACCATC (SEQ ID NO: 49) | CCTTAGGCACATTGAAAACCA (SEQ ID NO: 50) |
| MsTri10873 | TGTAAAACGACGGCCAGTTCGCTCCTACTTCTTCTGGTG (SEQ ID NO: 51) | TGGGTCTTGGGTAGATGAATG (SEQ ID NO: 52) |
| MsTri10888 | TGTAAAACGACGGCCAGTTCTTGCATTGCACCATAAACC (SEQ ID NO: 53) | CCGTTGATCCTGTCACAAACT (SEQ ID NO: 54) |
| MsTri10914 | TGTAAAACGACGGCCAGTTTTTCCGCTTCCGTTTTT (SEQ ID NO: 55) | TTCTGAATACCACCAACTCCG (SEQ ID NO: 56) |
| MsTri10916 | TGTAAAACGACGGCCAGTAGAAAGGGAGGATCTCTGCG (SEQ ID NO: 57) | GTTGTTCCTCCCCTGTTCTTC (SEQ ID NO: 58) |
| MsTri10963 | TGTAAAACGACGGCCAGTGTTGCGGTGGAAGAGAAACC (SEQ ID NO: 59) | TTCCCAGCAAAAACAATTTCA (SEQ ID NO: 60) |
| MsTri11061 | TGTAAAACGACGGCCAGTACCTGAAAGGCCACAAAAGAT (SEQ ID NO: 61) | AACATGCACAATTAAGCATTCAA (SEQ ID NO: 62) |
| MsTri11067 | TGTAAAACGACGGCCAGTTTGCCTCGGATTATTACTTGTG (SEQ ID NO: 63) | AATTCGGGTGGAATAACAAGC (SEQ ID NO: 64) |
| MsTri11087 | TGTAAAACGACGGCCAGTTCATCCATTCATTAAAACGCA (SEQ ID NO: 65) | TGACTTAGACACCACCGGAGT (SEQ ID NO: 66) |
| MsTri11089 | TGTAAAACGACGGCCAGTTTAGGGTTAGATTCGTCGATCA (SEQ ID NO: 67) | AAACCAGCCGAAGAGGATTT (SEQ ID NO: 68) |

TABLE 1-continued

Alfalfa trichome EST-SSRs used to genotype the
608Altet4 and NECS141Altet4 mapping populations.

| Primer | Forward | Reverse |
|---|---|---|
| MsTri11090 | TGTAAAACGACGGCCAGTGCCAGTTTTGGGCAATTTTAT (SEQ ID NO: 69) | GCAATCACCTTAGCATTTTGG (SEQ ID NO: 70) |
| MsTri11102 | TGTAAAACGACGGCCAGTTTGTTCTGTTCTCTCACCCGA (SEQ ID NO: 71) | CAAGCTTGCATTCTTCGTTTC (SEQ ID NO: 72) |
| MsTri11131 | TGTAAAACGACGGCCAGTGGGACCTAATATGATGAACTTACA (SEQ ID NO: 73) | GTTCAAGCATGGAAAGTTTGG (SEQ ID NO: 74) |
| MsTri11170 | TGTAAAACGACGGCCAGTCGACGTCGTCTTCTGTTAAT (SEQ ID NO: 75) | GGCACTCCTAACCTGTTTTCC (SEQ ID NO: 76) |
| MsTri11280 | TGTAAAACGACGGCCAGTTCAAATTTGGTTGTGTAATTTT (SEQ ID NO: 77) | CATCAATAAGCCCAATCCTCA (SEQ ID NO: 78) |
| MsTri11290 | TGTAAAACGACGGCCAGTCCCTTACCCCTGTTTTCATTT (SEQ ID NO: 79) | ACACAACATTTTGTCGGTTGA (SEQ ID NO: 80) |
| MsTri11294 | TGTAAAACGACGGCCAGTAAATTCACCACCACCCACTTT (SEQ ID NO: 81) | AATGGGTTTGGAGAAAGGATG (SEQ ID NO: 82) |
| MsTri11311 | TGTAAAACGACGGCCAGTGACGAACTCTTTTCTTTTCTGACA (SEQ ID NO: 83) | TGACAGTTTCCACAATCCTCC (SEQ ID NO: 84) |
| MsTri11312 | TGTAAAACGACGGCCAGTTCTGTTCTGTTCTGTTCCTCCA (SEQ ID NO: 85) | TGACAGTTTCCACAATCCTCC (SEQ ID NO: 86) |
| MsTri11314 | TGTAAAACGACGGCCAGTTAATTCGAGGAGGATTGTGGA (SEQ ID NO: 87) | ATACACCATAGCACGAGACGC (SEQ ID NO: 88) |
| MsTri11325 | TGTAAAACGACGGCCAGTCCTCCTTATCCTCCTCCCTCT (SEQ ID NO: 89) | TGAATTCAGGGTCAAGGTCAC (SEQ ID NO: 90) |
| MsTri11386 | TGTAAAACGACGGCCAGTAACAGAGTTGTTCATGGCTGG (SEQ ID NO: 91) | AGCACCAAAATTAAACACCCC (SEQ ID NO: 92) |
| MsTri11419 | TGTAAAACGACGGCCAGTTGAAGGAAGAAGGAAGAAGGAA (SEQ ID NO: 93) | ACAAGAAGAAGATTGCGACGA (SEQ ID NO: 94) |
| MsTri11421 | TGTAAAACGACGGCCAGTATCTCTGCTGTTGCCTAATGC (SEQ ID NO: 95) | TCCTCTTTCCAAAGGAAACAAA (SEQ ID NO: 96) |
| MsTri11442 | TGTAAAACGACGGCCAGTTGATTTCACTTTAGCATCTTGTG (SEQ ID NO: 97) | GGATCCATTACCAGACAGTGC (SEQ ID NO: 98) |
| MsTri11460 | TGTAAAACGACGGCCAGTCAAGAACCAGATCATCAACAACA (SEQ ID NO: 99) | AATTTGGACTTTGATTGTGCG (SEQ ID NO: 100) |
| MsTri11465 | TGTAAAACGACGGCCAGTCACAACACACGCTACCCTACA (SEQ ID NO: 101) | ATGCTTTCTGTGTTTTGGTGG (SEQ ID NO: 102) |
| MsTri11470 | TGTAAAACGACGGCCAGTTTGAAATAGTGCAAGAAGAACCC (SEQ ID NO: 103) | GGAGATGAAGAAGGAGATGGG (SEQ ID NO: 104) |
| MsTri11496 | TGTAAAACGACGGCCAGTTCTACTTTTCTTGTGTGTGATTCC (SEQ ID NO: 105) | TAGCCTCAAGCTTCAATCCAA (SEQ ID NO: 106) |
| MsTri11501 | TGTAAAACGACGGCCAGTTCTGGAATTGGAAGAGATTGC (SEQ ID NO: 107) | GGCCGTATTTCGCTCTTTCTA (SEQ ID NO: 108) |
| MsTri11509 | TGTAAAACGACGGCCAGTCTTTTTCATTCTGTAACACATATT (SEQ ID NO: 109) | CCACAATTTCTGAACCCTCAA (SEQ ID NO: 110) |
| MsTri11511 | TGTAAAACGACGGCCAGTTGATTGGTCAACTGAGATTCAAA (SEQ ID NO: 111) | GACACAACATCACCACCATCA (SEQ ID NO: 112) |
| MsTri11523 | TGTAAAACGACGGCCAGTGGAGAGAGCAAAGTCTCTTCAA (SEQ ID NO: 113) | TGTCACTTGTTCTGGTCCTTCT (SEQ ID NO: 114) |
| MsTri11531 | TGTAAAACGACGGCCAGTACTTATCAGAATCTAATTGGGC (SEQ ID NO: 115) | CGTTGTTGATGAAGTTGGTGA (SEQ ID NO: 116) |
| MsTri11539 | TGTAAAACGACGGCCAGTTTCATGAATTTGCTTCTATTGCAT (SEQ ID NO: 117) | AAATTTCTTTCCATTGGCTCC (SEQ ID NO: 118) |

TABLE 1-continued

Alfalfa trichome EST-SSRs used to genotype the
608Altet4 and NECS141Altet4 mapping populations.

| Primer | Forward | Reverse |
|---|---|---|
| MsTri11541 | TGTAAAACGACGGCCAGTTTGACAAATATCATCCTTAGATCG (SEQ ID NO: 119) | TTGTTCCATTGTTTTTGTGAGG (SEQ ID NO: 120) |
| MsTri11552 | TGTAAAACGACGGCCAGTACATTCTCTTCGTGCCCTCC (SEQ ID NO: 121) | CGCAGCACATGTAACTTGAAA (SEQ ID NO: 122) |
| MsTri11701 | TGTAAAACGACGGCCAGTTTTCATCAACATCAAACACCG (SEQ ID NO: 123) | AGCTTTTTCAACGAGTTCAGC (SEQ ID NO: 124) |
| MsTri11704 | TGTAAAACGACGGCCAGTTTCGATTCTCAATTCTTCACTCA (SEQ ID NO: 125) | CATAAACCCGCATTGAGACAT (SEQ ID NO: 126) |
| MsTri11744 | TGTAAAACGACGGCCAGTCCGATTGGACTCGGAACTT (SEQ ID NO: 127) | TTCTTGGCTTCGACTTCTTCA (SEQ ID NO: 128) |
| MsTri11748 | TGTAAAACGACGGCCAGTTCTGTAACACAGGCAGAGTCG (SEQ ID NO: 129) | GGATTTCGTTTGGGTTCATTT (SEQ ID NO: 130) |
| MsTri11830 | TGTAAAACGACGGCCAGTCCCCTAAATTCCCAATTCTTC (SEQ ID NO: 131) | GTCTACACCCTGTAATCCGCA (SEQ ID NO: 132) |
| MsTri11853 | TGTAAAACGACGGCCAGTACTGAGAAAAGGAAACTGCCC (SEQ ID NO: 133) | TCATCAAGCATTGCACTCAAG (SEQ ID NO: 134) |
| MsTri11888 | TGTAAAACGACGGCCAGTTCCACAAAAGGGTGTGAGAAA (SEQ ID NO: 135) | AAAGGTGGTTCTTCCTTATTCA (SEQ ID NO: 136) |
| MsTri11932 | TGTAAAACGACGGCCAGTATGGAATCAGCATACAGGGC (SEQ ID NO: 137) | CTCGGTTGTCATCACCAAGAT (SEQ ID NO: 138) |
| MsTri11972 | TGTAAAACGACGGCCAGTAGCTCTGTTTTGTCCTGCTTG (SEQ ID NO: 139) | CGAACAAGATTACCGAGATGG (SEQ ID NO: 140) |
| MsTri11989 | TGTAAAACGACGGCCAGTTCCTAATACCCCATTCATTGGT (SEQ ID NO: 141) | CAGGAACATAACTGTGACCCG (SEQ ID NO: 142) |
| MsTri11997 | TGTAAAACGACGGCCAGTTGTCGAAATATCATGATTGGG (SEQ ID NO: 143) | ATTCGTAGGCCGACAATTTTT (SEQ ID NO: 144) |
| MsTri12038 | TGTAAAACGACGGCCAGTAAGATTAGGGTTTGAGTAAGGGAA (SEQ ID NO: 145) | GCCTTTAGGCCAATCAGAGAC (SEQ ID NO: 146) |
| MsTri7231 | TGTAAAACGACGGCCAGTGGTAGTACTTCCTTCACTCTTCT (SEQ ID NO: 147) | ACATCTTCTGGAAGACCCGTT (SEQ ID NO: 148) |
| MsTri7274 | TGTAAAACGACGGCCAGTACTCCATCAACTGGTTCACCG (SEQ ID NO: 149) | CACACATCAAAGCCCCTAAAA (SEQ ID NO: 150) |
| MsTri7509 | TGTAAAACGACGGCCAGTCGAAAGATAAAATAATTGAATCGG (SEQ ID NO: 151) | ATCTCTTAGCCTCGTTGGCTC (SEQ ID NO: 152) |
| MsTri7607 | TGTAAAACGACGGCCAGTTGTCTGTTCGTATTTGTTGTTCTG (SEQ ID NO: 153) | GTCACAACTGTTACCATGCCC (SEQ ID NO: 154) |
| MsTri7698 | TGTAAAACGACGGCCAGTAAGCGATTTCATTAGTAGTTGT (SEQ ID NO: 155) | CAGTTGATGCATAGAAACGCA (SEQ ID NO: 156) |
| MsTri7729 | TGTAAAACGACGGCCAGTTCAAAACCTTGGTGTTGGTTG (SEQ ID NO: 157) | ATCTGGGAAGTGTGACCTCCT (SEQ ID NO: 158) |
| MsTri7771 | TGTAAAACGACGGCCAGTCTCTTTAAGATTGCTTCTCTTGC (SEQ ID NO: 159) | CATACTATGGTGGTGGTTGGG (SEQ ID NO: 160) |
| MsTri7793 | TGTAAAACGACGGCCAGTACTTGTTGATCTGGACGATGA (SEQ ID NO: 161) | GCTTAGCATTTCCATTGTTCTACA (SEQ ID NO: 162) |
| MsTri7807 | TGTAAAACGACGGCCAGTAACAACCTAGATTTTCTCGACC (SEQ ID NO: 163) | TCACCAGCACATGAATCAAAA (SEQ ID NO: 164) |
| MsTri8035 | TGTAAAACGACGGCCAGTGCCATCTTTATTTTGGATGTCA (SEQ ID NO: 165) | CCTCCAATAATGGTGGACACA (SEQ ID NO: 166) |
| MsTri8112 | TGTAAAACGACGGCCAGTTCATAATCACTCACTCTCCCTT (SEQ ID NO: 167) | ATCCGCATCCAAACTAGGTCT (SEQ ID NO: 168) |

TABLE 1-continued

Alfalfa trichome EST-SSRs used to genotype the
608Altet4 and NECS141Altet4 mapping populations.

| Primer | Forward | Reverse |
|---|---|---|
| MsTri8119 | TGTAAAACGACGGCCAGTATTGCAATCATCTTCTCCCCT (SEQ ID NO: 169) | AGGGTTGATGCAGATGTTACG (SEQ ID NO: 170) |
| MsTri8128 | TGTAAAACGACGGCCAGTCACTCTCTCACTTCATTTGAAAAA (SEQ ID NO: 171) | AAAGGGTAATCGAAAAGCCAA (SEQ ID NO: 172) |
| MsTri8192 | TGTAAAACGACGGCCAGTCAGGTGGATGGAGAGAGTCAA (SEQ ID NO: 173) | GCTGGGAGACAAGTGTTGCTA (SEQ ID NO: 174) |
| MsTri8451 | TGTAAAACGACGGCCAGTCACCGCCTGTTCTATCATGTG (SEQ ID NO: 175) | ACTTGTCCATCTCCATCTCCA (SEQ ID NO: 176) |
| MsTri8491 | TGTAAAACGACGGCCAGTCGAGGCATCTTCATCTTCAAC (SEQ ID NO: 177) | GGACGGTTTCGAACTTCTAGC (SEQ ID NO: 178) |
| MsTri8616 | TGTAAAACGACGGCCAGTGGAAGATCACCATTTTGTCCA (SEQ ID NO: 179) | AACAATATGATCTGGCATGTCG (SEQ ID NO: 180) |
| MsTri8637 | TGTAAAACGACGGCCAGTCTCTTTTCTCTTCAATTTTCAAT (SEQ ID NO: 181) | GATAAAGCTCCCACAGTTCCC (SEQ ID NO: 182) |
| MsTri8733 | TGTAAAACGACGGCCAGTTTTTCCAAACTTTCCTTCTTTTG (SEQ ID NO: 183) | AGGTACAAGCCATGATGTCCA (SEQ ID NO: 184) |
| MsTri8771 | TGTAAAACGACGGCCAGTCAACCTACGACGTTGTGGAAC (SEQ ID NO: 185) | TCATGGAGCCAGTCTTCATCT (SEQ ID NO: 186) |
| MsTri8778 | TGTAAAACGACGGCCAGTCTCTCTCTCTCTCTCTCTGCAT (SEQ ID NO: 187) | AAACACTAAAGGGTCATGCTCA (SEQ ID NO: 188) |
| MsTri8791 | TGTAAAACGACGGCCAGTTGAAGGAAGAAGGAAGAAGGAA (SEQ ID NO: 189) | ACAAGAAGAAGATTGCGACGA (SEQ ID NO: 190) |
| MsTri8831 | TGTAAAACGACGGCCAGTTGGTTATGTTGTTCCATTTTCC (SEQ ID NO: 191) | TTCAAGTAGGATAATACCATCAGA (SEQ ID NO: 192) |
| MsTri8871 | TGTAAAACGACGGCCAGTGGGAAAACTTTTGGAGAGAGC (SEQ ID NO: 193) | TGTCACTTGTTCTGGTCCTTCT (SEQ ID NO: 194) |
| MsTri8899 | TGTAAAACGACGGCCAGTCACATTCTCTTCGTGCCCTC (SEQ ID NO: 195) | CGCAGCACATGTAACTTGAAA (SEQ ID NO: 196) |
| MsTri8923 | TGTAAAACGACGGCCAGTGGCTCACAACAACAACAAAAT (SEQ ID NO: 197) | TCCGAAAAAGGTGACAGATTG (SEQ ID NO: 198) |
| MsTri8930 | TGTAAAACGACGGCCAGTTGCTTGATTATTGCTAATCGG (SEQ ID NO: 199) | CCAAACAGATCTAAAGTTCCCA (SEQ ID NO: 200) |
| MsTri8931 | TGTAAAACGACGGCCAGTCAAACAGGTGACGAGGTGAAT (SEQ ID NO: 201) | TACAGTTGCCCATACAGGAGG (SEQ ID NO: 202) |
| MsTri8949 | TGTAAAACGACGGCCAGTCGAGGACGAGTTCTGGTCAA (SEQ ID NO: 203) | TAAATGCAAGGTAGGTGGTGG (SEQ ID NO: 204) |
| MsTri8973 | TGTAAAACGACGGCCAGTCCCTGTTGAAGCTTTTGCTG (SEQ ID NO: 205) | AGGCTTGGTAGATACTCATAACAT (SEQ ID NO: 206) |
| MsTri9154 | TGTAAAACGACGGCCAGTTAATTTCATTCGCGATCACAC (SEQ ID NO: 207) | AAGACCAAGAGGAATCACCGT (SEQ ID NO: 208) |
| MsTri9161 | TGTAAAACGACGGCCAGTACCCCCTTCAAAACCCTATCT (SEQ ID NO: 209) | TACAGGTTGGGAATCAGGTTG (SEQ ID NO: 210) |
| MsTri9223 | TGTAAAACGACGGCCAGTCCGCCTCAAATAGTTATAAACTTC (SEQ ID NO: 211) | TGAATGTGAGGAAGTGGGTTT (SEQ ID NO: 212) |
| MsTri9225 | TGTAAAACGACGGCCAGTCGAACAAGACGAAGAAGATGC (SEQ ID NO: 213) | GATGATGACGAGGACGAAAGA (SEQ ID NO: 214) |
| MsTri9303 | TGTAAAACGACGGCCAGTACAACAAGGGAAAGCATAGCA (SEQ ID NO: 215) | CTTCATCCTCCTCTTGCTCCT (SEQ ID NO: 216) |
| MsTri9326 | TGTAAAACGACGGCCAGTGGTTTCGCTTGGAATTCTGAT (SEQ ID NO: 217) | AGTACTATTGCAATGGCGTGG (SEQ ID NO: 218) |

TABLE 1-continued

Alfalfa trichome EST-SSRs used to genotype the
608Altet4 and NECS141Altet4 mapping populations.

| Primer | Forward | Reverse |
|---|---|---|
| MsTri9329 | TGTAAAACGACGGCCAGTTTGGCTTTGATTGCTTCAACT (SEQ ID NO: 219) | ATCAAGATCGACTGAACCACG (SEQ ID NO: 220) |
| MsTri9367 | TGTAAAACGACGGCCAGTGCACATGACAAGAGGACTAAGC (SEQ ID NO: 221) | ACAACATTTCCTCCACCATGA (SEQ ID NO: 222) |
| MsTri9445 | TGTAAAACGACGGCCAGTCAACAATGCTGCAAATGAAAG (SEQ ID NO: 223) | TCCAACTCCTCTTGGTTTTTG (SEQ ID NO: 224) |
| MsTri9455 | TGTAAAACGACGGCCAGTCTCCATCAACTGGTTCACCG (SEQ ID NO: 225) | CACACATCAAAGCCCCTAAAA (SEQ ID NO: 226) |
| MsTri9475 | TGTAAAACGACGGCCAGTCCAAACCCTAGGAGTCTGAGGT (SEQ ID NO: 227) | TGCATGTAATATCTATCTTTGGAA (SEQ ID NO: 228) |
| MsTri9544 | TGTAAAACGACGGCCAGTCAACACAATCATTTTGGGAGC (SEQ ID NO: 229) | ATTTTTCCACTTCTGGTGGGA (SEQ ID NO: 230) |
| MsTri9739 | TGTAAAACGACGGCCAGTAGTATGGTGGCAGAGGCAAG (SEQ ID NO: 231) | AGAGAAACGTTCTGTTTGGCA (SEQ ID NO: 232) |
| MsTri9744 | TGTAAAACGACGGCCAGTAAAGGAAGGGTCTTTATCGAGAG (SEQ ID NO: 233) | GGGTTCTGTTCCAAACAGTGA (SEQ ID NO: 234) |
| MsTri9764 | TGTAAAACGACGGCCAGTTCTCTCTGATAATAATTCTTTGAA (SEQ ID NO: 235) | ATCTCTTAGCCTCGTTGGCTC (SEQ ID NO: 236) |
| MsTri9765 | TGTAAAACGACGGCCAGTAAGATAAAATAATTGAATCGGTTG (SEQ ID NO: 237) | ATCTCTTAGCCTCGTTGGCTC (SEQ ID NO: 238) |
| MsTri9803 | TGTAAAACGACGGCCAGTTGCTGTAGCTTTGAACTTGTGA (SEQ ID NO: 239) | CGAGAAAATTAATATCACTCTGAA (SEQ ID NO: 240) |
| MsTri9820 | TGTAAAACGACGGCCAGTCCTGATGGTCATCACTAAGCC (SEQ ID NO: 241) | TCTTGTTGATATAATCTACGGAA (SEQ ID NO: 242) |
| MsTri9839 | TGTAAAACGACGGCCAGTACAGCGACAGCAGCGACACT (SEQ ID NO: 243) | CAGGTACGTGAAAACTCCCAA (SEQ ID NO: 244) |
| MsTri9849 | TGTAAAACGACGGCCAGTTTTCAAATCCAAGTGGTGGAG (SEQ ID NO: 245) | TGAGGCTTAACCTTAGGAGGC (SEQ ID NO: 246) |
| MsTri9857 | TGTAAAACGACGGCCAGTTTTGATAAACCAATCTCCCACA (SEQ ID NO: 247) | GGGACCCAATAACCGAAAATA (SEQ ID NO: 248) |
| MsTri9943 | TGTAAAACGACGGCCAGTCAGGGTTACCAGAAGGGTCAC (SEQ ID NO: 249) | ACGTGTAGCACTGCTTGTTTT (SEQ ID NO: 250) |

PCR primers that amplify genes involved in the aluminum tolerance response were evaluated as candidate markers for QTL mapping. These genes are involved in organic acid synthesis (malate dehydrogenase, aluminum-activated malate transporter (ALMT), citrate synthase, citrate dehydrogenase, isocitrate dehydrogenase, oxalate oxidase, superoxide dismutase, acid phosphatases, peroxidases), signal transduction pathways, oxidative stress (phosphoenolpyruvate carboxylase, PEPC), and transporters (Ermolayev et al., 2003; Maron et al., 2008; Tesfaye et al., 2001). Additional gene targets for marker development include aluminum tolerance gene loci identified from transcript profiling in *Medicago truncatula* (Chandran et al., 2008).

SSR amplicons were scored using GeneMapper 3.7 software. PCR products of altolerance genes were analyzed for length polymorphisms and/or sequenced with the BigDye® terminator v3.1 cycle sequencing kit and potential SNPs (single nucleotide polymorphisms) were identified using an ABI3730 genetic analyzer. A total of 576 polymorphic SSR primers pairs were used for genotyping.

Example 5

Creating Linkage Groups (LGs)

Polymorphic amplicons segregating in the populations were scored using the TetraploidMap program (Hackett et al, 2001) as described by Hacket and Luo (2003). Simplex (1:1), duplex (5:1), and double simplex (3:1) markers were scored based on segregation ratio on the population to achieve maximum resolution on the parental linkage map. Recombination frequencies and clustering of markers into linkage groups (LGs) was performed using the software TetraploidMap (Hackett et al., 2001) previously used in alfalfa (Julier et al., 2003; Robins et al., 2008; Robins et al., 2007). MapChart (Voorrips, 2002) was used to draw the resulting LGs.

Example 6

QTL Analysis

One-way analysis of variance for the average relative callus growth ratio (−Al/+Al) and all genotyped markers was performed using the ANOVA module in TetraploidMap to find molecular markers with relevance to aluminum tolerance. The non-parametric Kruskal-Wallis test for significant differences between the group medians as originally described by Siegel (1956) was also performed using the ANOVA module in TetraploidMap.

The interval mapping strategy for autotetraploid species described by (Hackett et al., 2001) was implemented for QTL analysis. The TetraploidMap software program was used for all analytical procedures for the QTL interval mapping. Multiple regression analysis for each of the identified QTLs was performed to determine the allelic effect at each QTL.

Example 7

Evaluation of Aluminum Tolerance Using the Callus Assay

Calli were grown in Blaydes callus induction medium and tested for aluminum tolerance according to the methods described in Example 2. Calli from the Altet1 through Altet4 genotypes and the (aluminum-sensitive) CUF101-derived genotypes 95-608 and 95-653 were evaluated. The relative growth rate of calli from Altet4 in media +Al vs. media −Al was consistently higher than any other genotype evaluated, including the other tetraploid genotypes (FIG. 1). Genotype 95-608 had the lowest relative growth rate among the genotypes evaluated and was consistently the most aluminum-sensitive germplasm.

As described above, the mapping populations 608Altet4 and NECS141Altet4 were derived from separate crosses of the aluminum-tolerant genotype Altet4 to each of the Al-susceptible 95-608 and NECS141 genotypes, respectively. The aluminum tolerance of both mapping populations and the parent genotypes was also tested using the methods described in Example 2.

Figure 2:
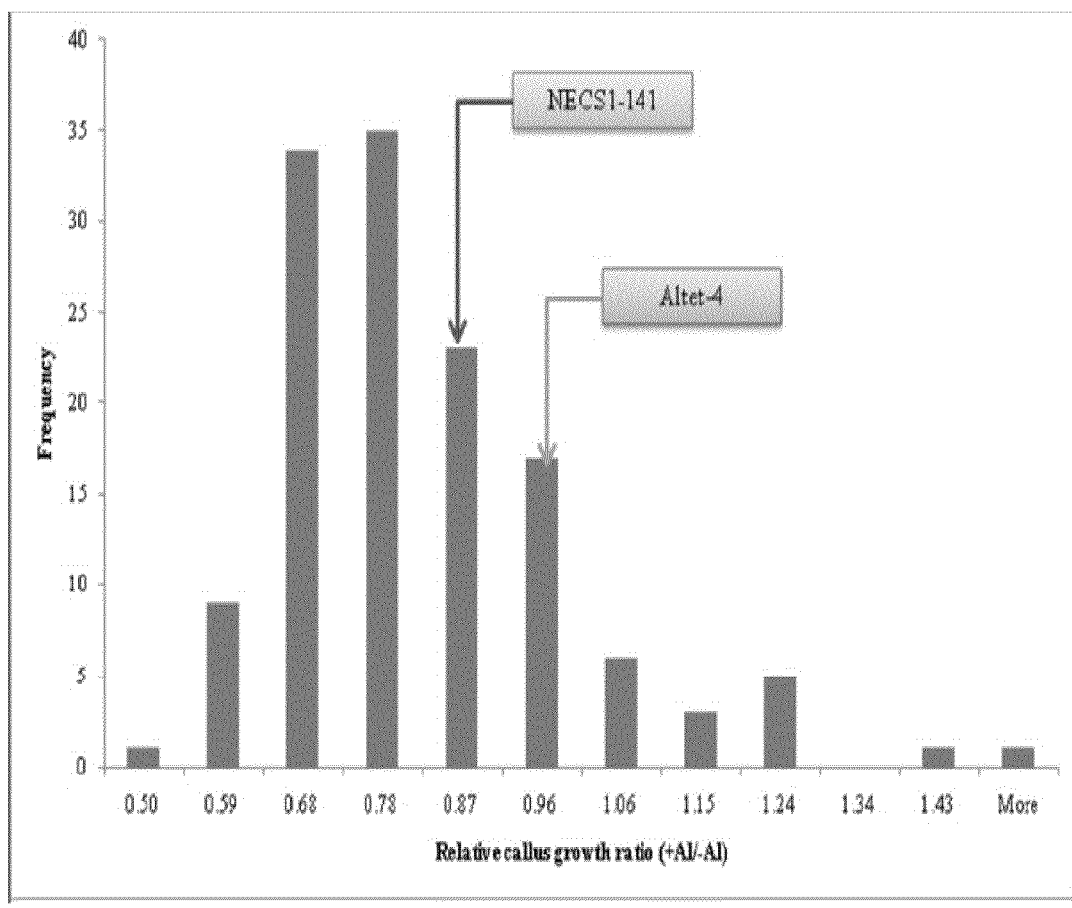
FIG. 2: Distribution of an aluminum-tolerant phenotype of the NECS141Altet4 mapping population. The phenotype graphed is the relative callus growth ratio at 8 weeks of growth in the callus bioassay.

In the experimental replicate shown in FIG. 2, the relative growth rate values from the callus bioassay were 0.87 and 0.96 for the NECS141 and Altet4 parents, respectively. The aluminum tolerance phenotypes in the NECS141Altet4 population, assessed using the callus bioassay, exhibited a continuous and normal distribution consistent with polygenic inheritance (FIG. 2). The relative growth rates of the progeny ranged from 0.5 to >1.4, indicating transgressive segregation for aluminum tolerance in this population as well. Transgressive segregation of the aluminum tolerant phenotype among the mapping population demonstrates that both the NECS141 and Altet4 parents are contributing positive alleles for aluminum tolerance.

Figure 3:
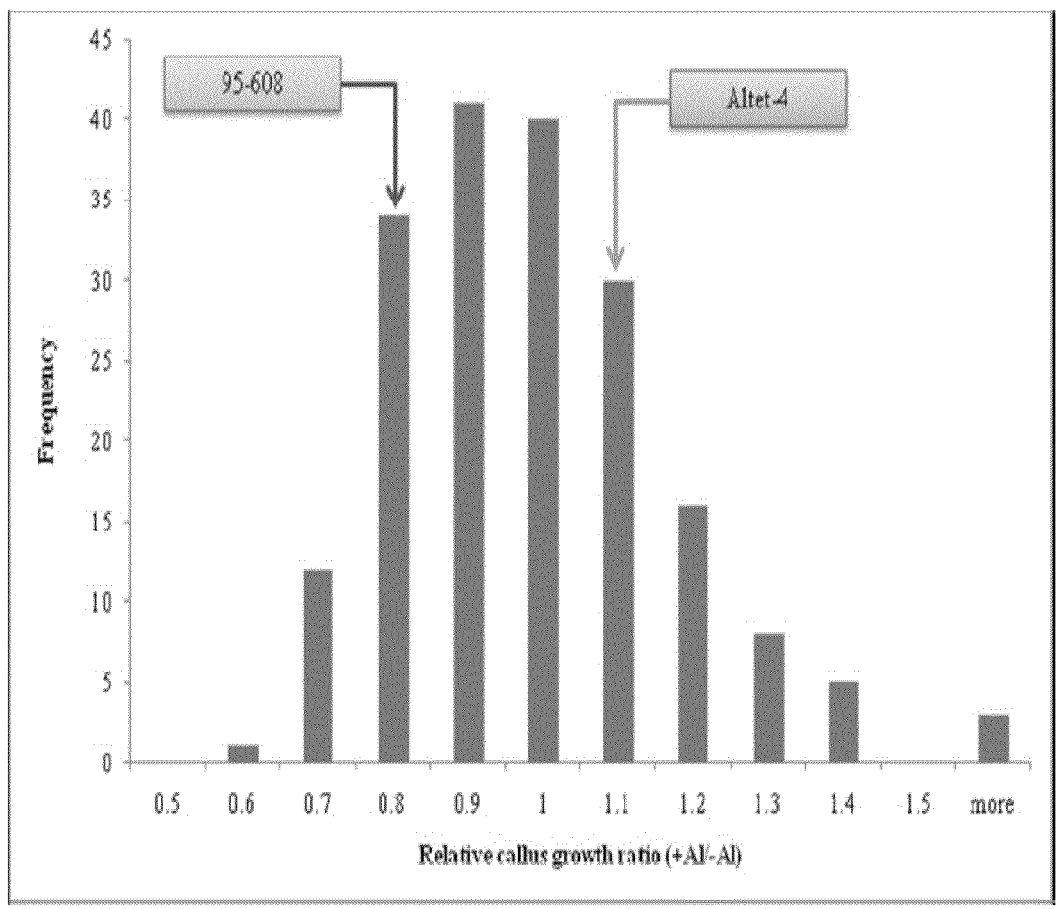
FIG. 3: Distribution of an aluminum-tolerant phenotype of the 608Altet4 mapping population. The phenotype graphed is the relative callus growth ratio at 8 weeks of growth in the callus bioassay.

In the experimental replicate shown in FIG. 3, the relative growth rate values from the callus bioassay were 0.8 and 1.1 for the 95-608 and Altet4 parents, respectively. The aluminum tolerance phenotypes in the 608Altet4 population, assessed using the callus bioassay, exhibited a continuous and normal distribution consistent with polygenic inheritance (FIG. 3). The relative growth rates of the progeny ranged from 0.5 to >1.5 indicating transgressive segregation for aluminum tolerance in this population and confirming the ability of the callus assay to detect quantitative differences in aluminum tolerance. Transgressive segregation of the phenotype among the mapping population demonstrates that both the 95-608 and Altet4 parents are contributing positive alleles for aluminum tolerance.

Example 8

Evaluation of Aluminum Tolerance Using the Whole-Plant Culture Media Assay

Figure 4:
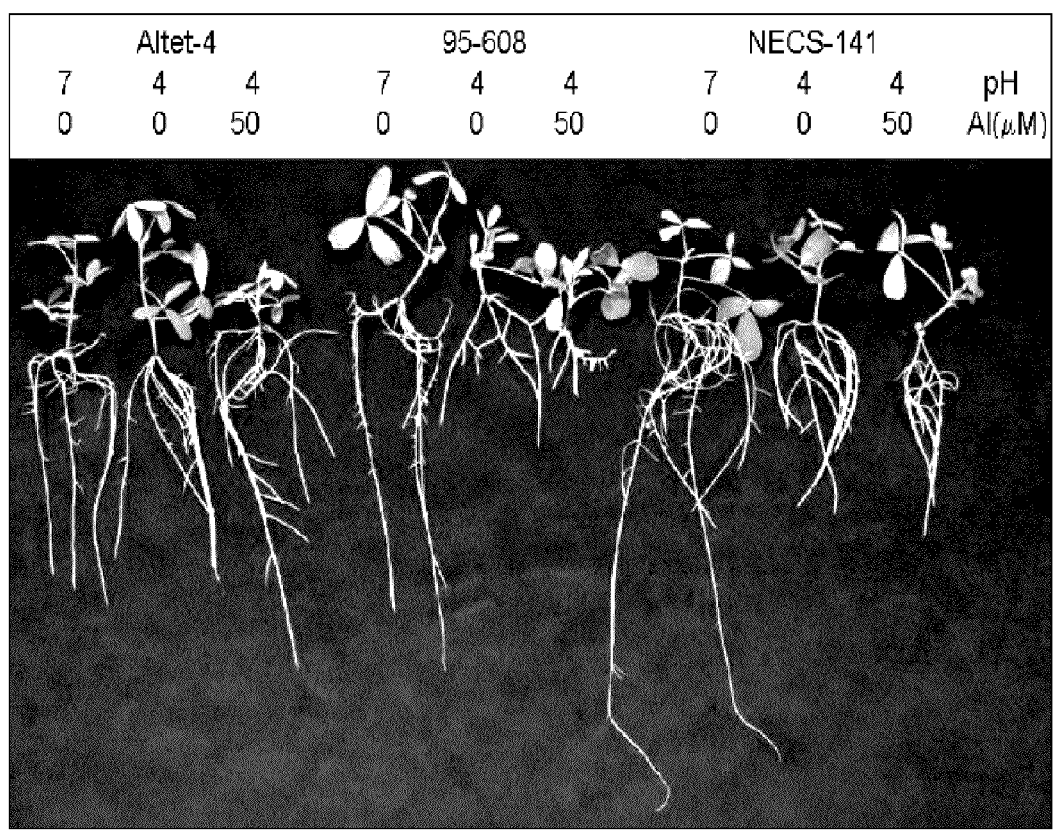
FIG. 4: Phenotypes of three genotypes of tetraploid alfalfa after 18 days of growth in the whole-plant culture media assay.
Figure 5A:
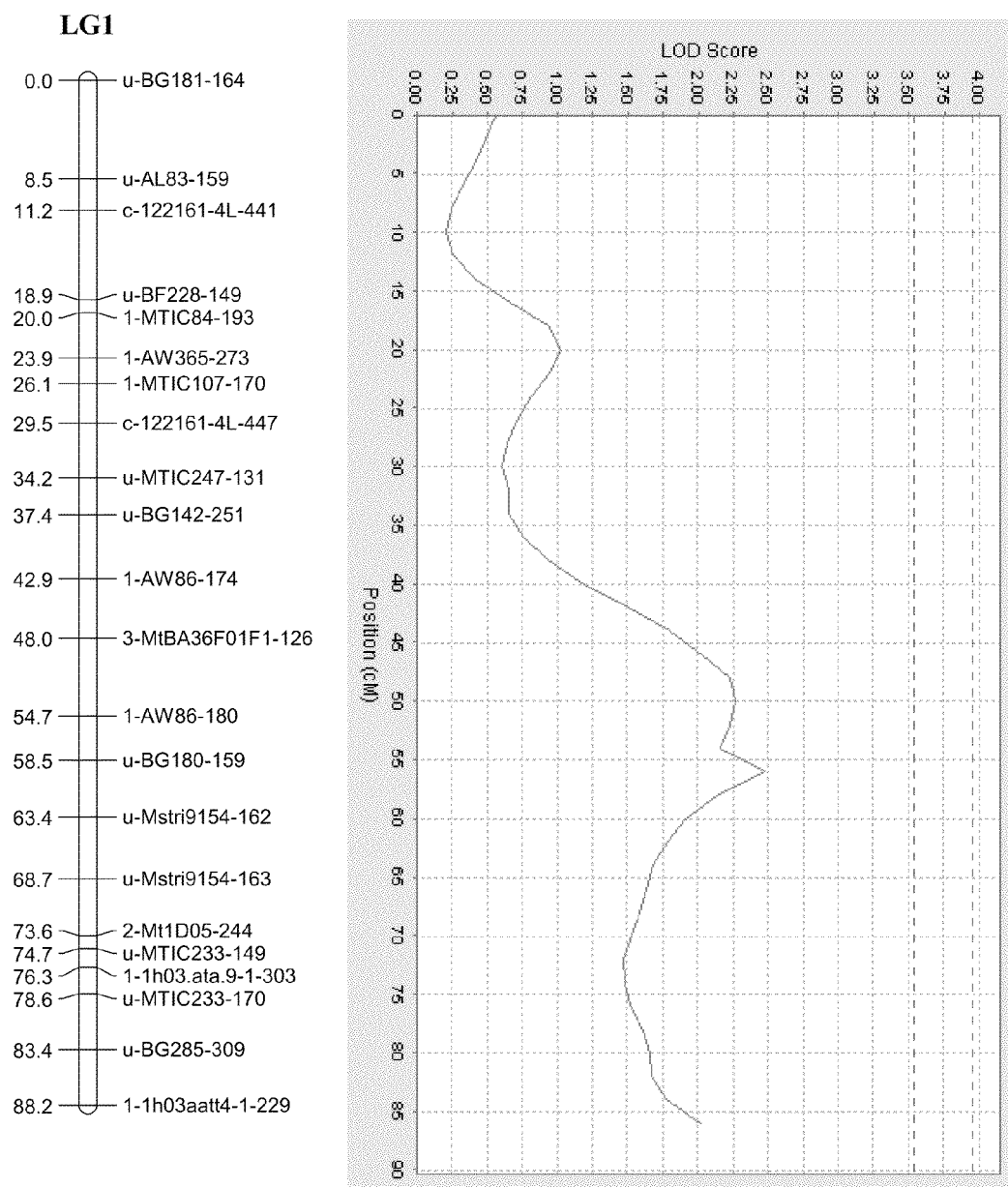
FIGS. 5A, 5B, 5C, 5D: Composite linkage map and LOD plot of aluminum tolerance QTL identified in Altet4. (5A) Tetraploid alfalfa composite LG (linkage group) 1. Maximum LOD=2.5 at 56 cM. Percent phenotypic variation explained ($R^2$)=10.413. (5B) Tetraploid alfalfa composite LG4. Maximum LOD=2.06 at 0 cM. Percent phenotypic variation explained ($R^2$)=4.34. (5C) Tetraploid alfalfa composite LG5. Maximum LOD=2.79 at 26 cM. Percent phenotypic variation explained ($R^2$)=7.8. (5D) Tetraploid alfalfa composite LG8. Maximum LOD=2.28 at 46 cM. Percent phenotypic variation explained ($R^2$)=7.1.
Figure 5B:
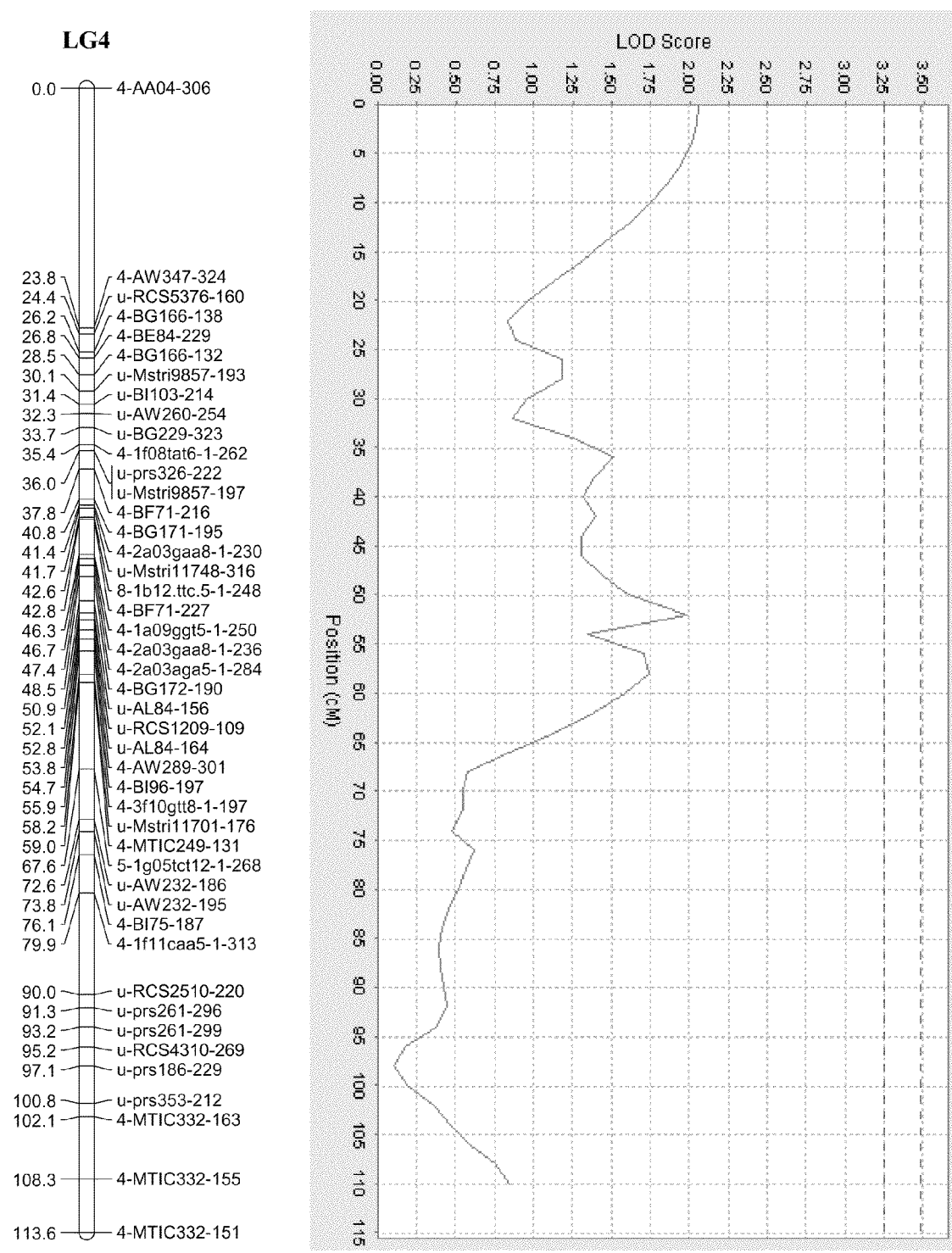
Figure 5C:
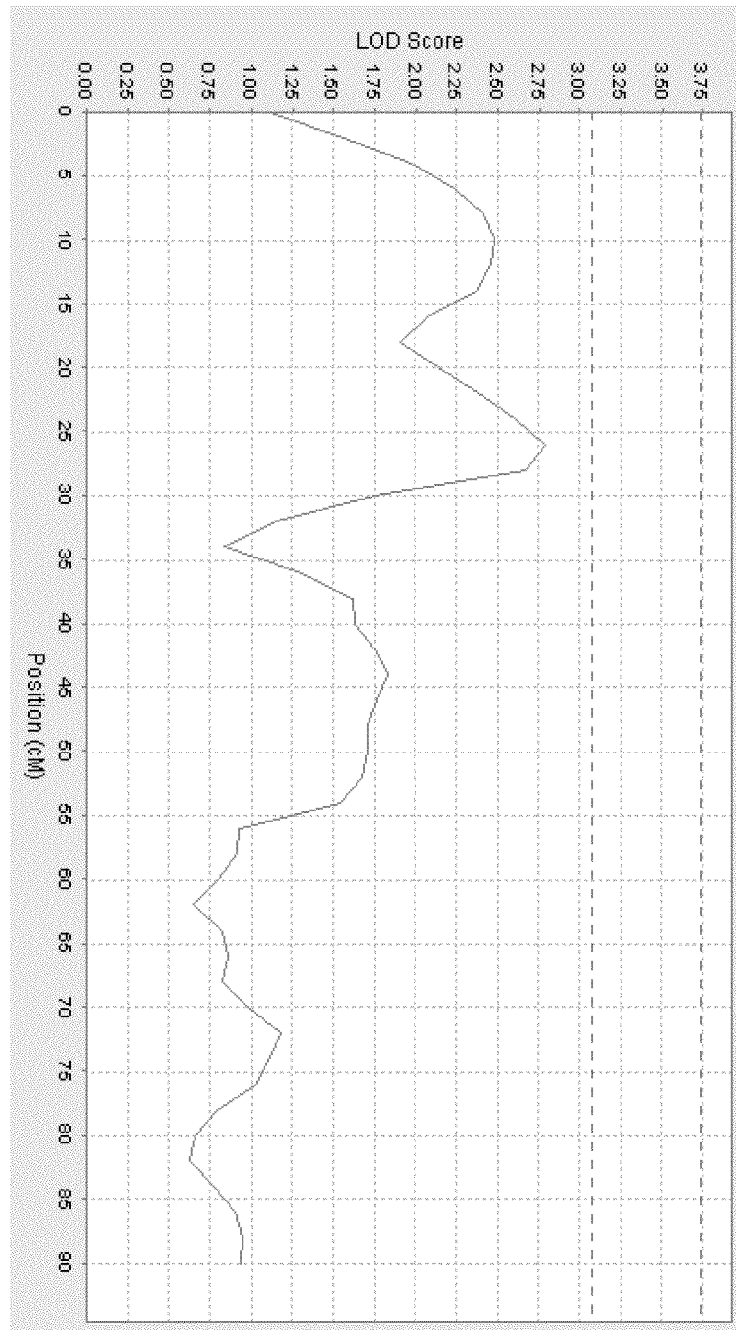
Figure 5D:
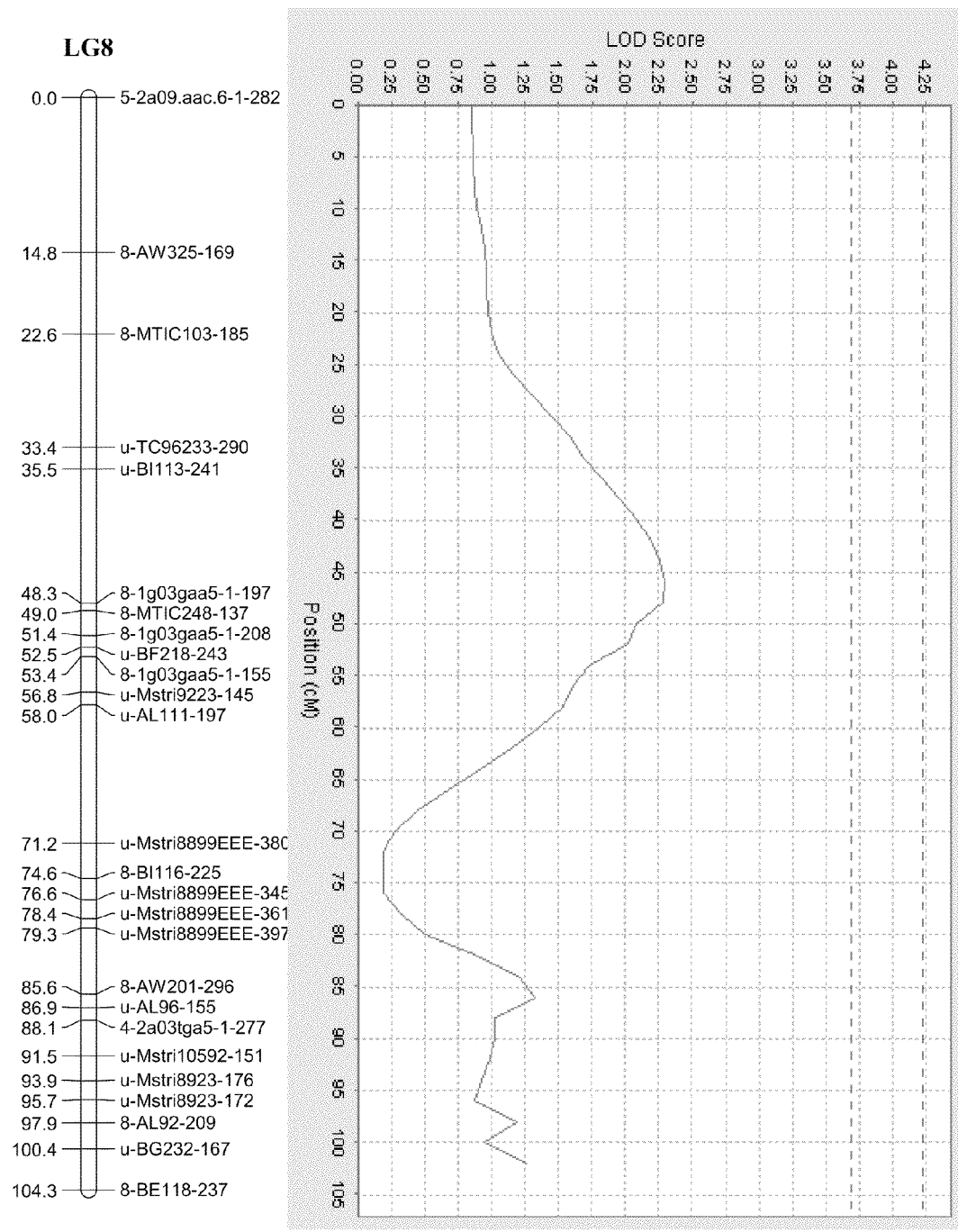
Figure 6A:
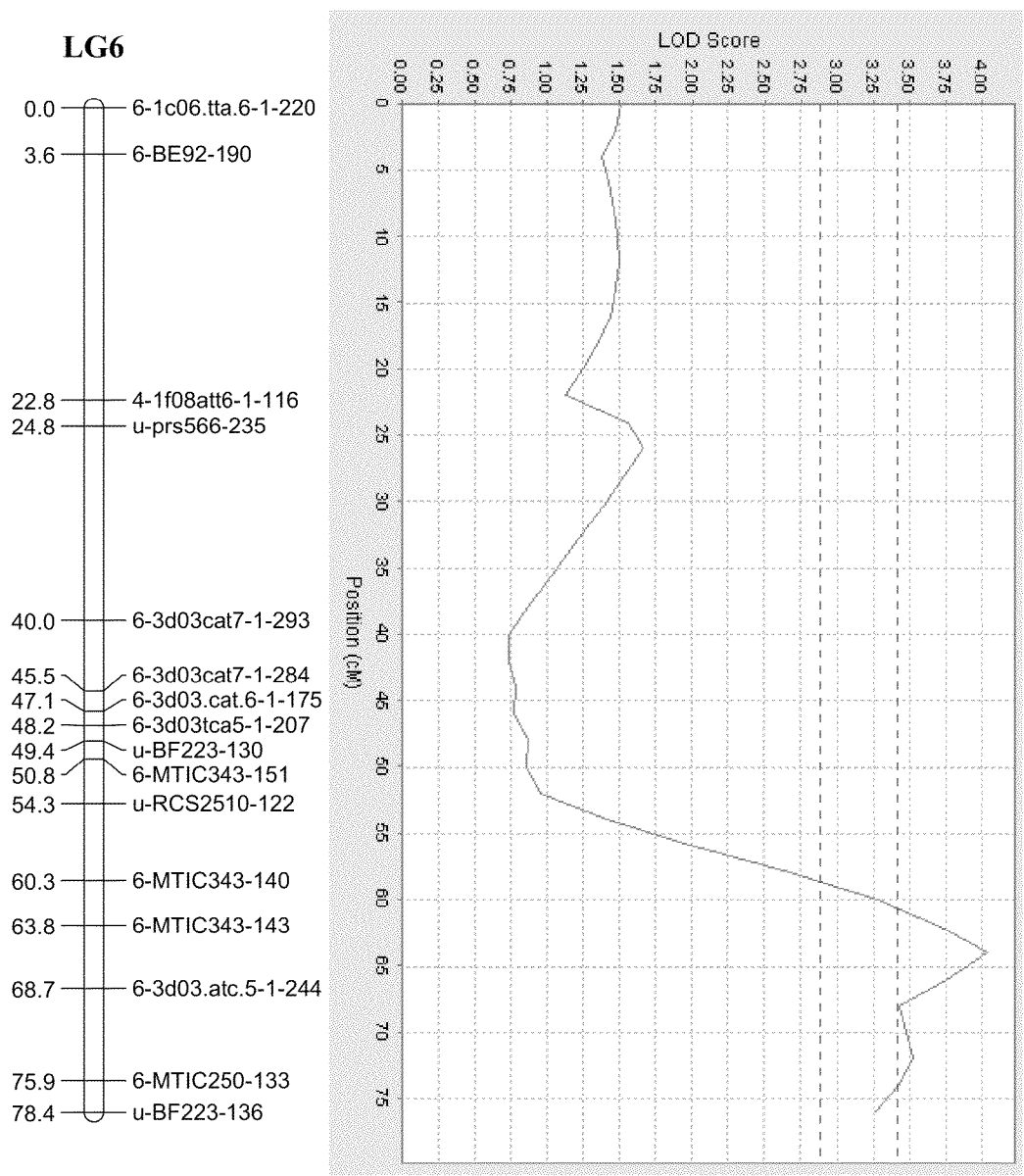
FIGS. 6A, 6B: Composite linkage map and LOD plot of aluminum tolerance QTL identified in NECS141. (6A) Tetraploid alfalfa composite LG6. Maximum LOD=4.30 at 64 cM. Percent phenotypic variation explained ($R^2$)=12.1. (6B) Tetraploid alfalfa composite LG2. Maximum LOD=3.19 at 56 cM. Percent phenotypic variation explained ($R^2$)=8.9.
Figure 6B:
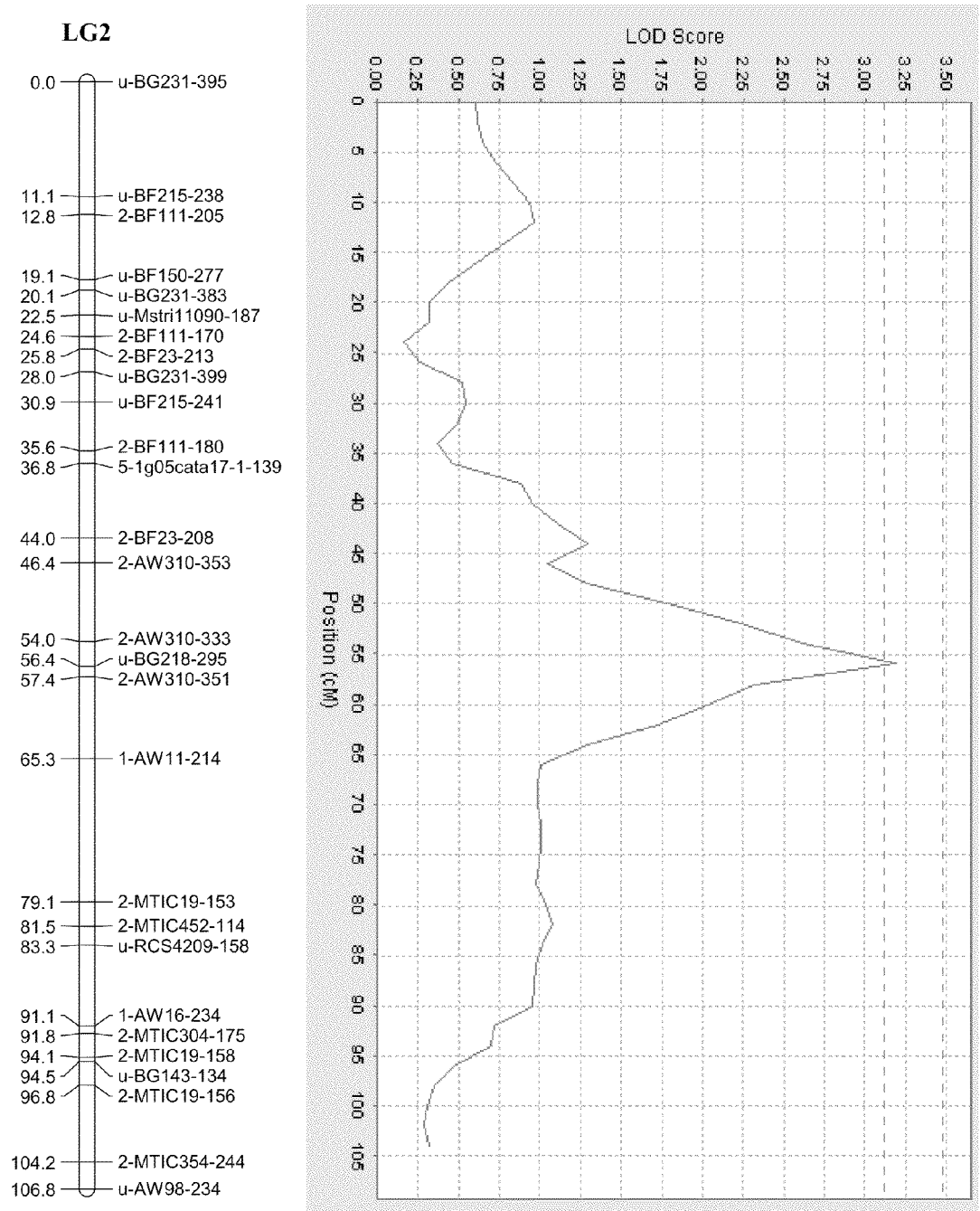

Using the methods described in Example 3, the root growth and length of the Altet4, NECS141 and 95-608 genotypes were evaluated. The root growth and length of the Altet4 genotype was consistent in the three growing conditions regardless of acidity (pH=7.0, pH=4.0) and presence or absence of aluminum in the growth media (FIG. 4). In contrast, the root growth of the aluminum susceptible genotypes was reduced in low pH/+Al, when compared to the control conditions at pH=7.0/−Al.

After 5 days of growth in the whole plant culture media assay, we observed an increase in the pH of the growth media in which Altet4 was grown vs. no change in pH of the growth media of 95-608 and without any plant (data not shown).

Example 9

Evaluation of Aluminum Tolerance in Plants Grown in Soil $Al^{+3}$ becomes soluble in soil solutions at low pH (acidic conditions); at higher pH, $Al^{+3}$ becomes less soluble in the soil solution and therefore less bioavailable to cause toxic effects in plants. Lime is a frequently-used agricultural amendment which increases soil pH. In these experiments, the ratio of root dry matter in soils in which the amount of $Al^{+3}$ is available to the plant is varied (g of growth in unlimed soil/g of growth in limed soil) was assessed.

Soil-based assays using plants grown in a greenhouse were performed at the University of Georgia (Athens, Ga.). Forty-eight cuttings per genotype were used in this experiment. The cuttings were taken 30 to 40 days before setting up the experimental conditions after which time they were transferred to soil either with or without lime and allowed to grow for 8 weeks. Samples were then washed and root and shoot length measurements were obtained. Fresh root and shoot tissues were placed in dryers at 60° C. for 72 hours and measurements for root dry matter (DMr), shoot dry matter (DMs), total root length (Lr), and total shoot length (Ls) were obtained. The ratios between the corresponding growth (shoot and root) in unlimed and limed soil were calculated and analyzed.

The experimental design was a split-plot design where the main plot was the type of soil and sub-plots were the genotypes. In addition, within each main plot (limed or unlimed soil) the genotypes were randomized in both dimensions recreating a latin square design within each type of soil. Every latin square is comprised of four columns and four rows and therefore, four cuttings per genotype were used within every type of soil. Six replications were used in the experiment. The ratios for every genotype were calculated as a randomized complete block design with four entries per genotype per replication.

TABLE 2

Soil analyses for unlimed and limed soil.

| Lab | Sample | LBC[1] (ppm CaCO$_3$/ pH) | pH CaCl2[2] | Equiv. water pH | % Base Saturation | meq/100 g CEC |
|---|---|---|---|---|---|---|
| 78134 | Unlimed | 628 | 4.27 | 4.87 | 21.07 | 3.87 |
| 78135 | Unlimed | 607 | 4.27 | 4.87 | 20.33 | 3.70 |
| 77702 | Limed | 476 | 6.64 | 7.24 | 99.19 | 7.02 |
| 77703 | Limed | 466 | 6.66 | 7.26 | 99.55 | 8.25 |

TABLE 3

Soil analysis for limed and unlimed soil

| | | mg/kg (ppm) | | | | | | | | | | | | | | |
|---|---|---|---|---|---|---|---|---|---|---|---|---|---|---|---|---|
| Lab | Sample | Al | Ca | Cd | Cr | Cu | Fe | K | Mg | Mn | Mo | Na | Ni | P | Pb | Zn |
| 78134 | Unlimed | 202.0 | 90.25 | <0.01 | 0.06 | 0.24 | 17.34 | 24.28 | 29.04 | 5.89 | 0.06 | 13.59 | <0.05 | 2.18 | 0.97 | 1.19 |
| 78135 | Unlimed | 195.8 | 82.01 | <0.01 | <0.03 | 0.20 | 15.48 | 21.92 | 27.40 | 5.39 | <0.03 | 13.43 | <0.05 | 1.33 | 0.96 | 0.92 |
| 77702 | Limed | 212.6 | 948 | <0.01 | 0.05 | 6.52 | 12.54 | 431.7 | 127.2 | 10.28 | 0.11 | 12.66 | <0.05 | 122.7 | 1.57 | 3.81 |
| 77703 | Limed | 224.6 | 1123 | <0.01 | 0.11 | 2.10 | 12.57 | 459.5 | 160.2 | 9.75 | 0.22 | 19.14 | <0.05 | 145.5 | 1.83 | 4.23 |

TABLE 4

Comparison of plant growth parameters soil based assay with whole plant assay in culture media

| Genotype | Soil-based assay† | Whole plant assay in culture media‡ |
|---|---|---|
| 95-608 | 0.536 | 0.56 |
| NECS141 | 0.313 | 0.52 |
| Altet4 | 0.714 | 0.97 |

†Ratio of root dry matter (g of growth in unlimed soil/g of growth in limed soil)
‡Ratio of total root length (pH = 7-aluminum/pH = 4 + Al; Al$^{+3}$ at 50 μM)

The ranking of Altet4 (tolerant) vs. NECS141 and 95-608 (susceptible) from these experiments (Table 4) is in agreement with the classification of tolerant vs. susceptible obtained using tissue culture and whole plant assay in media (FIG. 3, 4).

Example 10

Construction of Genetic Maps of the Altet4 and 95-608 Genotypes

Figure 7:
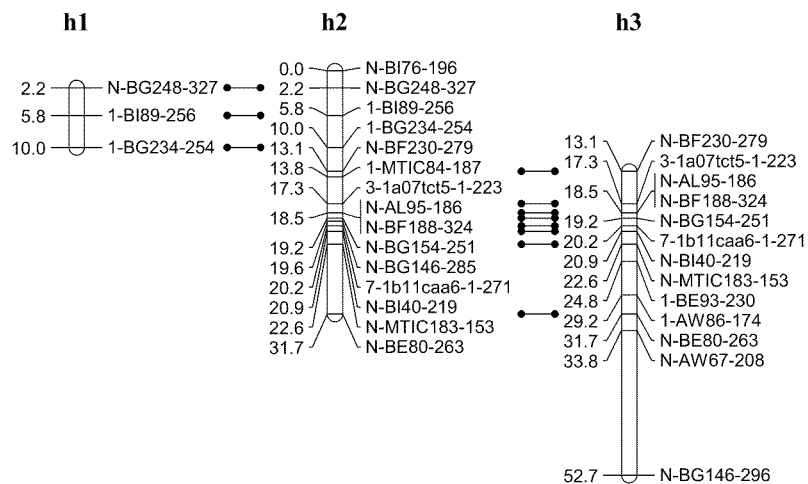
FIG. 7: Genetic map of the linkage groups of the Altet4 genotype constructed from the cross between Altet4 and 95-608. Linkage groups are denoted by "LG" followed by a number, e.g., LG1 is linkage group 1. Homeologous chromosomes are indicated by "h" followed by a number, e.g., h2 is chromosome number 2 out of the four homeologous chromosomes of a given linkage group.
Figure 7:
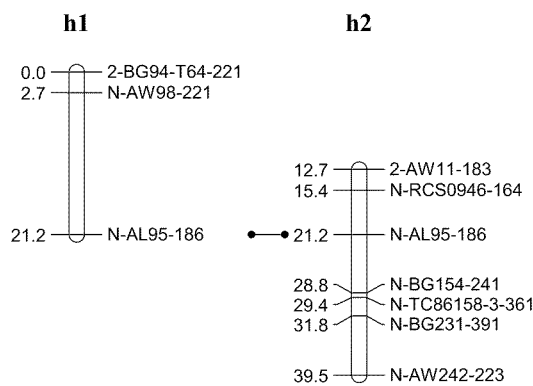
Figure 7:
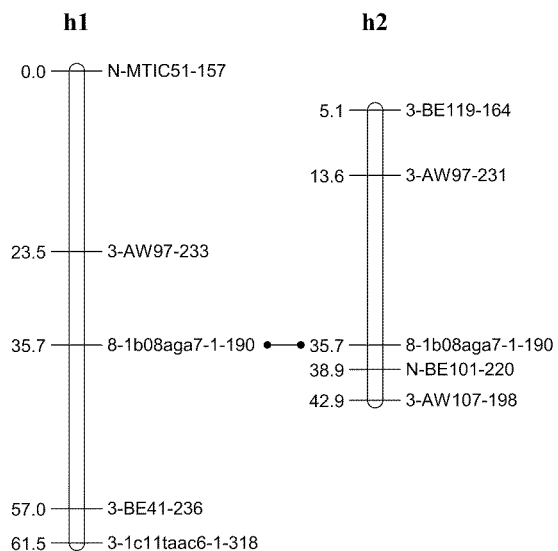
Figure 7:
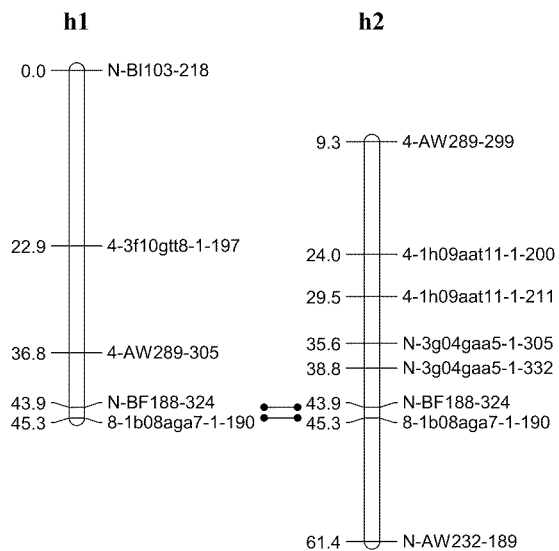
Figure 7:
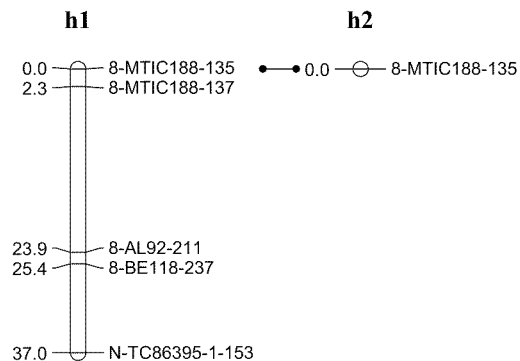
Figure 8:
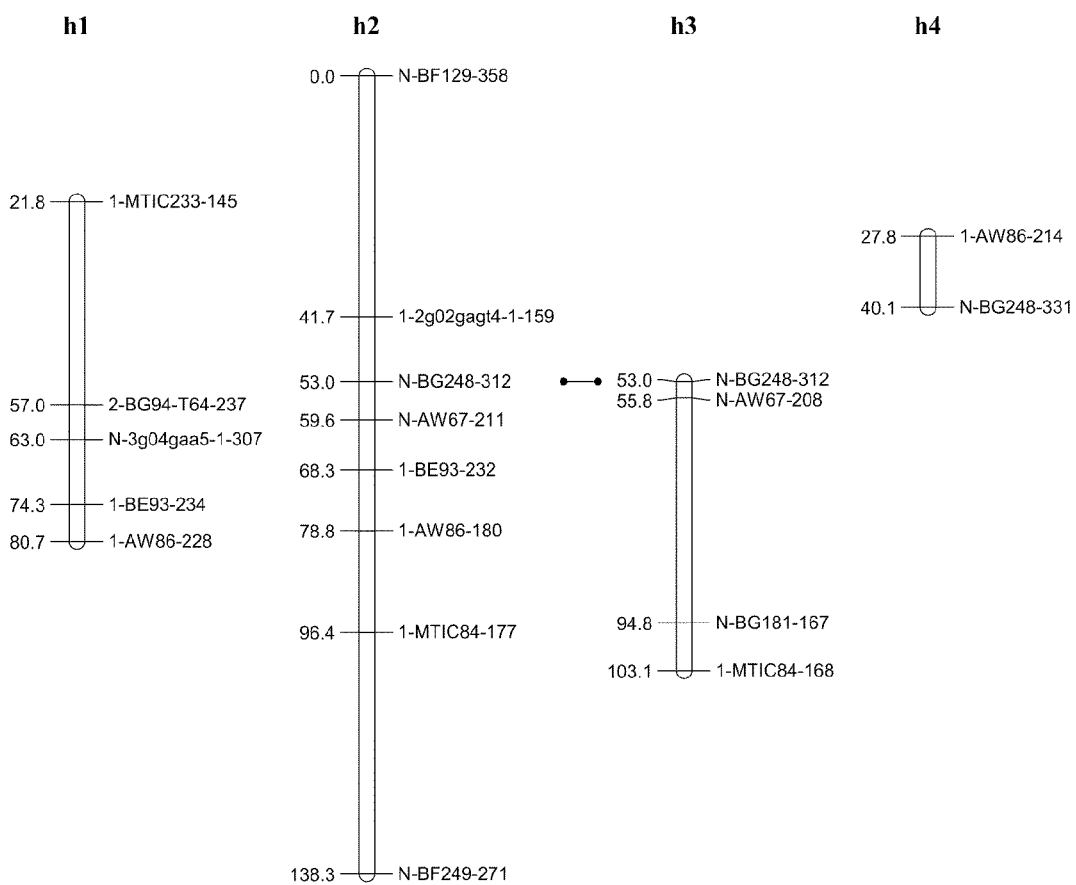
FIG. 8: Genetic map of the linkage groups of the 95-608 genotype constructed from the cross between Altet4 and 95-608. Linkage groups are denoted by "LG" followed by a number, e.g., LG1 is linkage group 1. Homeologous chromosomes are indicated by "h" followed by a number, e.g., h2 is chromosome number 2 out of the four homeologous chromosomes of a given linkage group.
Figure 8:
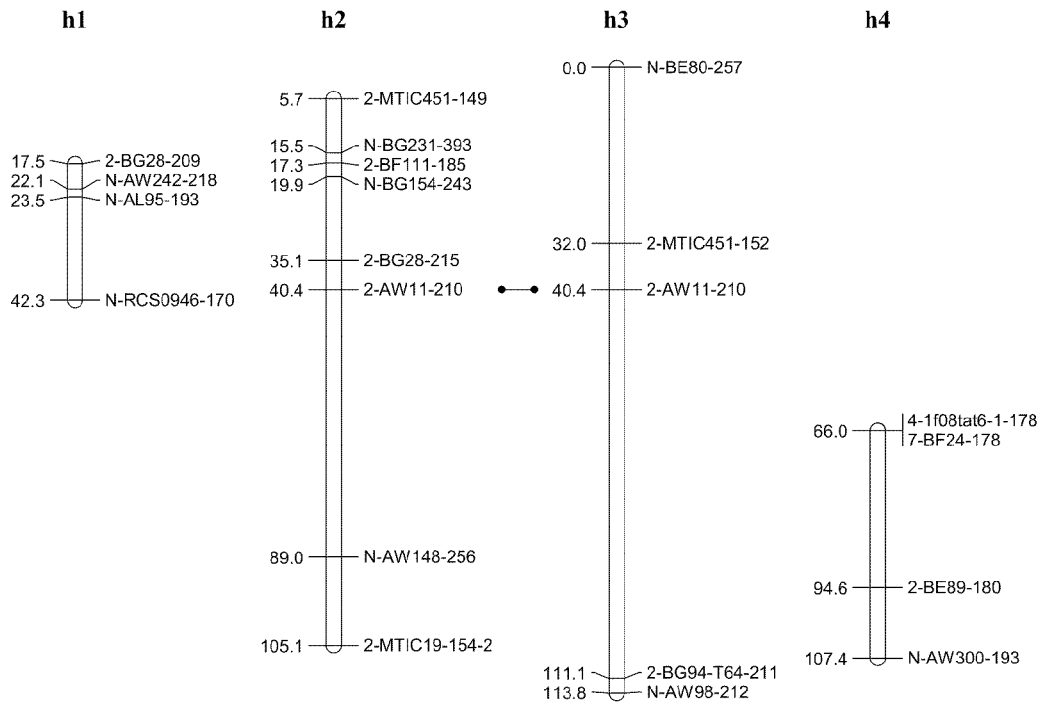
Figure 8:
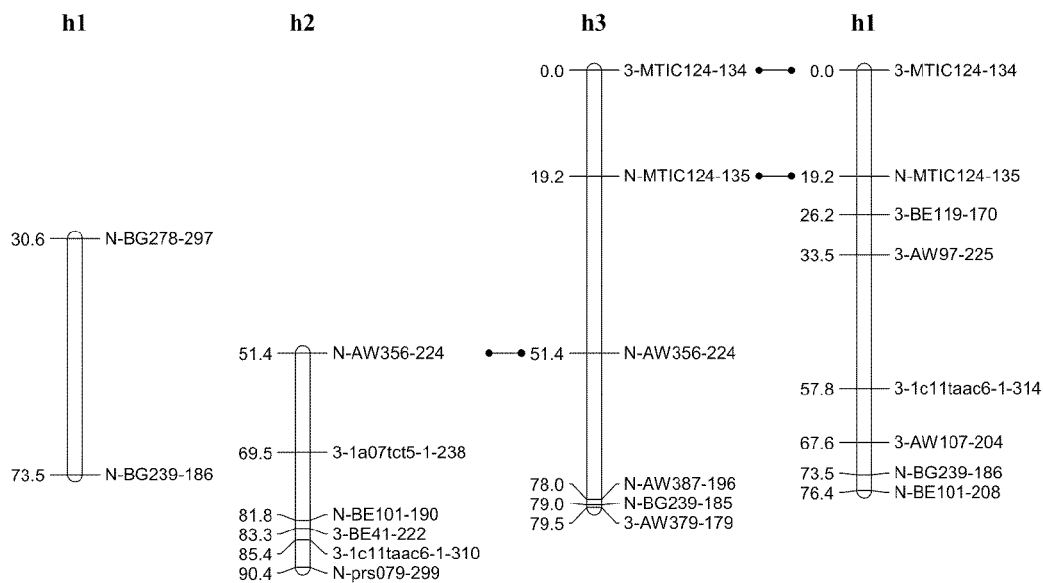
Figure 8:
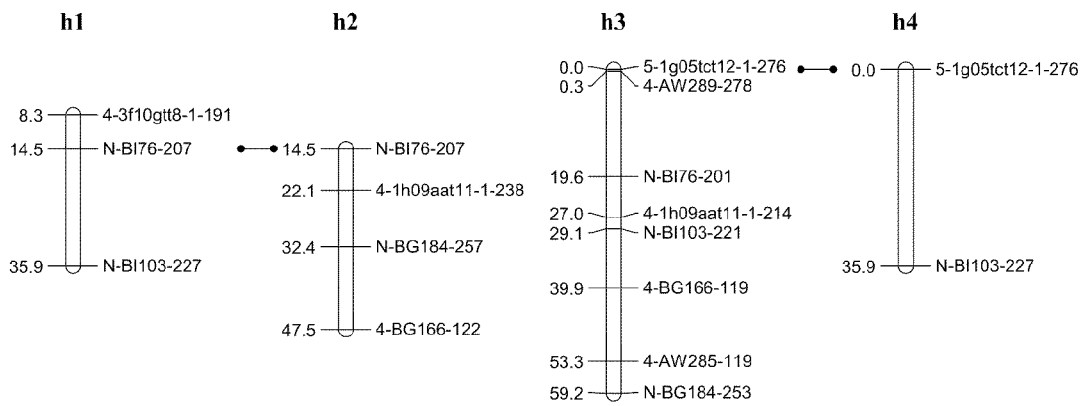
Figure 8:
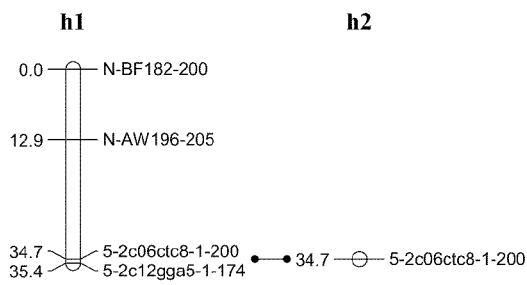
Figure 8:
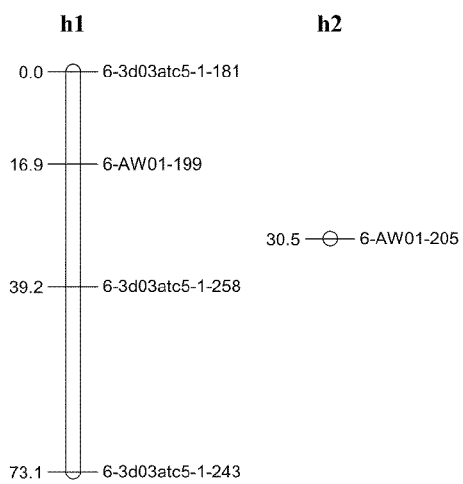
Figure 8:
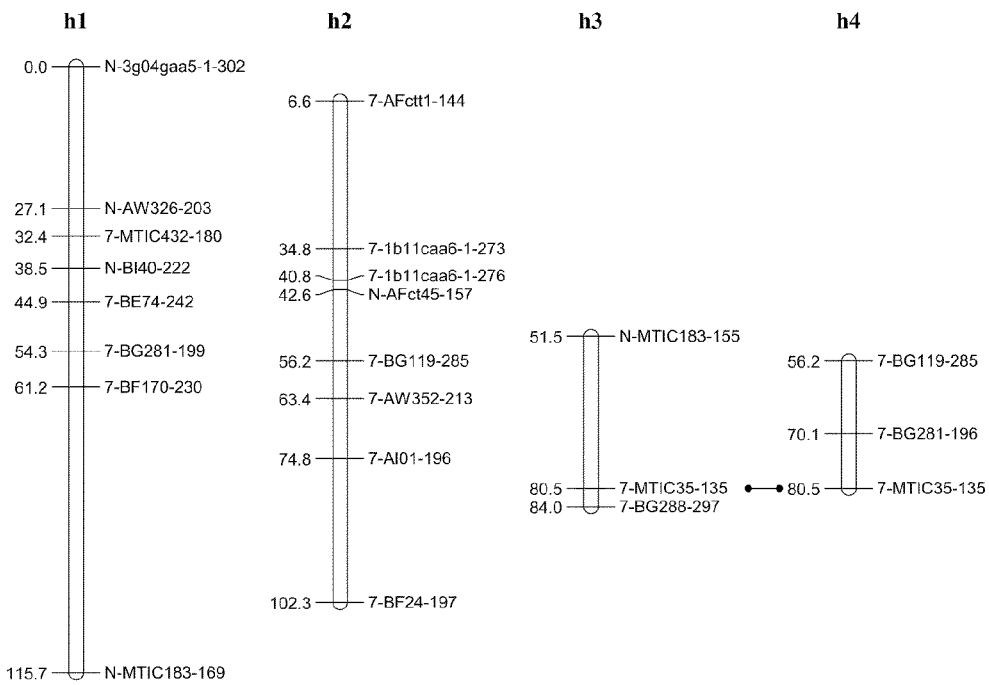
Figure 8:
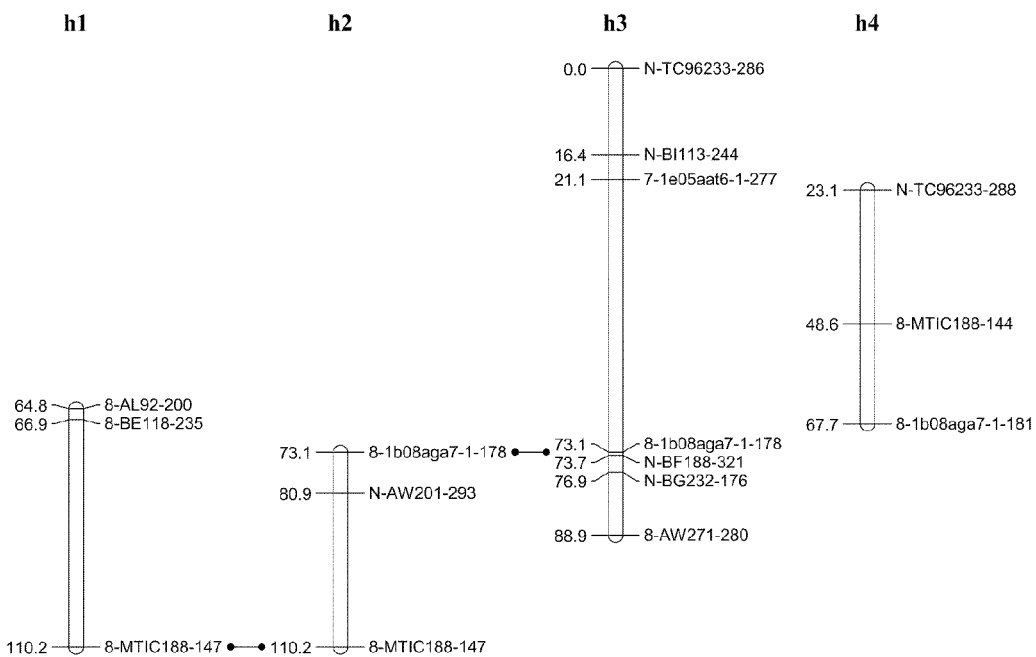
Figure 9:
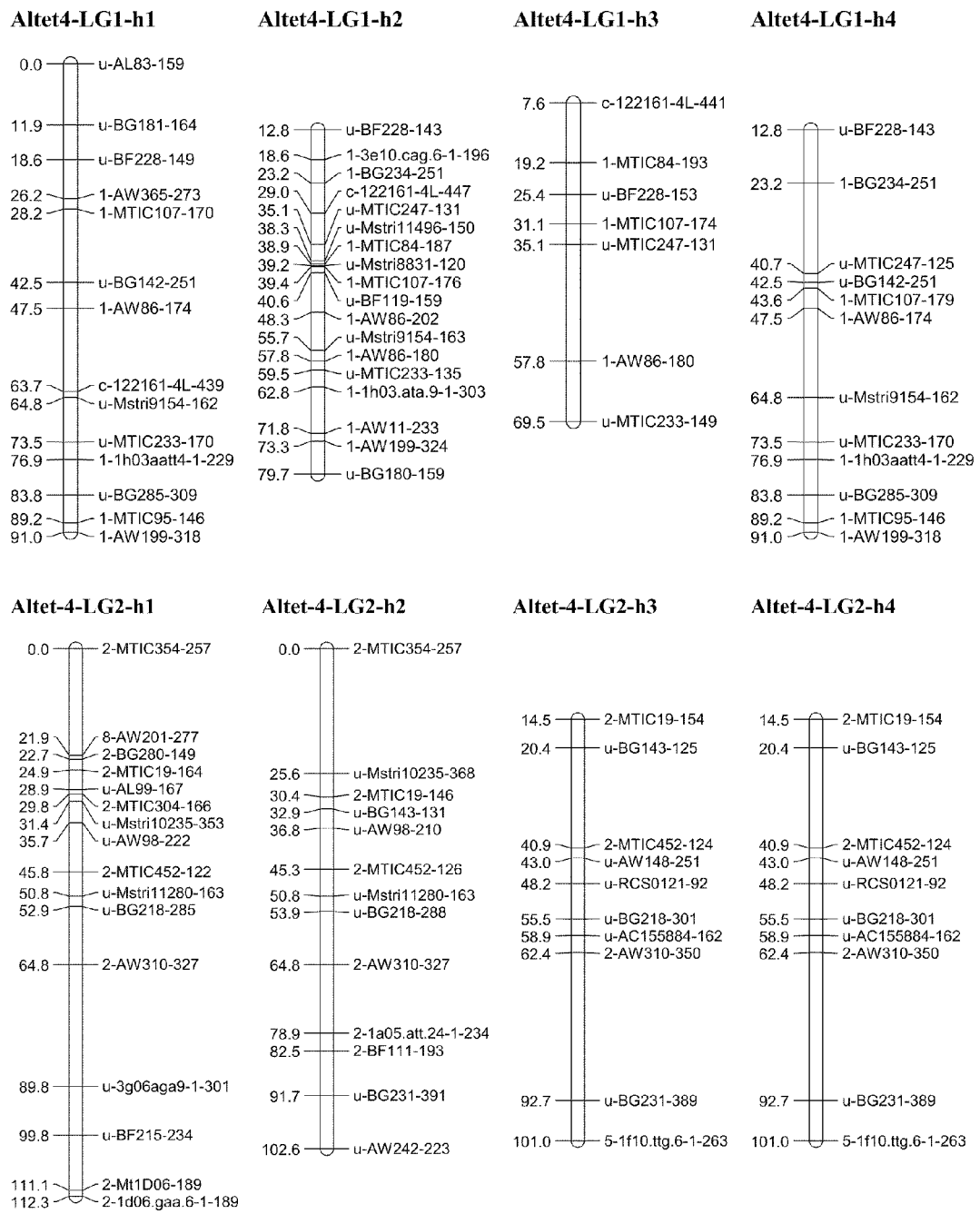
FIG. 9: Genetic map of the linkage groups of the Altet4 genotype constructed from the cross between Altet4 and NECS141. Linkage groups are denoted by "LG" followed by a number, e.g., LG1 is linkage group 1. Homeologous chromosomes are indicated by "h" followed by a number, e.g., h2 is chromosome number 2 out of the four homeologous chromosomes of a given linkage group.
Figure 9:
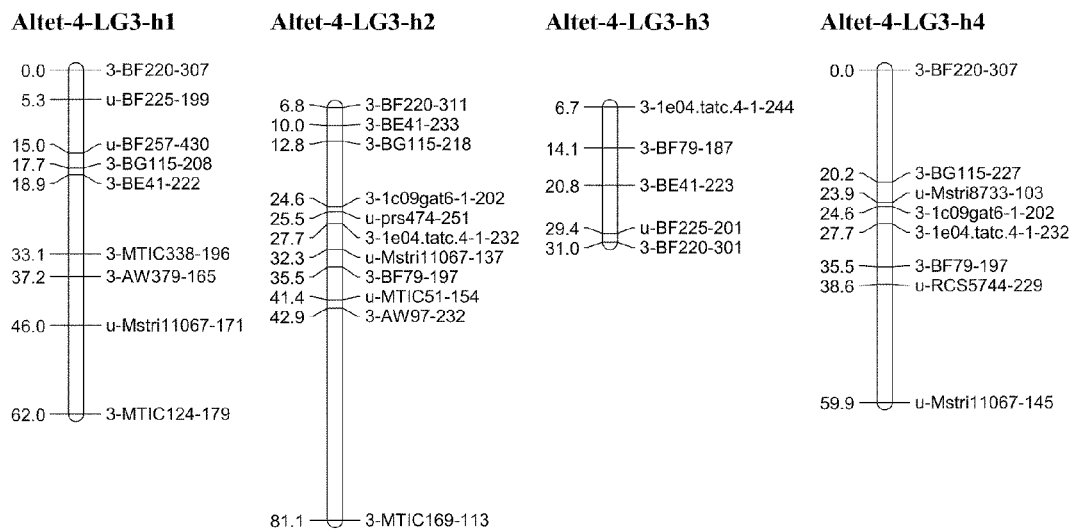
Figure 9:
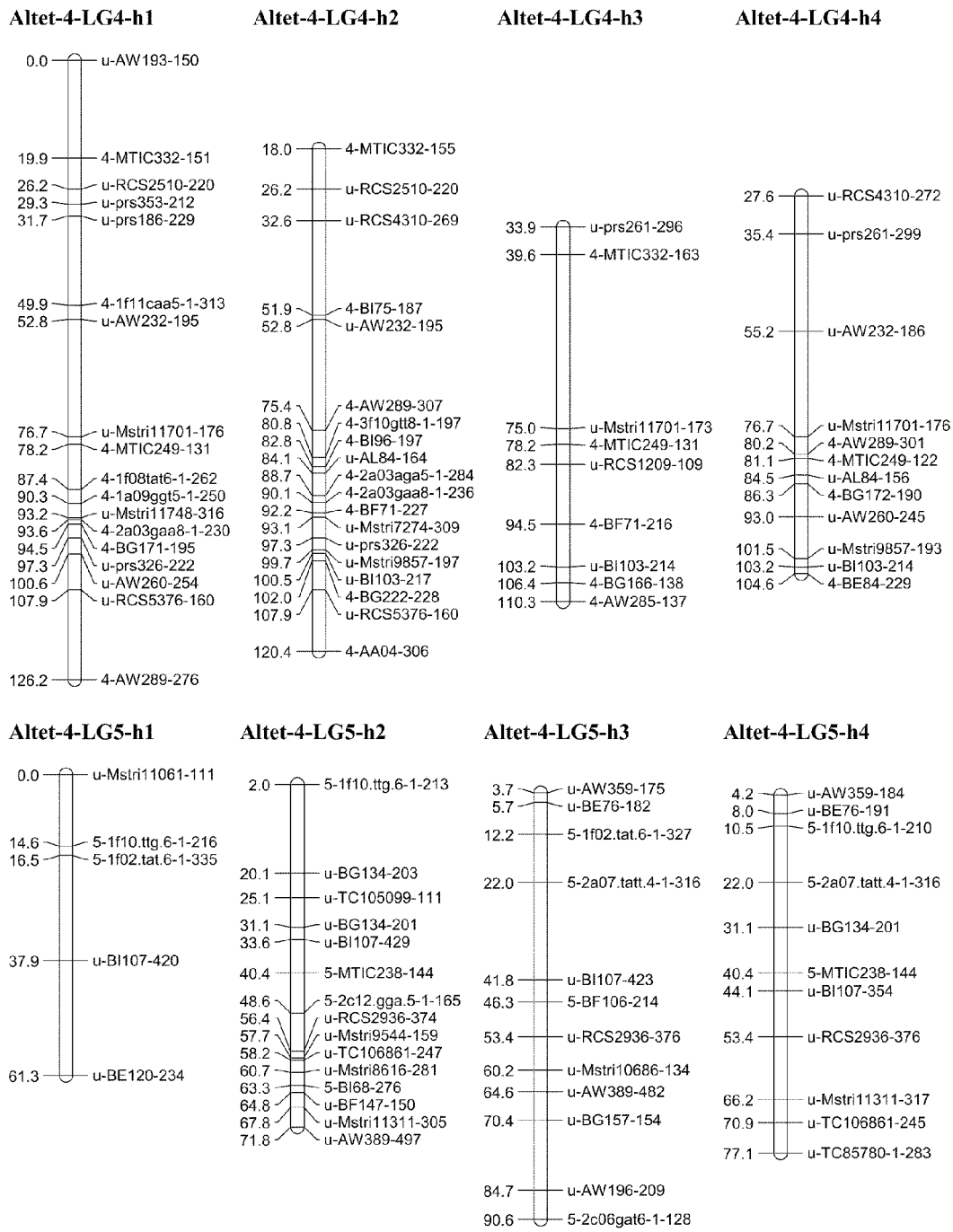
Figure 9:
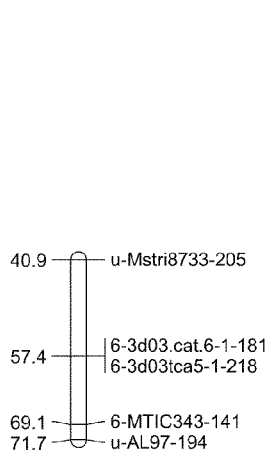
Figure 9:
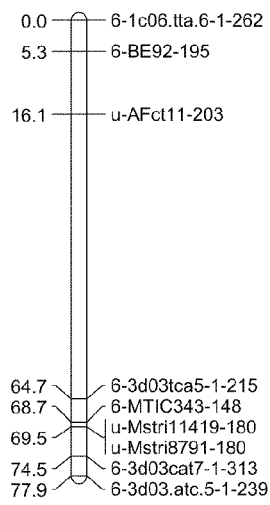
Figure 9:
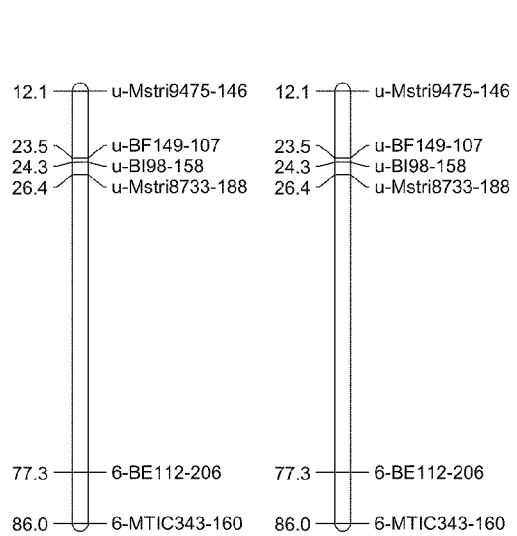
Figure 9:
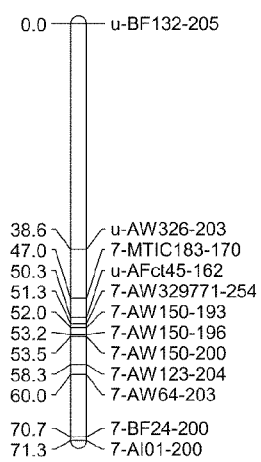
Figure 9:
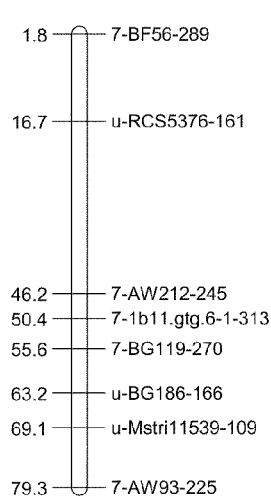
Figure 9:
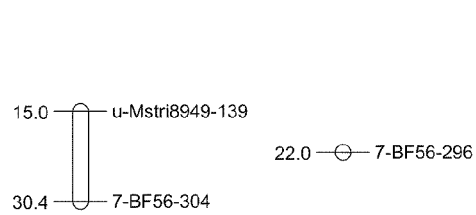
Figure 9:
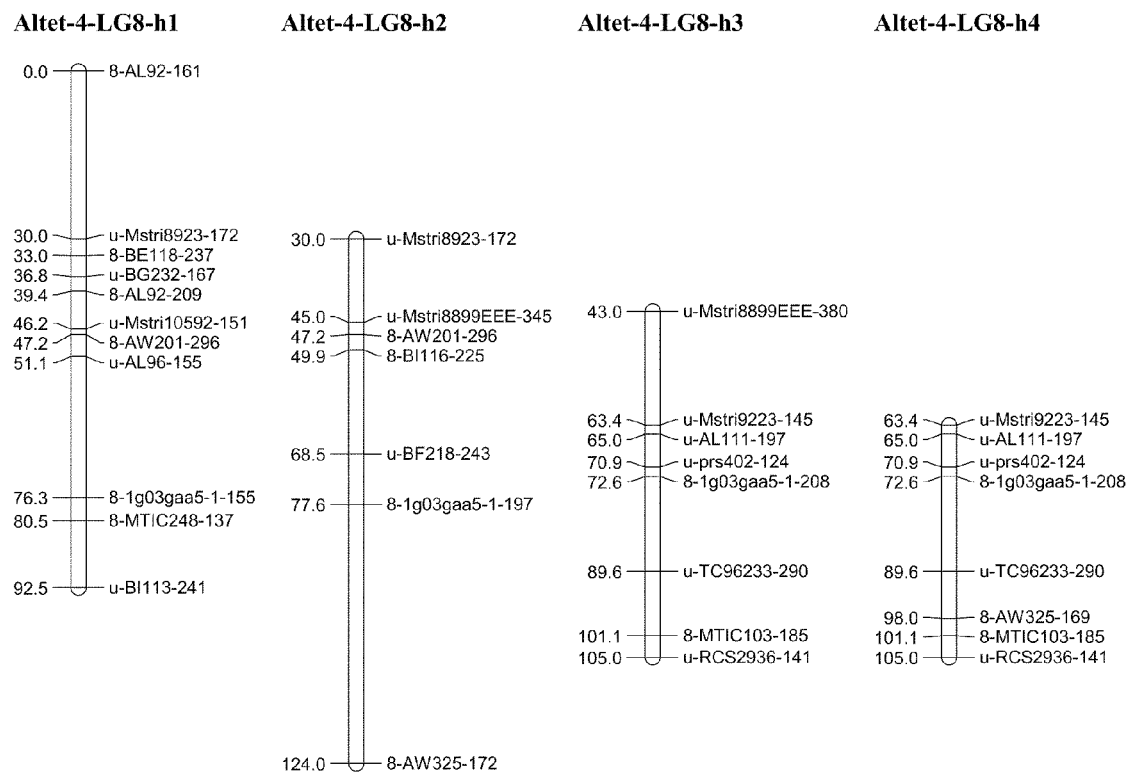
Figure 10:
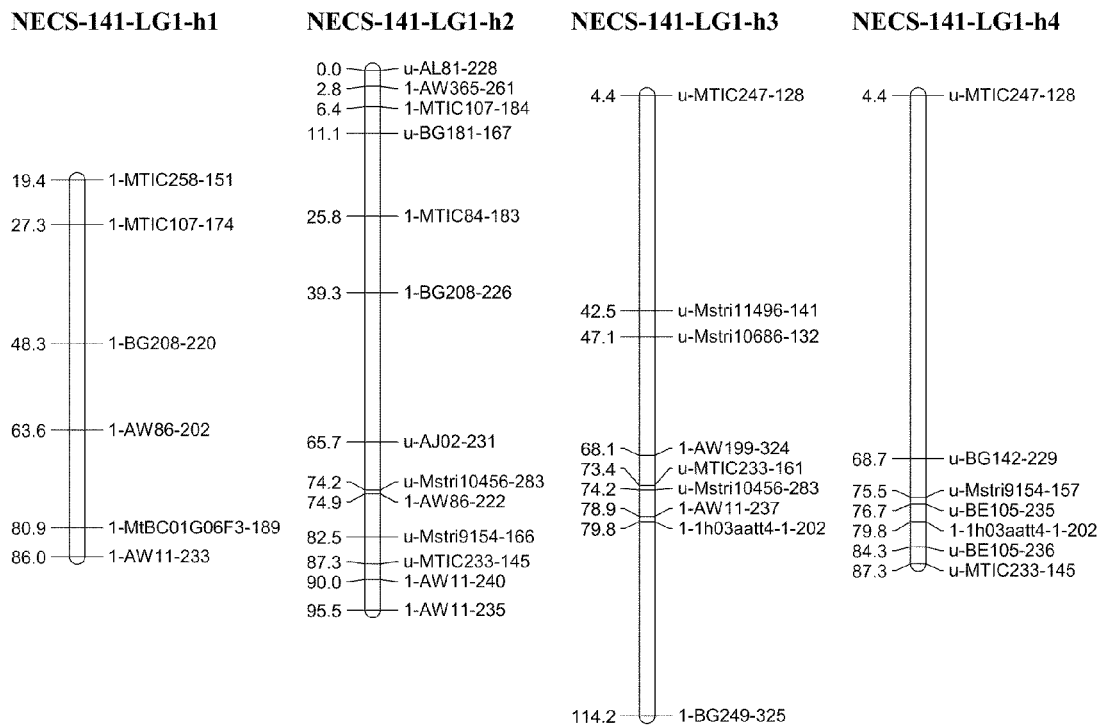
FIG. 10: Genetic map of the linkage groups of the NECS141 genotype constructed from the cross between Altet4 and NECS141. Linkage groups are denoted by "LG" followed by a number, e.g., LG1 is linkage group 1. Homeologous chromosomes are indicated by "h" followed by a number, e.g., h2 is chromosome number 2 out of the four homeologous chromosomes of a given linkage group.
Figure 10:
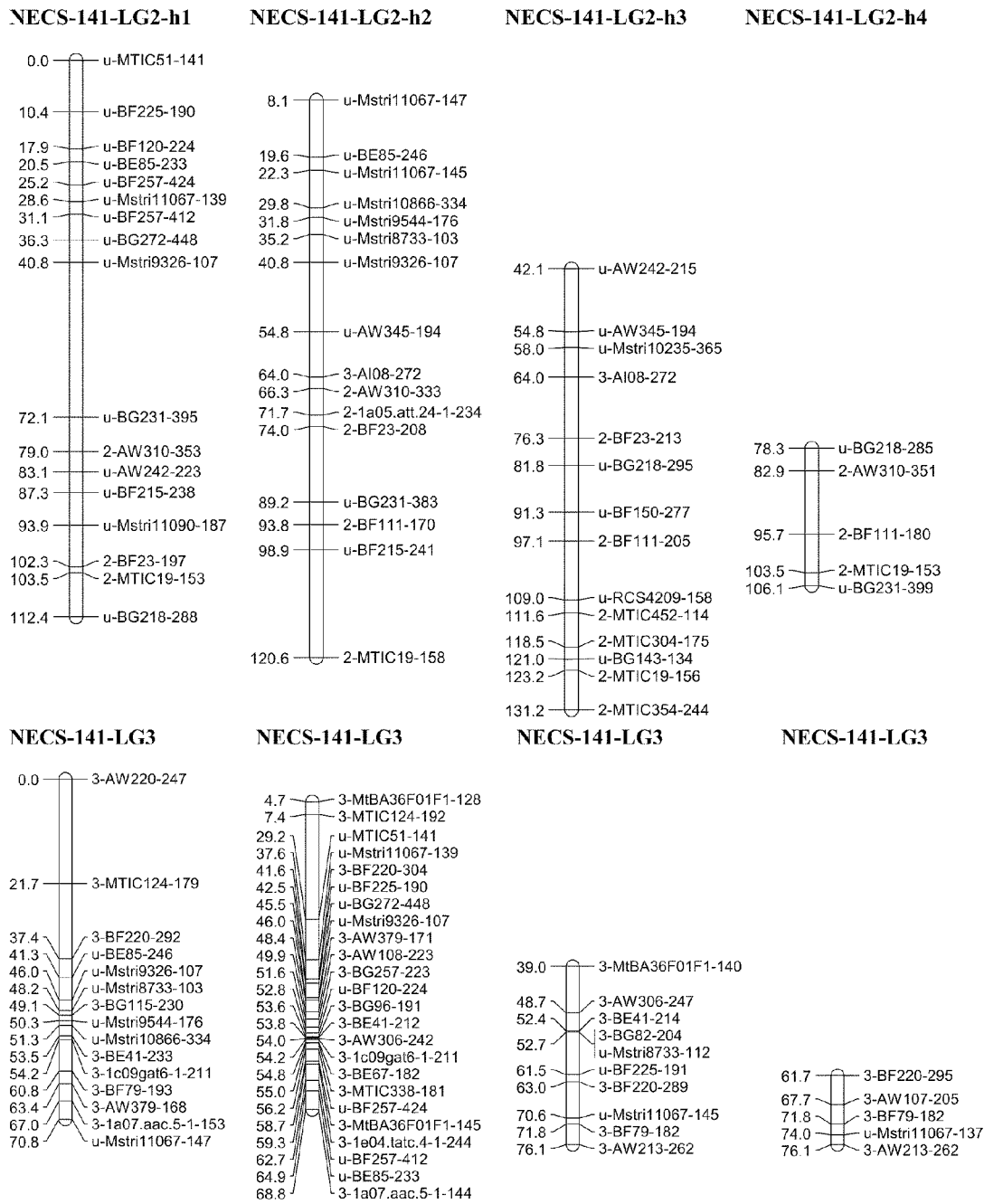
Figure 10:
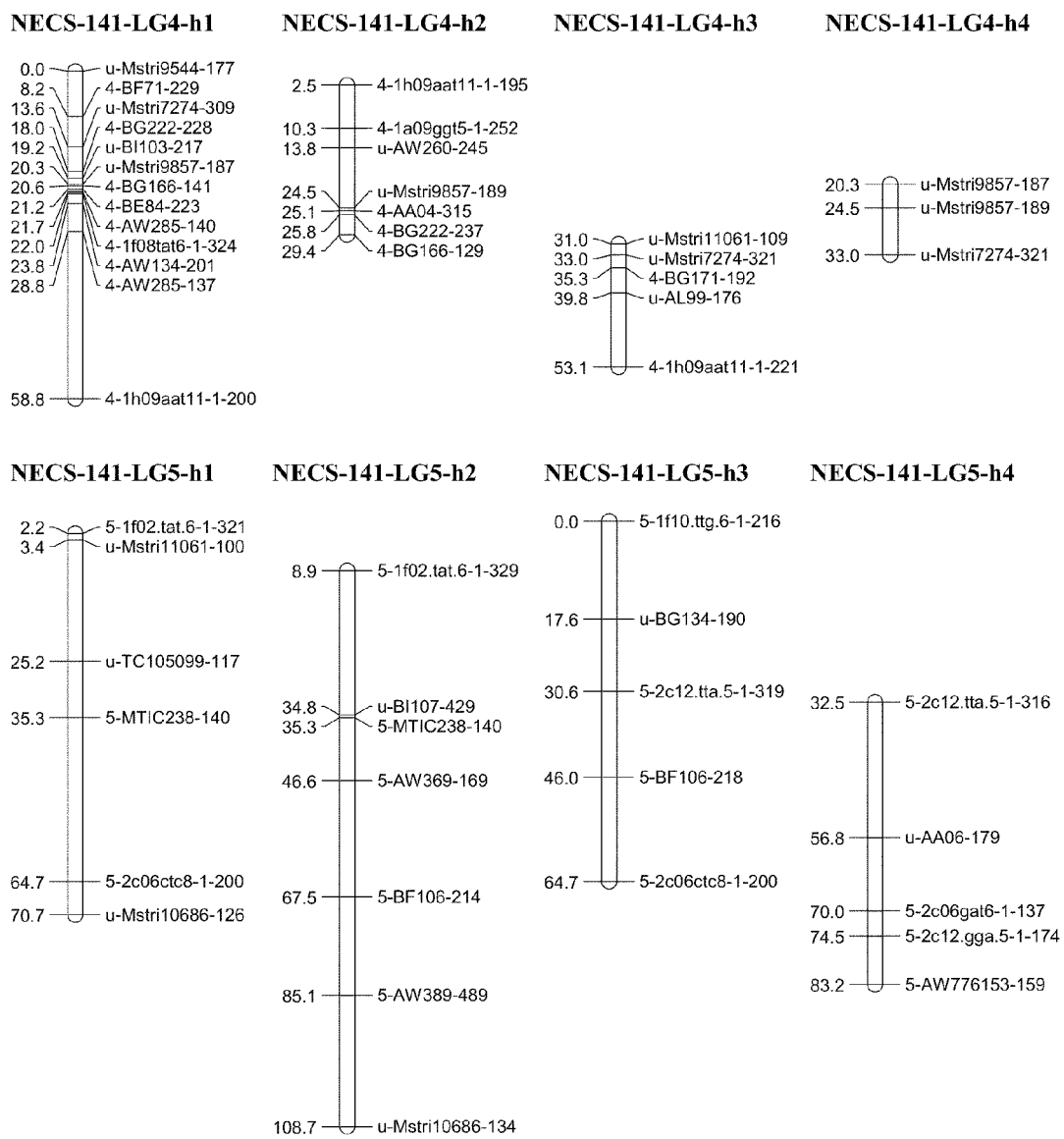
Figure 10:
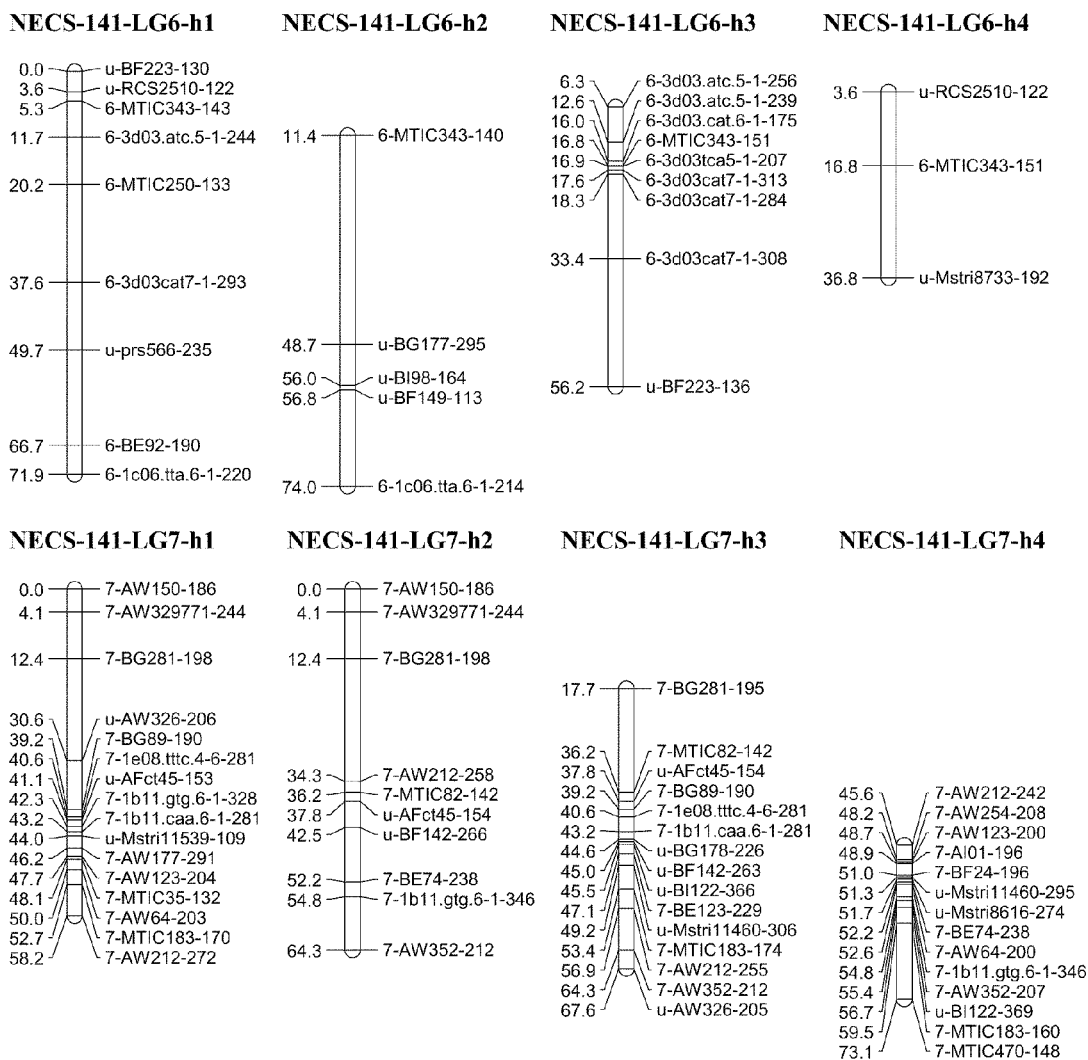
Figure 10:
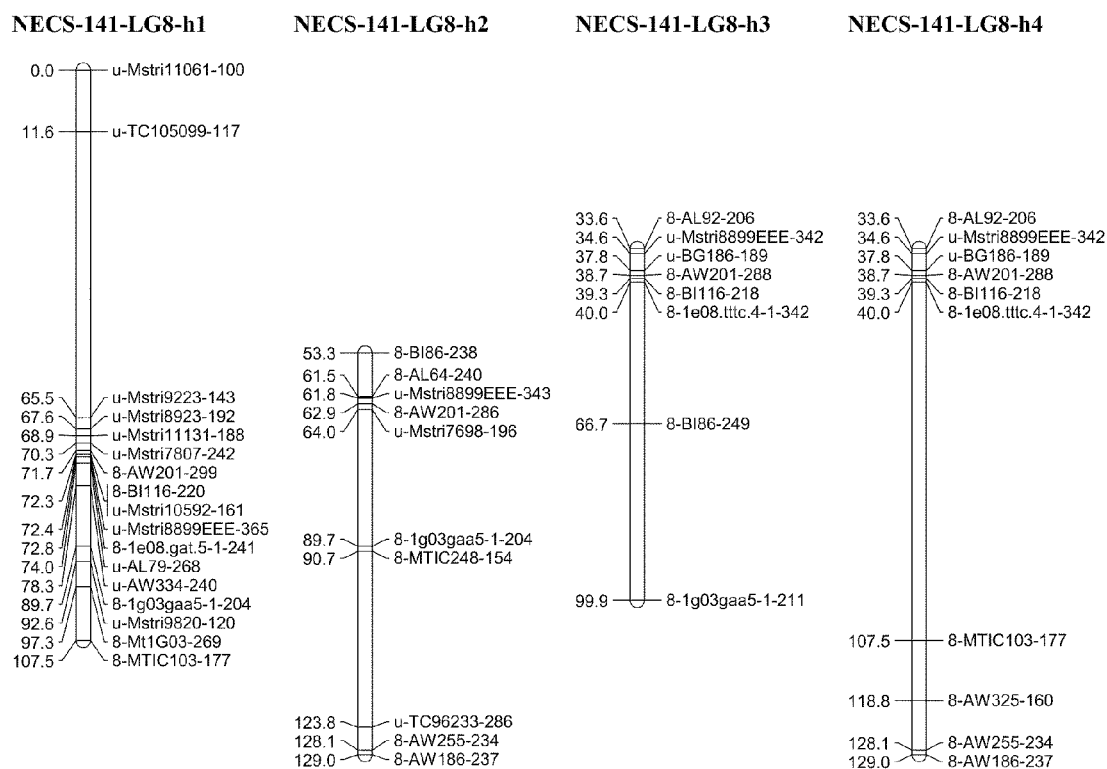

A total of 2738 legume SSR primer pairs were evaluated for polymorphism between the parental genotypes 95-608, NECS141, and Altet4. The total number of polymorphic primer pairs used to genotype the individuals from the 608Altet4 population and the NECS141Altet4 population was 573 and 884, respectively. Linkage groups from each homoeologous chromosome for all linkage groups including polymorphic markers were constructed for each of the parental genotypes in the 608Altet4 population (FIG. 7, 8) and the NECS141Altet4 population (FIG. 9, 10). Markers with segregation distortion due to uncovering of deleterious alleles and/or polyploidy inheritance were not included in the maps.

Example 11

Identification of Aluminum Tolerance Marker-Trait Associations

One-way analysis of variance (ANOVA) was performed to evaluate the association between aluminum tolerance phenotypic values from the callus growth ratio (+Al/−Al) and the polymorphic molecular markers. A non-parametric test for significant differences between the group medians (Kruskal-Wallis test) was also performed and used to identify significant marker-trait associations (Table 5). The mean ratio of progenies without the marker vs. the mean ratio of progenies with the marker and the standard error of difference between the means (SED) was also calculated. The results from these analysis identified linkage groups which contain aluminum tolerance QTLs.

Significant markers associated with aluminum tolerance using the callus bioassay phenotypic data were identified on LGs 1, 2, 3, 4, 5, 6, 7, and 8 (Table 5). The phenotypic variation explained by the QTLs associated with Al tolerance based on interval mapping on LGs 1, 2, 4, 5, 6, and 8 is 10.4%, 8.9%, 4.3%, 7.8%, 12.1%, and 7.1% (FIG. 5, 6).

Based on single-factor analysis of variance, molecular markers with relevance to Al tolerance in alfalfa were identified on LGs 1, 2, 4, 5, 6, 7, and 8 (Table 5). On LG1, the molecular marker 122161 (29.5 cM) was developed from malate dehydrogenase and showed a positive effect on the Al tolerance response of the progeny in this study. Also, marker BG180 located at position 58.5 cM was relevant in the single point analysis (Table 5) and in the interval mapping (FIG. 5). BG180 is located 3.8 cM away from marker AW86, which wasn't significant for Al tolerance in alfalfa at the diploid level described by Narasimhamoorthy et al. (2007a). However, AW86 is located 34.3 cM away from marker 122161, which was also relevant for Al tolerance in alfalfa at the diploid level. Additional Al tolerance QTLs in alfalfa at the diploid level were identified on LGs 2 and 3 (Narasimhamoorthy et al. (2007a). The amount of phenotypic variation explained by the identified Al tolerance QTLs ranged from 4.4% on LG4 to 12.1% on LG6, indicating that considerable progress can be made towards developing alfalfa with Al tolerance.

The rankings and magnitude of the Al tolerance responses in both populations is compared using tissue culture and whole plant based assay in media. These comparisons determine whether cell-based tolerance is relevant at the whole plant level.

Soil-based experiments in limed vs. unlimed soil with the two mapping populations are evaluated. Analysis of the allelic composition at each QTL enables identification of the contribution of each allele at the identified QTL to the aluminum-tolerance response.

All publications and patent applications cited herein are incorporated by reference to the same extent as if each individual publication or patent application was specifically and individually indicated to be incorporated by reference.

Although certain embodiments have been described in detail above, those having ordinary skill in the art will clearly understand that many modifications are possible in the embodiments without departing

TABLE 5

Single point analysis for aluminum tolerance based on phenotypic data from the callus bioassay

| LG | Marker | Effect | Average callus growth ratio (+Al/−Al) of progenies absent | present | Kruskal-Wallis test P value | ANOVA P value | Standard error |
|---|---|---|---|---|---|---|---|
| | | | Markers from Altet-4 | | | | |
| 1 | 1-MTIC107-179 | − | 0.796 | 0.746 | 0.028 | 0.118 | 0.032 |
| 1 | c-122161-4L-447 | + | 0.752 | 0.798 | 0.040 | 0.139 | 0.031 |
| 1 | u-BG180-159 | + | 0.749 | 0.813 | 0.068 | 0.039 | 0.031 |
| 1 | u-Mstri8831-120 | + | 0.738 | 0.800 | 0.026 | 0.055 | 0.032 |
| 2 | u-BG231-391 | + | 0.743 | 0.816 | 0.143 | 0.017 | 0.031 |
| 2 | 2-AW310-350 | + | 0.707 | 0.792 | 0.056 | 0.035 | 0.040 |
| 3 | 3-AI08-279 | − | 0.804 | 0.741 | 0.029 | 0.044 | 0.031 |
| 3 | 3-MtBA36F01F1-126 | − | 0.814 | 0.735 | 0.085 | 0.010 | 0.030 |
| 3 | u-MTIC233-149 | − | 0.806 | 0.740 | 0.195 | 0.032 | 0.031 |
| 4 | 4-1h09aat11-1-218 | + | 0.756 | 0.826 | 0.120 | 0.036 | 0.033 |
| 4 | 4-AA04-306 | + | 0.737 | 0.813 | 0.024 | 0.014 | 0.031 |
| 4 | u-Mstri11701-176 | − | 0.888 | 0.763 | 0.079 | 0.010 | 0.048 |
| 5 | 5-2a09.ttta.4-1-276 | + | 0.751 | 0.824 | 0.058 | 0.022 | 0.032 |
| 5 | u-BG157-154 | − | 0.806 | 0.735 | 0.073 | 0.025 | 0.031 |
| 6 | 6-BE112-200 | + | 0.758 | 0.857 | 0.056 | 0.011 | 0.039 |
| 7 | 7-AI01-200 | − | 0.808 | 0.745 | 0.049 | 0.043 | 0.031 |
| 7 | 7-AW329771-254 | − | 0.806 | 0.744 | 0.048 | 0.047 | 0.031 |
| 7 | u-AFct45-162 | − | 0.808 | 0.738 | 0.019 | 0.024 | 0.031 |
| 8 | 8-AL92-161 | + | 0.733 | 0.815 | 0.024 | 0.007 | 0.030 |
| | | | Markers from NECS-141 | | | | |
| 1 | 1-AW199-332 | − | 0.802 | 0.736 | 0.072 | 0.038 | 0.032 |
| 1 | 1-BF26-306 | − | 0.817 | 0.739 | 0.012 | 0.011 | 0.030 |
| 2 | 2-BF23-197 | − | 0.800 | 0.739 | 0.023 | 0.057 | 0.032 |
| 3 | 3-MtBA36F01F1-145 | − | 0.805 | 0.745 | 0.035 | 0.053 | 0.031 |
| 4 | 4-1f08caa5-1-158 | + | 0.737 | 0.803 | 0.081 | 0.038 | 0.031 |
| 4 | 4-1f08tat6-1-324 | + | 0.739 | 0.813 | 0.020 | 0.016 | 0.030 |
| 4 | u-Mstri9544-177 | + | 0.751 | 0.816 | 0.061 | 0.042 | 0.033 |
| 4 | 4-AW134-201 | + | 0.738 | 0.820 | 0.015 | 0.008 | 0.030 |
| 4 | 4-AW285-140 | + | 0.739 | 0.814 | 0.024 | 0.016 | 0.030 |
| 4 | 4-BE84-223 | + | 0.738 | 0.817 | 0.016 | 0.010 | 0.030 |
| 4 | 4-BF71-229 | + | 0.755 | 0.813 | 0.015 | 0.070 | 0.032 |
| 4 | 4-BG166-141 | + | 0.739 | 0.814 | 0.024 | 0.016 | 0.030 |
| 4 | 4-1h09aat11-1-233 | + | 0.748 | 0.851 | 0.018 | 0.002 | 0.031 |
| 5 | 5-AW776153-159 | + | 0.738 | 0.811 | 0.031 | 0.019 | 0.031 |
| 6-h1 | 6-3d03.atc.5-1-244 | + | 0.741 | 0.822 | 0.029 | 0.010 | 0.031 |
| 6-h2 | 6-BE112-178 | − | 0.807 | 0.745 | 0.080 | 0.047 | 0.031 |
| 6-h2 | u-BG249-348 | − | 0.800 | 0.733 | 0.039 | 0.040 | 0.032 |
| 6-h2 | u-BG272-448 | − | 0.817 | 0.719 | 0.002 | 0.002 | 0.031 |
| 6-h3 | 6-MTIC250-133 | + | 0.739 | 0.813 | 0.045 | 0.016 | 0.030 |
| 6-h3 | 6-MTIC343-143 | + | 0.739 | 0.826 | 0.015 | 0.005 | 0.030 |
| 7 | 7-BF56-306 | − | 0.818 | 0.735 | 0.005 | 0.007 | 0.030 | from the teachings thereof. All such modifications are intended to be encompassed within the invention as disclosed.

---

What is claimed is:

1. A method for producing an aluminum tolerant alfalfa line comprising introgressing at least one chromosomal locus contributing to aluminum tolerance from an aluminum tolerant alfalfa plant into a selected alfalfa line which is less aluminum tolerant prior to said introgression, wherein said chromosomal locus maps between loci 6-MTIC343-140 and 6-3d03.atc.5-1-244 on linkage group 6 or between loci 2-AW310-353 and 1-AW11-214 on linkage group 2; wherein the introgression is effected by marker assisted selection using at least a first genetic marker linked to said chromosomal locus.

2. The method of claim 1, wherein the aluminum tolerant alfalfa plant is an agronomically elite line.

3. The method of claim 1, wherein the aluminum tolerant alfalfa plant is a hybrid or inbred plant.

4. The method of claim 1, wherein the marker is 6-MTIC343-140, 6-3d03.atc.5-1-244, 2-AW310-353 or 1-AW11-214.

5. The method of claim 1, wherein the aluminum tolerant alfalfa plant exhibits at least a 50% reduction in aluminum sensitivity relative to the less aluminum tolerant alfalfa line.

6. The method of claim 5, wherein the aluminum tolerant alfalfa plant displays at least a 75% reduction in aluminum sensitivity relative to the less aluminum tolerant alfalfa line.

7. The method of claim 1, comprising introgressing both of said chromosomal locus mapping between loci 6-MTIC343-140 and 6-3d03.atc.5-1-244 on linkage group 6 and said chromosomal locus mapping between loci 2-AW310-353 and 1-AW11-214 on linkage group 2.

8. The method of claim 1, wherein the aluminum tolerant alfalfa plant is *Medicago sativa* subs. *caerulea* or Altet4.

9. An agronomically elite alfalfa plant produced by the method of claim 1, comprising at least one chromosomal locus contributing to aluminum tolerance, wherein said chromosomal locus maps between loci 6-MTIC343-140 and 6-3d03.atc.5-1-244 on linkage group 6 or between loci 2-AW310-353 and 1-AW11-214 on linkage group 2.

10. A seed that produces the plant of claim 9.

11. The plant of claim 9, which is inbred.

12. The plant of claim 9, which is hybrid.

13. A plant part of the plant of claim 9.

14. The plant part of claim 12, further defined as a leaf, an ovule, pollen, a fruit, or a cell.

15. The plant part of claim 12, further defined as a cell.

16. The plant of claim 9, wherein the plant comprises a transgene.

17. A tissue culture of regenerable cells of the plant of claim 9 wherein said tissue culture comprises at least one chromosomal locus contributing to aluminum tolerance from between loci 6-MTIC343-140 and 6-3d03.atc.5-1-244 on linkage group 6 or between loci 2-AW310-353 and 1-AW11-214 on linkage group 2.

18. The tissue culture according to claim 17, comprising cells or protoplasts from a plant part selected from the group consisting of embryos, meristems, cotyledons, pollen, leaves, anthers, roots, root tips, pistil, flower, seed and stalks.

19. An alfalfa plant regenerated from the tissue culture of claim 18, where the alfalfa plant comprises the chromosomal locus mapping between loci 6-MTIC343-140 and 6-3d03.atc.5-1-244 on linkage group 6 or between loci 2-AW310-353 and 1-AW11-214 on linkage group 2.

20. A method of producing an alfalfa seed comprising crossing the plant of claim 9 with itself or a second alfalfa plant and allowing seed to form, wherein the seed comprises at least one chromosomal locus contributing to aluminum tolerance, wherein said chromosomal locus maps between loci 6-MTIC343-140 and 6-3d03.atc.5-1-244 on linkage group 6 or between loci 2-AW310-353 and 1-AW11-214 on linkage group 2.

21. A method for obtaining an alfalfa plant comprising an allele conferring aluminum tolerance comprising:
  a) obtaining nucleic acids from an alfalfa plant comprising at least a first allele that confers aluminum tolerance, wherein said allele maps between loci 6-MTIC343-140 and 6-3d03.atc.5-1-244 on linkage group 6 or between loci 2-AW310-353 and 1-AW11-214 on linkage group 2;
  b) assaying said nucleic acids for the presence of at least a first genetic marker that is genetically linked to said allele; and
  c) selecting the alfalfa plant based on the presence of said genetic marker.

22. The method of claim 21, wherein the alfalfa plant is a progeny of a plant of *Medicago sativa* subs. *caerulea* or Altet4.

* * * * *

SEQUENCE LISTING

<160> NUMBER OF SEQ ID NOS: 250

<210> SEQ ID NO 1
<211> LENGTH: 42
<212> TYPE: DNA
<213> ORGANISM: Artificial Sequence
<220> FEATURE:
<223> OTHER INFORMATION: PCR primer

<400> SEQUENCE: 1
tgtaaaacga cggccagtaa agaattttag tctttgcgag aa                         42

<210> SEQ ID NO 2
<211> LENGTH: 21
<212> TYPE: DNA
<213> ORGANISM: Artificial Sequence
<220> FEATURE:
<223> OTHER INFORMATION: PCR primer

<400> SEQUENCE: 2
ccgagtgtgt tcgatagcat t                                               21

<210> SEQ ID NO 3
<211> LENGTH: 39
<212> TYPE: DNA
<213> ORGANISM: Artificial Sequence
<220> FEATURE:
<223> OTHER INFORMATION: PCR primer

<400> SEQUENCE: 3
tgtaaaacga cggccagtcg gcattgattt tcttcacaa                            39

<210> SEQ ID NO 4
<211> LENGTH: 21
<212> TYPE: DNA
<213> ORGANISM: Artificial Sequence
<220> FEATURE:
<223> OTHER INFORMATION: PCR primer

<400> SEQUENCE: 4
gcctcaacct agttccaaac c                                               21

<210> SEQ ID NO 5
<211> LENGTH: 39
<212> TYPE: DNA
<213> ORGANISM: Artificial Sequence
<220> FEATURE:
<223> OTHER INFORMATION: PCR primer

<400> SEQUENCE: 5
tgtaaaacga cggccagtat atcaccactt agccgagcc                            39

<210> SEQ ID NO 6
<211> LENGTH: 21
<212> TYPE: DNA
<213> ORGANISM: Artificial Sequence
<220> FEATURE:
<223> OTHER INFORMATION: PCR primer

<400> SEQUENCE: 6
tgatcgagat tttgagcctg t                                               21

<210> SEQ ID NO 7
<211> LENGTH: 39
<212> TYPE: DNA
<213> ORGANISM: Artificial Sequence
<220> FEATURE:
<223> OTHER INFORMATION: PCR primer

<400> SEQUENCE: 7
tgtaaaacga cggccagtaa ttcccaattc tcattcgtg                         39

<210> SEQ ID NO 8
<211> LENGTH: 21
<212> TYPE: DNA
<213> ORGANISM: Artificial Sequence
<220> FEATURE:
<223> OTHER INFORMATION: PCR primer

<400> SEQUENCE: 8
gggaaaccat ttcgtaccct a                                           21

<210> SEQ ID NO 9
<211> LENGTH: 42
<212> TYPE: DNA
<213> ORGANISM: Artificial Sequence
<220> FEATURE:
<223> OTHER INFORMATION: PCR primer

<400> SEQUENCE: 9
tgtaaaacga cggccagtgc tttaaccgat tcagtttctc tc                    42

<210> SEQ ID NO 10
<211> LENGTH: 21
<212> TYPE: DNA
<213> ORGANISM: Artificial Sequence
<220> FEATURE:
<223> OTHER INFORMATION: PCR primer

<400> SEQUENCE: 10
tcatcacatg acgaagctca g                                           21

<210> SEQ ID NO 11
<211> LENGTH: 39
<212> TYPE: DNA
<213> ORGANISM: Artificial Sequence
<220> FEATURE:
<223> OTHER INFORMATION: PCR primer

<400> SEQUENCE: 11
tgtaaaacga cggccagtcc ttaacacatt tttgcttca                        39

<210> SEQ ID NO 12
<211> LENGTH: 21
<212> TYPE: DNA
<213> ORGANISM: Artificial Sequence
<220> FEATURE:
<223> OTHER INFORMATION: PCR primer

<400> SEQUENCE: 12
ttgccatcgt agaaaatggt c                                           21

<210> SEQ ID NO 13
<211> LENGTH: 39
<212> TYPE: DNA
<213> ORGANISM: Artificial Sequence
<220> FEATURE:
<223> OTHER INFORMATION: PCR primer

<400> SEQUENCE: 13
tgtaaaacga cggccagtgg tatgttcgga tcttggtga        39

<210> SEQ ID NO 14
<211> LENGTH: 21
<212> TYPE: DNA
<213> ORGANISM: Artificial Sequence
<220> FEATURE:
<223> OTHER INFORMATION: PCR primer

<400> SEQUENCE: 14
caacagctcc ctgaaaaaca g        21

<210> SEQ ID NO 15
<211> LENGTH: 40
<212> TYPE: DNA
<213> ORGANISM: Artificial Sequence
<220> FEATURE:
<223> OTHER INFORMATION: PCR primer

<400> SEQUENCE: 15
tgtaaaacga cggccagttg tacttgcagg gtgttttca        40

<210> SEQ ID NO 16
<211> LENGTH: 21
<212> TYPE: DNA
<213> ORGANISM: Artificial Sequence
<220> FEATURE:
<223> OTHER INFORMATION: PCR primer

<400> SEQUENCE: 16
aactttcatt ctaatgccac a        21

<210> SEQ ID NO 17
<211> LENGTH: 38
<212> TYPE: DNA
<213> ORGANISM: Artificial Sequence
<220> FEATURE:
<223> OTHER INFORMATION: PCR primer

<400> SEQUENCE: 17
tgtaaaacga cggccagttg gttacaacca cggtggag        38

<210> SEQ ID NO 18
<211> LENGTH: 21
<212> TYPE: DNA
<213> ORGANISM: Artificial Sequence
<220> FEATURE:
<223> OTHER INFORMATION: PCR primer

<400> SEQUENCE: 18
tgatcagttt tgagttttgt c        21

<210> SEQ ID NO 19
<211> LENGTH: 39
<212> TYPE: DNA
<213> ORGANISM: Artificial Sequence
<220> FEATURE:
<223> OTHER INFORMATION: PCR primer

<400> SEQUENCE: 19
tgtaaaacga cggccagttt atcatgtgca gacaatacc        39

<210> SEQ ID NO 20
<211> LENGTH: 21

<210> SEQ ID NO 20
<211> LENGTH: 21
<212> TYPE: DNA
<213> ORGANISM: Artificial Sequence
<220> FEATURE:
<223> OTHER INFORMATION: PCR primer

<400> SEQUENCE: 20
tgtcgtcttt tgaccatttc c                                         21

<210> SEQ ID NO 21
<211> LENGTH: 38
<212> TYPE: DNA
<213> ORGANISM: Artificial Sequence
<220> FEATURE:
<223> OTHER INFORMATION: PCR primer

<400> SEQUENCE: 21
tgtaaaacga cggccagtaa gagaaagaag ggggaacg                       38

<210> SEQ ID NO 22
<211> LENGTH: 21
<212> TYPE: DNA
<213> ORGANISM: Artificial Sequence
<220> FEATURE:
<223> OTHER INFORMATION: PCR primer

<400> SEQUENCE: 22
ctcttactct tcctcaccgg c                                         21

<210> SEQ ID NO 23
<211> LENGTH: 39
<212> TYPE: DNA
<213> ORGANISM: Artificial Sequence
<220> FEATURE:
<223> OTHER INFORMATION: PCR primer

<400> SEQUENCE: 23
tgtaaaacga cggccagtgt ctgctgctcc agctaagaa                      39

<210> SEQ ID NO 24
<211> LENGTH: 21
<212> TYPE: DNA
<213> ORGANISM: Artificial Sequence
<220> FEATURE:
<223> OTHER INFORMATION: PCR primer

<400> SEQUENCE: 24
ccttggcagc tacaggtaca g                                         21

<210> SEQ ID NO 25
<211> LENGTH: 39
<212> TYPE: DNA
<213> ORGANISM: Artificial Sequence
<220> FEATURE:
<223> OTHER INFORMATION: PCR primer

<400> SEQUENCE: 25
tgtaaaacga cggccagtcc aaatatcttc gctcttcca                      39

<210> SEQ ID NO 26
<211> LENGTH: 21
<212> TYPE: DNA
<213> ORGANISM: Artificial Sequence
<220> FEATURE:
<223> OTHER INFORMATION: PCR primer

<400> SEQUENCE: 26
tcacatcagc cctaacattc c                                         21

<210> SEQ ID NO 27
<211> LENGTH: 39
<212> TYPE: DNA
<213> ORGANISM: Artificial Sequence
<220> FEATURE:
<223> OTHER INFORMATION: PCR primer

<400> SEQUENCE: 27
tgtaaaacga cggccagtgg ttgaaatcga catgagagg                    39

<210> SEQ ID NO 28
<211> LENGTH: 24
<212> TYPE: DNA
<213> ORGANISM: Artificial Sequence
<220> FEATURE:
<223> OTHER INFORMATION: PCR primer

<400> SEQUENCE: 28
gattaaacat acatgcaaca ttga                                   24

<210> SEQ ID NO 29
<211> LENGTH: 39
<212> TYPE: DNA
<213> ORGANISM: Artificial Sequence
<220> FEATURE:
<223> OTHER INFORMATION: PCR primer

<400> SEQUENCE: 29
tgtaaaacga cggccagtgc tgttggtgct cttgctact                    39

<210> SEQ ID NO 30
<211> LENGTH: 21
<212> TYPE: DNA
<213> ORGANISM: Artificial Sequence
<220> FEATURE:
<223> OTHER INFORMATION: PCR primer

<400> SEQUENCE: 30
ttctgagcag gaatcaaagg a                                      21

<210> SEQ ID NO 31
<211> LENGTH: 40
<212> TYPE: DNA
<213> ORGANISM: Artificial Sequence
<220> FEATURE:
<223> OTHER INFORMATION: PCR primer

<400> SEQUENCE: 31
tgtaaaacga cggccagtca ggaaaacttg aagaagcaga                   40

<210> SEQ ID NO 32
<211> LENGTH: 23
<212> TYPE: DNA
<213> ORGANISM: Artificial Sequence
<220> FEATURE:
<223> OTHER INFORMATION: PCR primer

<400> SEQUENCE: 32
tccatggtat tttggtaaaa ctc                                    23

<210> SEQ ID NO 33
<211> LENGTH: 39
<212> TYPE: DNA
<213> ORGANISM: Artificial Sequence
<220> FEATURE:
<223> OTHER INFORMATION: PCR primer -continued

```
<400> SEQUENCE: 33
tgtaaaacga cggccagtac aacccattt ccaactttc                                39

<210> SEQ ID NO 34
<211> LENGTH: 21
<212> TYPE: DNA
<213> ORGANISM: Artificial Sequence
<220> FEATURE:
<223> OTHER INFORMATION: PCR primer

<400> SEQUENCE: 34
ggatatcctg gtggagggta a                                                  21

<210> SEQ ID NO 35
<211> LENGTH: 38
<212> TYPE: DNA
<213> ORGANISM: Artificial Sequence
<220> FEATURE:
<223> OTHER INFORMATION: PCR primer

<400> SEQUENCE: 35
tgtaaaacga cggccagtcc aatgcagttc ggtaatcc                                38

<210> SEQ ID NO 36
<211> LENGTH: 21
<212> TYPE: DNA
<213> ORGANISM: Artificial Sequence
<220> FEATURE:
<223> OTHER INFORMATION: PCR primer

<400> SEQUENCE: 36
cctccaggtc taagtcccat t                                                  21

<210> SEQ ID NO 37
<211> LENGTH: 41
<212> TYPE: DNA
<213> ORGANISM: Artificial Sequence
<220> FEATURE:
<223> OTHER INFORMATION: PCR primer

<400> SEQUENCE: 37
tgtaaaacga cggccagttg ttctcctctc ttcgtctctt g                            41

<210> SEQ ID NO 38
<211> LENGTH: 21
<212> TYPE: DNA
<213> ORGANISM: Artificial Sequence
<220> FEATURE:
<223> OTHER INFORMATION: PCR primer

<400> SEQUENCE: 38
ccaacacttt aagcctccaa a                                                  21

<210> SEQ ID NO 39
<211> LENGTH: 40
<212> TYPE: DNA
<213> ORGANISM: Artificial Sequence
<220> FEATURE:
<223> OTHER INFORMATION: PCR primer

<400> SEQUENCE: 39
tgtaaaacga cggccagtag tgttggtttc cttgaatttt                              40

<210> SEQ ID NO 40
<211> LENGTH: 20
```

```
<212> TYPE: DNA
<213> ORGANISM: Artificial Sequence
<220> FEATURE:
<223> OTHER INFORMATION: PCR primer

<400> SEQUENCE: 40
gtagcgggcg ctatttcggt                                           20

<210> SEQ ID NO 41
<211> LENGTH: 39
<212> TYPE: DNA
<213> ORGANISM: Artificial Sequence
<220> FEATURE:
<223> OTHER INFORMATION: PCR primer

<400> SEQUENCE: 41
tgtaaaacga cggccagtaa ccagagaaaa atccaacca                       39

<210> SEQ ID NO 42
<211> LENGTH: 21
<212> TYPE: DNA
<213> ORGANISM: Artificial Sequence
<220> FEATURE:
<223> OTHER INFORMATION: PCR primer

<400> SEQUENCE: 42
ccggttctgt ttggtagtga a                                         21

<210> SEQ ID NO 43
<211> LENGTH: 39
<212> TYPE: DNA
<213> ORGANISM: Artificial Sequence
<220> FEATURE:
<223> OTHER INFORMATION: PCR primer

<400> SEQUENCE: 43
tgtaaaacga cggccagtgc cttttatcgg ctgatttct                       39

<210> SEQ ID NO 44
<211> LENGTH: 24
<212> TYPE: DNA
<213> ORGANISM: Artificial Sequence
<220> FEATURE:
<223> OTHER INFORMATION: PCR primer

<400> SEQUENCE: 44
tcctatccag ttacggatca tttt                                      24

<210> SEQ ID NO 45
<211> LENGTH: 40
<212> TYPE: DNA
<213> ORGANISM: Artificial Sequence
<220> FEATURE:
<223> OTHER INFORMATION: PCR primer

<400> SEQUENCE: 45
tgtaaaacga cggccagttc acaaaacaaa cccttcttct                      40

<210> SEQ ID NO 46
<211> LENGTH: 21
<212> TYPE: DNA
<213> ORGANISM: Artificial Sequence
<220> FEATURE:
<223> OTHER INFORMATION: PCR primer

<400> SEQUENCE: 46
ggagcaaaca ttctaccacc a                                         21
```

<210> SEQ ID NO 47
<211> LENGTH: 38
<212> TYPE: DNA
<213> ORGANISM: Artificial Sequence
<220> FEATURE:
<223> OTHER INFORMATION: PCR primer

<400> SEQUENCE: 47
tgtaaaacga cggccagtat cgacaggtac cggaacag                                    38

<210> SEQ ID NO 48
<211> LENGTH: 21
<212> TYPE: DNA
<213> ORGANISM: Artificial Sequence
<220> FEATURE:
<223> OTHER INFORMATION: PCR primer

<400> SEQUENCE: 48
catcattcat tcctccagct c                                                      21

<210> SEQ ID NO 49
<211> LENGTH: 39
<212> TYPE: DNA
<213> ORGANISM: Artificial Sequence
<220> FEATURE:
<223> OTHER INFORMATION: PCR primer

<400> SEQUENCE: 49
tgtaaaacga cggccagtta agggttcatg ctcaccatc                                   39

<210> SEQ ID NO 50
<211> LENGTH: 21
<212> TYPE: DNA
<213> ORGANISM: Artificial Sequence
<220> FEATURE:
<223> OTHER INFORMATION: PCR primer

<400> SEQUENCE: 50
ccttaggcac attgaaaacc a                                                      21

<210> SEQ ID NO 51
<211> LENGTH: 39
<212> TYPE: DNA
<213> ORGANISM: Artificial Sequence
<220> FEATURE:
<223> OTHER INFORMATION: PCR primer

<400> SEQUENCE: 51
tgtaaaacga cggccagttc gctcctactt cttctggtg                                   39

<210> SEQ ID NO 52
<211> LENGTH: 21
<212> TYPE: DNA
<213> ORGANISM: Artificial Sequence
<220> FEATURE:
<223> OTHER INFORMATION: PCR primer

<400> SEQUENCE: 52
tgggtcttgg gtagatgaat g                                                      21

<210> SEQ ID NO 53
<211> LENGTH: 39
<212> TYPE: DNA
<213> ORGANISM: Artificial Sequence
<220> FEATURE:
<223> OTHER INFORMATION: PCR primer

```
<400> SEQUENCE: 53
tgtaaaacga cggccagttc ttgcattgca ccataaacc                              39

<210> SEQ ID NO 54
<211> LENGTH: 21
<212> TYPE: DNA
<213> ORGANISM: Artificial Sequence
<220> FEATURE:
<223> OTHER INFORMATION: PCR primer

<400> SEQUENCE: 54
ccgttgatcc tgtcacaaac t                                                 21

<210> SEQ ID NO 55
<211> LENGTH: 36
<212> TYPE: DNA
<213> ORGANISM: Artificial Sequence
<220> FEATURE:
<223> OTHER INFORMATION: PCR primer

<400> SEQUENCE: 55
tgtaaaacga cggccagttt ttccgcttcc gttttt                                 36

<210> SEQ ID NO 56
<211> LENGTH: 21
<212> TYPE: DNA
<213> ORGANISM: Artificial Sequence
<220> FEATURE:
<223> OTHER INFORMATION: PCR primer

<400> SEQUENCE: 56
ttctgaatac caccaactcc g                                                 21

<210> SEQ ID NO 57
<211> LENGTH: 38
<212> TYPE: DNA
<213> ORGANISM: Artificial Sequence
<220> FEATURE:
<223> OTHER INFORMATION: PCR primer

<400> SEQUENCE: 57
tgtaaaacga cggccagtag aaagggagga tctctgcg                               38

<210> SEQ ID NO 58
<211> LENGTH: 21
<212> TYPE: DNA
<213> ORGANISM: Artificial Sequence
<220> FEATURE:
<223> OTHER INFORMATION: PCR primer

<400> SEQUENCE: 58
gttgttcctc ccctgttctt c                                                 21

<210> SEQ ID NO 59
<211> LENGTH: 38
<212> TYPE: DNA
<213> ORGANISM: Artificial Sequence
<220> FEATURE:
<223> OTHER INFORMATION: PCR primer

<400> SEQUENCE: 59
tgtaaaacga cggccagtgt tgcggtggaa gagaaacc                               38

<210> SEQ ID NO 60
<211> LENGTH: 21
```

<212> TYPE: DNA
<213> ORGANISM: Artificial Sequence
<220> FEATURE:
<223> OTHER INFORMATION: PCR primer

<400> SEQUENCE: 60
ttcccagcaa aaacaatttc a                                              21

<210> SEQ ID NO 61
<211> LENGTH: 39
<212> TYPE: DNA
<213> ORGANISM: Artificial Sequence
<220> FEATURE:
<223> OTHER INFORMATION: PCR primer

<400> SEQUENCE: 61
tgtaaaacga cggccagtac ctgaaaggcc acaaaagat                            39

<210> SEQ ID NO 62
<211> LENGTH: 23
<212> TYPE: DNA
<213> ORGANISM: Artificial Sequence
<220> FEATURE:
<223> OTHER INFORMATION: PCR primer

<400> SEQUENCE: 62
aacatgcaca attaagcatt caa                                            23

<210> SEQ ID NO 63
<211> LENGTH: 40
<212> TYPE: DNA
<213> ORGANISM: Artificial Sequence
<220> FEATURE:
<223> OTHER INFORMATION: PCR primer

<400> SEQUENCE: 63
tgtaaaacga cggccagttt gcctcggatt attacttgtg                          40

<210> SEQ ID NO 64
<211> LENGTH: 21
<212> TYPE: DNA
<213> ORGANISM: Artificial Sequence
<220> FEATURE:
<223> OTHER INFORMATION: PCR primer

<400> SEQUENCE: 64
aattcgggtg gaataacaag c                                              21

<210> SEQ ID NO 65
<211> LENGTH: 39
<212> TYPE: DNA
<213> ORGANISM: Artificial Sequence
<220> FEATURE:
<223> OTHER INFORMATION: PCR primer

<400> SEQUENCE: 65
tgtaaaacga cggccagttc atccattcat taaaacgca                           39

<210> SEQ ID NO 66
<211> LENGTH: 21
<212> TYPE: DNA
<213> ORGANISM: Artificial Sequence
<220> FEATURE:
<223> OTHER INFORMATION: PCR primer

<400> SEQUENCE: 66
tgacttagac accaccggag t                                              21

<210> SEQ ID NO 67
<211> LENGTH: 40
<212> TYPE: DNA
<213> ORGANISM: Artificial Sequence
<220> FEATURE:
<223> OTHER INFORMATION: PCR primer

<400> SEQUENCE: 67
tgtaaaacga cggccagttt agggttagat tcgtcgatca                    40

<210> SEQ ID NO 68
<211> LENGTH: 20
<212> TYPE: DNA
<213> ORGANISM: Artificial Sequence
<220> FEATURE:
<223> OTHER INFORMATION: PCR primer

<400> SEQUENCE: 68
aaaccagccg aagaggattt                                          20

<210> SEQ ID NO 69
<211> LENGTH: 39
<212> TYPE: DNA
<213> ORGANISM: Artificial Sequence
<220> FEATURE:
<223> OTHER INFORMATION: PCR primer

<400> SEQUENCE: 69
tgtaaaacga cggccagtgc cagttttggg caattttat                     39

<210> SEQ ID NO 70
<211> LENGTH: 21
<212> TYPE: DNA
<213> ORGANISM: Artificial Sequence
<220> FEATURE:
<223> OTHER INFORMATION: PCR primer

<400> SEQUENCE: 70
gcaatcacct tagcattttg g                                        21

<210> SEQ ID NO 71
<211> LENGTH: 39
<212> TYPE: DNA
<213> ORGANISM: Artificial Sequence
<220> FEATURE:
<223> OTHER INFORMATION: PCR primer

<400> SEQUENCE: 71
tgtaaaacga cggccagttt gttctgttct ctcacccga                     39

<210> SEQ ID NO 72
<211> LENGTH: 21
<212> TYPE: DNA
<213> ORGANISM: Artificial Sequence
<220> FEATURE:
<223> OTHER INFORMATION: PCR primer

<400> SEQUENCE: 72
caagcttgca ttcttcgttt c                                        21

<210> SEQ ID NO 73
<211> LENGTH: 42
<212> TYPE: DNA
<213> ORGANISM: Artificial Sequence
<220> FEATURE:
<223> OTHER INFORMATION: PCR primer -continued

<400> SEQUENCE: 73
tgtaaaacga cggccagtgg gacctaatat gatgaactta ca         42

<210> SEQ ID NO 74
<211> LENGTH: 21
<212> TYPE: DNA
<213> ORGANISM: Artificial Sequence
<220> FEATURE:
<223> OTHER INFORMATION: PCR primer

<400> SEQUENCE: 74
gttcaagcat ggaaagtttg g                               21

<210> SEQ ID NO 75
<211> LENGTH: 38
<212> TYPE: DNA
<213> ORGANISM: Artificial Sequence
<220> FEATURE:
<223> OTHER INFORMATION: PCR primer

<400> SEQUENCE: 75
tgtaaaacga cggccagtcg acgtcgtctt ctgttaat             38

<210> SEQ ID NO 76
<211> LENGTH: 21
<212> TYPE: DNA
<213> ORGANISM: Artificial Sequence
<220> FEATURE:
<223> OTHER INFORMATION: PCR primer

<400> SEQUENCE: 76
ggcactccta acctgttttc c                               21

<210> SEQ ID NO 77
<211> LENGTH: 42
<212> TYPE: DNA
<213> ORGANISM: Artificial Sequence
<220> FEATURE:
<223> OTHER INFORMATION: PCR primer

<400> SEQUENCE: 77
tgtaaaacga cggccagttc aaatttggtt gtgtgtaatt tt        42

<210> SEQ ID NO 78
<211> LENGTH: 21
<212> TYPE: DNA
<213> ORGANISM: Artificial Sequence
<220> FEATURE:
<223> OTHER INFORMATION: PCR primer

<400> SEQUENCE: 78
catcaataag cccaatcctc a                               21

<210> SEQ ID NO 79
<211> LENGTH: 39
<212> TYPE: DNA
<213> ORGANISM: Artificial Sequence
<220> FEATURE:
<223> OTHER INFORMATION: PCR primer

<400> SEQUENCE: 79
tgtaaaacga cggccagtcc cttacccctg ttttcattt            39

<210> SEQ ID NO 80
<211> LENGTH: 21

```
<212> TYPE: DNA
<213> ORGANISM: Artificial Sequence
<220> FEATURE:
<223> OTHER INFORMATION: PCR primer

<400> SEQUENCE: 80
acacaacatt ttgtcggttg a                                              21

<210> SEQ ID NO 81
<211> LENGTH: 39
<212> TYPE: DNA
<213> ORGANISM: Artificial Sequence
<220> FEATURE:
<223> OTHER INFORMATION: PCR primer

<400> SEQUENCE: 81
tgtaaaacga cggccagtaa attcaccacc acccactttt                          39

<210> SEQ ID NO 82
<211> LENGTH: 21
<212> TYPE: DNA
<213> ORGANISM: Artificial Sequence
<220> FEATURE:
<223> OTHER INFORMATION: PCR primer

<400> SEQUENCE: 82
aatgggtttg gagaaaggat g                                              21

<210> SEQ ID NO 83
<211> LENGTH: 42
<212> TYPE: DNA
<213> ORGANISM: Artificial Sequence
<220> FEATURE:
<223> OTHER INFORMATION: PCR primer

<400> SEQUENCE: 83
tgtaaaacga cggccagtga cgaactcttt tcttttctga ca                       42

<210> SEQ ID NO 84
<211> LENGTH: 21
<212> TYPE: DNA
<213> ORGANISM: Artificial Sequence
<220> FEATURE:
<223> OTHER INFORMATION: PCR primer

<400> SEQUENCE: 84
tgacagtttc cacaatcctc c                                              21

<210> SEQ ID NO 85
<211> LENGTH: 40
<212> TYPE: DNA
<213> ORGANISM: Artificial Sequence
<220> FEATURE:
<223> OTHER INFORMATION: PCR primer

<400> SEQUENCE: 85
tgtaaaacga cggccagttc tgttctgttc tgttcctcca                          40

<210> SEQ ID NO 86
<211> LENGTH: 21
<212> TYPE: DNA
<213> ORGANISM: Artificial Sequence
<220> FEATURE:
<223> OTHER INFORMATION: PCR primer

<400> SEQUENCE: 86
tgacagtttc cacaatcctc c                                              21
```

<210> SEQ ID NO 87
<211> LENGTH: 39
<212> TYPE: DNA
<213> ORGANISM: Artificial Sequence
<220> FEATURE:
<223> OTHER INFORMATION: PCR primer

<400> SEQUENCE: 87
tgtaaaacga cggccagtta attcgaggag gattgtgga                                    39

<210> SEQ ID NO 88
<211> LENGTH: 21
<212> TYPE: DNA
<213> ORGANISM: Artificial Sequence
<220> FEATURE:
<223> OTHER INFORMATION: PCR primer

<400> SEQUENCE: 88
atacaccata gcacgagacg c                                                       21

<210> SEQ ID NO 89
<211> LENGTH: 39
<212> TYPE: DNA
<213> ORGANISM: Artificial Sequence
<220> FEATURE:
<223> OTHER INFORMATION: PCR primer

<400> SEQUENCE: 89
tgtaaaacga cggccagtcc tccttatcct cctccctct                                    39

<210> SEQ ID NO 90
<211> LENGTH: 21
<212> TYPE: DNA
<213> ORGANISM: Artificial Sequence
<220> FEATURE:
<223> OTHER INFORMATION: PCR primer

<400> SEQUENCE: 90
tgaattcagg gtcaaggtca c                                                       21

<210> SEQ ID NO 91
<211> LENGTH: 39
<212> TYPE: DNA
<213> ORGANISM: Artificial Sequence
<220> FEATURE:
<223> OTHER INFORMATION: PCR primer

<400> SEQUENCE: 91
tgtaaaacga cggccagtaa cagagttgtt catggctgg                                    39

<210> SEQ ID NO 92
<211> LENGTH: 21
<212> TYPE: DNA
<213> ORGANISM: Artificial Sequence
<220> FEATURE:
<223> OTHER INFORMATION: PCR primer

<400> SEQUENCE: 92
agcaccaaaa ttaaacaccc c                                                       21

<210> SEQ ID NO 93
<211> LENGTH: 40
<212> TYPE: DNA
<213> ORGANISM: Artificial Sequence
<220> FEATURE:
<223> OTHER INFORMATION: PCR primer

```
<400> SEQUENCE: 93
tgtaaaacga cggccagttg aaggaagaag gaagaaggaa                              40

<210> SEQ ID NO 94
<211> LENGTH: 21
<212> TYPE: DNA
<213> ORGANISM: Artificial Sequence
<220> FEATURE:
<223> OTHER INFORMATION: PCR primer

<400> SEQUENCE: 94
acaagaagaa gattgcgacg a                                                  21

<210> SEQ ID NO 95
<211> LENGTH: 39
<212> TYPE: DNA
<213> ORGANISM: Artificial Sequence
<220> FEATURE:
<223> OTHER INFORMATION: PCR primer

<400> SEQUENCE: 95
tgtaaaacga cggccagtat ctctgctgtt gcctaatgc                               39

<210> SEQ ID NO 96
<211> LENGTH: 22
<212> TYPE: DNA
<213> ORGANISM: Artificial Sequence
<220> FEATURE:
<223> OTHER INFORMATION: PCR primer

<400> SEQUENCE: 96
tcctctttcc aaaggaaaca aa                                                 22

<210> SEQ ID NO 97
<211> LENGTH: 41
<212> TYPE: DNA
<213> ORGANISM: Artificial Sequence
<220> FEATURE:
<223> OTHER INFORMATION: PCR primer

<400> SEQUENCE: 97
tgtaaaacga cggccagttg atttcacttt agcatcttgt g                            41

<210> SEQ ID NO 98
<211> LENGTH: 21
<212> TYPE: DNA
<213> ORGANISM: Artificial Sequence
<220> FEATURE:
<223> OTHER INFORMATION: PCR primer

<400> SEQUENCE: 98
ggatccatta ccagacagtg c                                                  21

<210> SEQ ID NO 99
<211> LENGTH: 41
<212> TYPE: DNA
<213> ORGANISM: Artificial Sequence
<220> FEATURE:
<223> OTHER INFORMATION: PCR primer

<400> SEQUENCE: 99
tgtaaaacga cggccagtca agaaccagat catcaacaac a                            41

<210> SEQ ID NO 100
<211> LENGTH: 21
```

```
<212> TYPE: DNA
<213> ORGANISM: Artificial Sequence
<220> FEATURE:
<223> OTHER INFORMATION: PCR primer

<400> SEQUENCE: 100
aatttggact ttgattgtgc g                                         21

<210> SEQ ID NO 101
<211> LENGTH: 39
<212> TYPE: DNA
<213> ORGANISM: Artificial Sequence
<220> FEATURE:
<223> OTHER INFORMATION: PCR primer

<400> SEQUENCE: 101
tgtaaaacga cggccagtca caacacacgc taccctaca                      39

<210> SEQ ID NO 102
<211> LENGTH: 21
<212> TYPE: DNA
<213> ORGANISM: Artificial Sequence
<220> FEATURE:
<223> OTHER INFORMATION: PCR primer

<400> SEQUENCE: 102
atgctttctg tgttttggtg g                                         21

<210> SEQ ID NO 103
<211> LENGTH: 41
<212> TYPE: DNA
<213> ORGANISM: Artificial Sequence
<220> FEATURE:
<223> OTHER INFORMATION: PCR primer

<400> SEQUENCE: 103
tgtaaaacga cggccagttt gaaatagtgc aagaagaacc c                   41

<210> SEQ ID NO 104
<211> LENGTH: 21
<212> TYPE: DNA
<213> ORGANISM: Artificial Sequence
<220> FEATURE:
<223> OTHER INFORMATION: PCR primer

<400> SEQUENCE: 104
ggagatgaag aaggagatgg g                                         21

<210> SEQ ID NO 105
<211> LENGTH: 42
<212> TYPE: DNA
<213> ORGANISM: Artificial Sequence
<220> FEATURE:
<223> OTHER INFORMATION: PCR primer

<400> SEQUENCE: 105
tgtaaaacga cggccagttc tactttctt gtgtgtgatt cc                   42

<210> SEQ ID NO 106
<211> LENGTH: 21
<212> TYPE: DNA
<213> ORGANISM: Artificial Sequence
<220> FEATURE:
<223> OTHER INFORMATION: PCR primer

<400> SEQUENCE: 106
tagcctcaag cttcaatcca a                                         21
```

<210> SEQ ID NO 107
<211> LENGTH: 39
<212> TYPE: DNA
<213> ORGANISM: Artificial Sequence
<220> FEATURE:
<223> OTHER INFORMATION: PCR primer

<400> SEQUENCE: 107
tgtaaaacga cggccagttc tggaattgga agagattgc                        39

<210> SEQ ID NO 108
<211> LENGTH: 21
<212> TYPE: DNA
<213> ORGANISM: Artificial Sequence
<220> FEATURE:
<223> OTHER INFORMATION: PCR primer

<400> SEQUENCE: 108
ggccgtattt cgctctttct a                                           21

<210> SEQ ID NO 109
<211> LENGTH: 42
<212> TYPE: DNA
<213> ORGANISM: Artificial Sequence
<220> FEATURE:
<223> OTHER INFORMATION: PCR primer

<400> SEQUENCE: 109
tgtaaaacga cggccagtct ttttcattct gtaacacata tt                    42

<210> SEQ ID NO 110
<211> LENGTH: 21
<212> TYPE: DNA
<213> ORGANISM: Artificial Sequence
<220> FEATURE:
<223> OTHER INFORMATION: PCR primer

<400> SEQUENCE: 110
ccacaatttc tgaaccctca a                                           21

<210> SEQ ID NO 111
<211> LENGTH: 41
<212> TYPE: DNA
<213> ORGANISM: Artificial Sequence
<220> FEATURE:
<223> OTHER INFORMATION: PCR primer

<400> SEQUENCE: 111
tgtaaaacga cggccagttg attggtcaac tgagattcaa a                     41

<210> SEQ ID NO 112
<211> LENGTH: 21
<212> TYPE: DNA
<213> ORGANISM: Artificial Sequence
<220> FEATURE:
<223> OTHER INFORMATION: PCR primer

<400> SEQUENCE: 112
gacacaacat caccaccatc a                                           21

<210> SEQ ID NO 113
<211> LENGTH: 40
<212> TYPE: DNA
<213> ORGANISM: Artificial Sequence
<220> FEATURE:
<223> OTHER INFORMATION: PCR primer

<400> SEQUENCE: 113
tgtaaaacga cggccagtgg agagagcaaa gtctcttcaa          40

<210> SEQ ID NO 114
<211> LENGTH: 22
<212> TYPE: DNA
<213> ORGANISM: Artificial Sequence
<220> FEATURE:
<223> OTHER INFORMATION: PCR primer

<400> SEQUENCE: 114
tgtcacttgt tctggtcctt ct          22

<210> SEQ ID NO 115
<211> LENGTH: 40
<212> TYPE: DNA
<213> ORGANISM: Artificial Sequence
<220> FEATURE:
<223> OTHER INFORMATION: PCR primer

<400> SEQUENCE: 115
tgtaaaacga cggccagtac ttatcagaat ctaattgggc          40

<210> SEQ ID NO 116
<211> LENGTH: 21
<212> TYPE: DNA
<213> ORGANISM: Artificial Sequence
<220> FEATURE:
<223> OTHER INFORMATION: PCR primer

<400> SEQUENCE: 116
cgttgttgat gaagttggtg a          21

<210> SEQ ID NO 117
<211> LENGTH: 42
<212> TYPE: DNA
<213> ORGANISM: Artificial Sequence
<220> FEATURE:
<223> OTHER INFORMATION: PCR primer

<400> SEQUENCE: 117
tgtaaaacga cggccagttt catgaatttg cttctattgc at          42

<210> SEQ ID NO 118
<211> LENGTH: 21
<212> TYPE: DNA
<213> ORGANISM: Artificial Sequence
<220> FEATURE:
<223> OTHER INFORMATION: PCR primer

<400> SEQUENCE: 118
aaatttcttt ccattggctc c          21

<210> SEQ ID NO 119
<211> LENGTH: 42
<212> TYPE: DNA
<213> ORGANISM: Artificial Sequence
<220> FEATURE:
<223> OTHER INFORMATION: PCR primer

<400> SEQUENCE: 119
tgtaaaacga cggccagttt gacaaatatc atccttagat cg          42

<210> SEQ ID NO 120
<211> LENGTH: 22

```
<212> TYPE: DNA
<213> ORGANISM: Artificial Sequence
<220> FEATURE:
<223> OTHER INFORMATION: PCR primer

<400> SEQUENCE: 120
ttgttccatt gttttttgtga gg                                              22

<210> SEQ ID NO 121
<211> LENGTH: 38
<212> TYPE: DNA
<213> ORGANISM: Artificial Sequence
<220> FEATURE:
<223> OTHER INFORMATION: PCR primer

<400> SEQUENCE: 121
tgtaaaacga cggccagtac attctcttcg tgccctcc                              38

<210> SEQ ID NO 122
<211> LENGTH: 21
<212> TYPE: DNA
<213> ORGANISM: Artificial Sequence
<220> FEATURE:
<223> OTHER INFORMATION: PCR primer

<400> SEQUENCE: 122
cgcagcacat gtaacttgaa a                                                21

<210> SEQ ID NO 123
<211> LENGTH: 39
<212> TYPE: DNA
<213> ORGANISM: Artificial Sequence
<220> FEATURE:
<223> OTHER INFORMATION: PCR primer

<400> SEQUENCE: 123
tgtaaaacga cggccagttt tcatcaacat caaacaccg                             39

<210> SEQ ID NO 124
<211> LENGTH: 21
<212> TYPE: DNA
<213> ORGANISM: Artificial Sequence
<220> FEATURE:
<223> OTHER INFORMATION: PCR primer

<400> SEQUENCE: 124 agcttttca acgagttcag c                                                 21

<210> SEQ ID NO 125
<211> LENGTH: 41
<212> TYPE: DNA
<213> ORGANISM: Artificial Sequence
<220> FEATURE:
<223> OTHER INFORMATION: PCR primer

<400> SEQUENCE: 125
tgtaaaacga cggccagttt cgattctcaa ttcttcactc a                          41

<210> SEQ ID NO 126
<211> LENGTH: 21
<212> TYPE: DNA
<213> ORGANISM: Artificial Sequence
<220> FEATURE:
<223> OTHER INFORMATION: PCR primer

<400> SEQUENCE: 126
cataaacccg cattgagaca t                                                21
```

<210> SEQ ID NO 127
<211> LENGTH: 37
<212> TYPE: DNA
<213> ORGANISM: Artificial Sequence
<220> FEATURE:
<223> OTHER INFORMATION: PCR primer

<400> SEQUENCE: 127
tgtaaaacga cggccagtcc gattggactc ggaactt                37

<210> SEQ ID NO 128
<211> LENGTH: 21
<212> TYPE: DNA
<213> ORGANISM: Artificial Sequence
<220> FEATURE:
<223> OTHER INFORMATION: PCR primer

<400> SEQUENCE: 128
ttcttggctt cgacttcttc a                21

<210> SEQ ID NO 129
<211> LENGTH: 39
<212> TYPE: DNA
<213> ORGANISM: Artificial Sequence
<220> FEATURE:
<223> OTHER INFORMATION: PCR primer

<400> SEQUENCE: 129
tgtaaaacga cggccagttc tgtaacacag gcagagtcg                39

<210> SEQ ID NO 130
<211> LENGTH: 21
<212> TYPE: DNA
<213> ORGANISM: Artificial Sequence
<220> FEATURE:
<223> OTHER INFORMATION: PCR primer

<400> SEQUENCE: 130
ggatttcgtt tgggttcatt t                21

<210> SEQ ID NO 131
<211> LENGTH: 39
<212> TYPE: DNA
<213> ORGANISM: Artificial Sequence
<220> FEATURE:
<223> OTHER INFORMATION: PCR primer

<400> SEQUENCE: 131
tgtaaaacga cggccagtcc cctaaattcc caattcttc                39

<210> SEQ ID NO 132
<211> LENGTH: 21
<212> TYPE: DNA
<213> ORGANISM: Artificial Sequence
<220> FEATURE:
<223> OTHER INFORMATION: PCR primer

<400> SEQUENCE: 132
gtctacaccc tgtaatccgc a                21

<210> SEQ ID NO 133
<211> LENGTH: 39
<212> TYPE: DNA
<213> ORGANISM: Artificial Sequence
<220> FEATURE:
<223> OTHER INFORMATION: PCR primer

```
<400> SEQUENCE: 133
tgtaaaacga cggccagtac tgagaaaagg aaactgccc                        39

<210> SEQ ID NO 134
<211> LENGTH: 21
<212> TYPE: DNA
<213> ORGANISM: Artificial Sequence
<220> FEATURE:
<223> OTHER INFORMATION: PCR primer

<400> SEQUENCE: 134
tcatcaagca ttgcactcaa g                                           21

<210> SEQ ID NO 135
<211> LENGTH: 39
<212> TYPE: DNA
<213> ORGANISM: Artificial Sequence
<220> FEATURE:
<223> OTHER INFORMATION: PCR primer

<400> SEQUENCE: 135
tgtaaaacga cggccagttc cacaaaaggg tgtgagaaa                        39

<210> SEQ ID NO 136
<211> LENGTH: 22
<212> TYPE: DNA
<213> ORGANISM: Artificial Sequence
<220> FEATURE:
<223> OTHER INFORMATION: PCR primer

<400> SEQUENCE: 136
aaaggtggtt cttccttatt ca                                          22

<210> SEQ ID NO 137
<211> LENGTH: 38
<212> TYPE: DNA
<213> ORGANISM: Artificial Sequence
<220> FEATURE:
<223> OTHER INFORMATION: PCR primer

<400> SEQUENCE: 137
tgtaaaacga cggccagtat ggaatcagca tacagggc                         38

<210> SEQ ID NO 138
<211> LENGTH: 21
<212> TYPE: DNA
<213> ORGANISM: Artificial Sequence
<220> FEATURE:
<223> OTHER INFORMATION: PCR primer

<400> SEQUENCE: 138
ctcggttgtc atcaccaaga t                                           21

<210> SEQ ID NO 139
<211> LENGTH: 39
<212> TYPE: DNA
<213> ORGANISM: Artificial Sequence
<220> FEATURE:
<223> OTHER INFORMATION: PCR primer

<400> SEQUENCE: 139
tgtaaaacga cggccagtag ctctgttttg tcctgcttg                        39

<210> SEQ ID NO 140
<211> LENGTH: 21
```

```
<212> TYPE: DNA
<213> ORGANISM: Artificial Sequence
<220> FEATURE:
<223> OTHER INFORMATION: PCR primer

<400> SEQUENCE: 140
cgaacaagat taccgagatg g                                          21

<210> SEQ ID NO 141
<211> LENGTH: 40
<212> TYPE: DNA
<213> ORGANISM: Artificial Sequence
<220> FEATURE:
<223> OTHER INFORMATION: PCR primer

<400> SEQUENCE: 141
tgtaaaacga cggccagttc ctaatacccc attcattggt                      40

<210> SEQ ID NO 142
<211> LENGTH: 21
<212> TYPE: DNA
<213> ORGANISM: Artificial Sequence
<220> FEATURE:
<223> OTHER INFORMATION: PCR primer

<400> SEQUENCE: 142
caggaacata actgtgaccc g                                          21

<210> SEQ ID NO 143
<211> LENGTH: 39
<212> TYPE: DNA
<213> ORGANISM: Artificial Sequence
<220> FEATURE:
<223> OTHER INFORMATION: PCR primer

<400> SEQUENCE: 143
tgtaaaacga cggccagttg tcgaaatatc atgattggg                       39

<210> SEQ ID NO 144
<211> LENGTH: 21
<212> TYPE: DNA
<213> ORGANISM: Artificial Sequence
<220> FEATURE:
<223> OTHER INFORMATION: PCR primer

<400> SEQUENCE: 144
attcgtaggc cgacaatttt t                                          21

<210> SEQ ID NO 145
<211> LENGTH: 42
<212> TYPE: DNA
<213> ORGANISM: Artificial Sequence
<220> FEATURE:
<223> OTHER INFORMATION: PCR primer

<400> SEQUENCE: 145
tgtaaaacga cggccagtaa gattagggtt tgagtaaggg aa                   42

<210> SEQ ID NO 146
<211> LENGTH: 21
<212> TYPE: DNA
<213> ORGANISM: Artificial Sequence
<220> FEATURE:
<223> OTHER INFORMATION: PCR primer

<400> SEQUENCE: 146
gcctttaggc caatcagaga c                                          21
```

<210> SEQ ID NO 147
<211> LENGTH: 41
<212> TYPE: DNA
<213> ORGANISM: Artificial Sequence
<220> FEATURE:
<223> OTHER INFORMATION: PCR primer

<400> SEQUENCE: 147
tgtaaaacga cggccagtgg tagtacttcc ttcactcttc t           41

<210> SEQ ID NO 148
<211> LENGTH: 21
<212> TYPE: DNA
<213> ORGANISM: Artificial Sequence
<220> FEATURE:
<223> OTHER INFORMATION: PCR primer

<400> SEQUENCE: 148
acatcttctg gaagacccgt t                                  21

<210> SEQ ID NO 149
<211> LENGTH: 39
<212> TYPE: DNA
<213> ORGANISM: Artificial Sequence
<220> FEATURE:
<223> OTHER INFORMATION: PCR primer

<400> SEQUENCE: 149
tgtaaaacga cggccagtac tccatcaact ggttcaccg              39

<210> SEQ ID NO 150
<211> LENGTH: 21
<212> TYPE: DNA
<213> ORGANISM: Artificial Sequence
<220> FEATURE:
<223> OTHER INFORMATION: PCR primer

<400> SEQUENCE: 150
cacacatcaa agcccctaaa a                                  21

<210> SEQ ID NO 151
<211> LENGTH: 42
<212> TYPE: DNA
<213> ORGANISM: Artificial Sequence
<220> FEATURE:
<223> OTHER INFORMATION: PCR primer

<400> SEQUENCE: 151
tgtaaaacga cggccagtcg aaagataaaa taattgaatc gg           42

<210> SEQ ID NO 152
<211> LENGTH: 21
<212> TYPE: DNA
<213> ORGANISM: Artificial Sequence
<220> FEATURE:
<223> OTHER INFORMATION: PCR primer

<400> SEQUENCE: 152
atctcttagc ctcgttggct c                                  21

<210> SEQ ID NO 153
<211> LENGTH: 42
<212> TYPE: DNA
<213> ORGANISM: Artificial Sequence
<220> FEATURE:
<223> OTHER INFORMATION: PCR primer

<400> SEQUENCE: 153
tgtaaaacga cggccagttg tctgttcgta tttgttgttc tg                          42

<210> SEQ ID NO 154
<211> LENGTH: 21
<212> TYPE: DNA
<213> ORGANISM: Artificial Sequence
<220> FEATURE:
<223> OTHER INFORMATION: PCR primer

<400> SEQUENCE: 154
gtcacaactg ttaccatgcc c                                                 21

<210> SEQ ID NO 155
<211> LENGTH: 40
<212> TYPE: DNA
<213> ORGANISM: Artificial Sequence
<220> FEATURE:
<223> OTHER INFORMATION: PCR primer

<400> SEQUENCE: 155
tgtaaaacga cggccagtaa gcgatttcat tagtagttgt                             40

<210> SEQ ID NO 156
<211> LENGTH: 21
<212> TYPE: DNA
<213> ORGANISM: Artificial Sequence
<220> FEATURE:
<223> OTHER INFORMATION: PCR primer

<400> SEQUENCE: 156
cagttgatgc atagaaacgc a                                                 21

<210> SEQ ID NO 157
<211> LENGTH: 39
<212> TYPE: DNA
<213> ORGANISM: Artificial Sequence
<220> FEATURE:
<223> OTHER INFORMATION: PCR primer

<400> SEQUENCE: 157
tgtaaaacga cggccagttc aaaaccttgg tgttggttg                              39

<210> SEQ ID NO 158
<211> LENGTH: 21
<212> TYPE: DNA
<213> ORGANISM: Artificial Sequence
<220> FEATURE:
<223> OTHER INFORMATION: PCR primer

<400> SEQUENCE: 158
atctgggaag tgtgacctcc t                                                 21

<210> SEQ ID NO 159
<211> LENGTH: 41
<212> TYPE: DNA
<213> ORGANISM: Artificial Sequence
<220> FEATURE:
<223> OTHER INFORMATION: PCR primer

<400> SEQUENCE: 159
tgtaaaacga cggccagtct ctttaagatt gcttctcttg c                           41

<210> SEQ ID NO 160
<211> LENGTH: 21

```
<212> TYPE: DNA
<213> ORGANISM: Artificial Sequence
<220> FEATURE:
<223> OTHER INFORMATION: PCR primer

<400> SEQUENCE: 160
catactatgg tggtggttgg g                                              21

<210> SEQ ID NO 161
<211> LENGTH: 39
<212> TYPE: DNA
<213> ORGANISM: Artificial Sequence
<220> FEATURE:
<223> OTHER INFORMATION: PCR primer

<400> SEQUENCE: 161
tgtaaaacga cggccagtac ttgttgatct ggacgatga                           39

<210> SEQ ID NO 162
<211> LENGTH: 24
<212> TYPE: DNA
<213> ORGANISM: Artificial Sequence
<220> FEATURE:
<223> OTHER INFORMATION: PCR primer

<400> SEQUENCE: 162
gcttagcatt tccattgttc taca                                           24

<210> SEQ ID NO 163
<211> LENGTH: 40
<212> TYPE: DNA
<213> ORGANISM: Artificial Sequence
<220> FEATURE:
<223> OTHER INFORMATION: PCR primer

<400> SEQUENCE: 163
tgtaaaacga cggccagtaa caacctagat tttctcgacc                          40

<210> SEQ ID NO 164
<211> LENGTH: 21
<212> TYPE: DNA
<213> ORGANISM: Artificial Sequence
<220> FEATURE:
<223> OTHER INFORMATION: PCR primer

<400> SEQUENCE: 164
tcaccagcac atgaatcaaa a                                              21

<210> SEQ ID NO 165
<211> LENGTH: 41
<212> TYPE: DNA
<213> ORGANISM: Artificial Sequence
<220> FEATURE:
<223> OTHER INFORMATION: PCR primer

<400> SEQUENCE: 165
tgtaaaacga cggccagtgc catctttatt tttggatgtc a                        41

<210> SEQ ID NO 166
<211> LENGTH: 21
<212> TYPE: DNA
<213> ORGANISM: Artificial Sequence
<220> FEATURE:
<223> OTHER INFORMATION: PCR primer

<400> SEQUENCE: 166
cctccaataa tggtggacac a                                              21
```

<210> SEQ ID NO 167
<211> LENGTH: 40
<212> TYPE: DNA
<213> ORGANISM: Artificial Sequence
<220> FEATURE:
<223> OTHER INFORMATION: PCR primer

<400> SEQUENCE: 167
tgtaaaacga cggccagttc ataatcactc actctccctt                40

<210> SEQ ID NO 168
<211> LENGTH: 21
<212> TYPE: DNA
<213> ORGANISM: Artificial Sequence
<220> FEATURE:
<223> OTHER INFORMATION: PCR primer

<400> SEQUENCE: 168
atccgcatcc aaactaggtc t                                   21

<210> SEQ ID NO 169
<211> LENGTH: 39
<212> TYPE: DNA
<213> ORGANISM: Artificial Sequence
<220> FEATURE:
<223> OTHER INFORMATION: PCR primer

<400> SEQUENCE: 169
tgtaaaacga cggccagtat tgcaatcatc ttctcccct                39

<210> SEQ ID NO 170
<211> LENGTH: 21
<212> TYPE: DNA
<213> ORGANISM: Artificial Sequence
<220> FEATURE:
<223> OTHER INFORMATION: PCR primer

<400> SEQUENCE: 170
agggttgatg cagatgttac g                                   21

<210> SEQ ID NO 171
<211> LENGTH: 42
<212> TYPE: DNA
<213> ORGANISM: Artificial Sequence
<220> FEATURE:
<223> OTHER INFORMATION: PCR primer

<400> SEQUENCE: 171
tgtaaaacga cggccagtca ctctctcact tcatttgaaa aa            42

<210> SEQ ID NO 172
<211> LENGTH: 21
<212> TYPE: DNA
<213> ORGANISM: Artificial Sequence
<220> FEATURE:
<223> OTHER INFORMATION: PCR primer

<400> SEQUENCE: 172
aaagggtaat cgaaaagcca a                                   21

<210> SEQ ID NO 173
<211> LENGTH: 39
<212> TYPE: DNA
<213> ORGANISM: Artificial Sequence
<220> FEATURE:
<223> OTHER INFORMATION: PCR primer

<400> SEQUENCE: 173
tgtaaaacga cggccagtca ggtggatgga gagagtcaa                          39

<210> SEQ ID NO 174
<211> LENGTH: 21
<212> TYPE: DNA
<213> ORGANISM: Artificial Sequence
<220> FEATURE:
<223> OTHER INFORMATION: PCR primer

<400> SEQUENCE: 174
gctgggagac aagtgttgct a                                             21

<210> SEQ ID NO 175
<211> LENGTH: 39
<212> TYPE: DNA
<213> ORGANISM: Artificial Sequence
<220> FEATURE:
<223> OTHER INFORMATION: PCR primer

<400> SEQUENCE: 175
tgtaaaacga cggccagtca ccgcctgttc tatcatgtg                          39

<210> SEQ ID NO 176
<211> LENGTH: 21
<212> TYPE: DNA
<213> ORGANISM: Artificial Sequence
<220> FEATURE:
<223> OTHER INFORMATION: PCR primer

<400> SEQUENCE: 176
acttgtccat ctccatctcc a                                             21

<210> SEQ ID NO 177
<211> LENGTH: 39
<212> TYPE: DNA
<213> ORGANISM: Artificial Sequence
<220> FEATURE:
<223> OTHER INFORMATION: PCR primer

<400> SEQUENCE: 177
tgtaaaacga cggccagtcg aggcatcttc atcttcaac                          39

<210> SEQ ID NO 178
<211> LENGTH: 21
<212> TYPE: DNA
<213> ORGANISM: Artificial Sequence
<220> FEATURE:
<223> OTHER INFORMATION: PCR primer

<400> SEQUENCE: 178
ggacggtttc gaacttctag c                                             21

<210> SEQ ID NO 179
<211> LENGTH: 39
<212> TYPE: DNA
<213> ORGANISM: Artificial Sequence
<220> FEATURE:
<223> OTHER INFORMATION: PCR primer

<400> SEQUENCE: 179
tgtaaaacga cggccagtgg aagatcacca ttttgtcca                          39

<210> SEQ ID NO 180
<211> LENGTH: 22

```
<212> TYPE: DNA
<213> ORGANISM: Artificial Sequence
<220> FEATURE:
<223> OTHER INFORMATION: PCR primer

<400> SEQUENCE: 180
aacaatatga tctggcatgt cg                                          22

<210> SEQ ID NO 181
<211> LENGTH: 41
<212> TYPE: DNA
<213> ORGANISM: Artificial Sequence
<220> FEATURE:
<223> OTHER INFORMATION: PCR primer

<400> SEQUENCE: 181
tgtaaaacga cggccagtct cttttctctt caattttcaa t                     41

<210> SEQ ID NO 182
<211> LENGTH: 21
<212> TYPE: DNA
<213> ORGANISM: Artificial Sequence
<220> FEATURE:
<223> OTHER INFORMATION: PCR primer

<400> SEQUENCE: 182
gataaagctc ccacagttcc c                                           21

<210> SEQ ID NO 183
<211> LENGTH: 40
<212> TYPE: DNA
<213> ORGANISM: Artificial Sequence
<220> FEATURE:
<223> OTHER INFORMATION: PCR primer

<400> SEQUENCE: 183
tgtaaaacga cggccagttt tccaaacttt ccttcttttg                       40

<210> SEQ ID NO 184
<211> LENGTH: 21
<212> TYPE: DNA
<213> ORGANISM: Artificial Sequence
<220> FEATURE:
<223> OTHER INFORMATION: PCR primer

<400> SEQUENCE: 184
aggtacaagc catgatgtcc a                                           21

<210> SEQ ID NO 185
<211> LENGTH: 39
<212> TYPE: DNA
<213> ORGANISM: Artificial Sequence
<220> FEATURE:
<223> OTHER INFORMATION: PCR primer

<400> SEQUENCE: 185
tgtaaaacga cggccagtca acctacgacg ttgtggaac                        39

<210> SEQ ID NO 186
<211> LENGTH: 21
<212> TYPE: DNA
<213> ORGANISM: Artificial Sequence
<220> FEATURE:
<223> OTHER INFORMATION: PCR primer

<400> SEQUENCE: 186
tcatggagcc agtcttcatc t                                           21
```

```
<210> SEQ ID NO 187
<211> LENGTH: 42
<212> TYPE: DNA
<213> ORGANISM: Artificial Sequence
<220> FEATURE:
<223> OTHER INFORMATION: PCR primer

<400> SEQUENCE: 187
tgtaaaacga cggccagtct ctctctctct ctctctctgc at                        42

<210> SEQ ID NO 188
<211> LENGTH: 22
<212> TYPE: DNA
<213> ORGANISM: Artificial Sequence
<220> FEATURE:
<223> OTHER INFORMATION: PCR primer

<400> SEQUENCE: 188
aaacactaaa gggtcatgct ca                                              22

<210> SEQ ID NO 189
<211> LENGTH: 40
<212> TYPE: DNA
<213> ORGANISM: Artificial Sequence
<220> FEATURE:
<223> OTHER INFORMATION: PCR primer

<400> SEQUENCE: 189
tgtaaaacga cggccagttg aaggaagaag gaagaaggaa                           40

<210> SEQ ID NO 190
<211> LENGTH: 21
<212> TYPE: DNA
<213> ORGANISM: Artificial Sequence
<220> FEATURE:
<223> OTHER INFORMATION: PCR primer

<400> SEQUENCE: 190
acaagaagaa gattgcgacg a                                               21

<210> SEQ ID NO 191
<211> LENGTH: 40
<212> TYPE: DNA
<213> ORGANISM: Artificial Sequence
<220> FEATURE:
<223> OTHER INFORMATION: PCR primer

<400> SEQUENCE: 191
tgtaaaacga cggccagttg gttatgttgt tccattttcc                           40

<210> SEQ ID NO 192
<211> LENGTH: 24
<212> TYPE: DNA
<213> ORGANISM: Artificial Sequence
<220> FEATURE:
<223> OTHER INFORMATION: PCR primer

<400> SEQUENCE: 192
ttcaagtagg ataataccat caga                                            24

<210> SEQ ID NO 193
<211> LENGTH: 39
<212> TYPE: DNA
<213> ORGANISM: Artificial Sequence
<220> FEATURE:
<223> OTHER INFORMATION: PCR primer
```

<400> SEQUENCE: 193
tgtaaaacga cggccagtgg gaaaactttt ggagagagc                    39

<210> SEQ ID NO 194
<211> LENGTH: 22
<212> TYPE: DNA
<213> ORGANISM: Artificial Sequence
<220> FEATURE:
<223> OTHER INFORMATION: PCR primer

<400> SEQUENCE: 194
tgtcacttgt tctggtcctt ct                                      22

<210> SEQ ID NO 195
<211> LENGTH: 38
<212> TYPE: DNA
<213> ORGANISM: Artificial Sequence
<220> FEATURE:
<223> OTHER INFORMATION: PCR primer

<400> SEQUENCE: 195
tgtaaaacga cggccagtca cattctcttc gtgccctc                     38

<210> SEQ ID NO 196
<211> LENGTH: 21
<212> TYPE: DNA
<213> ORGANISM: Artificial Sequence
<220> FEATURE:
<223> OTHER INFORMATION: PCR primer

<400> SEQUENCE: 196
cgcagcacat gtaacttgaa a                                       21

<210> SEQ ID NO 197
<211> LENGTH: 39
<212> TYPE: DNA
<213> ORGANISM: Artificial Sequence
<220> FEATURE:
<223> OTHER INFORMATION: PCR primer

<400> SEQUENCE: 197
tgtaaaacga cggccagtgg ctcacaacaa caacaaaat                    39

<210> SEQ ID NO 198
<211> LENGTH: 21
<212> TYPE: DNA
<213> ORGANISM: Artificial Sequence
<220> FEATURE:
<223> OTHER INFORMATION: PCR primer

<400> SEQUENCE: 198
tccgaaaaag gtgacagatt g                                       21

<210> SEQ ID NO 199
<211> LENGTH: 39
<212> TYPE: DNA
<213> ORGANISM: Artificial Sequence
<220> FEATURE:
<223> OTHER INFORMATION: PCR primer

<400> SEQUENCE: 199
tgtaaaacga cggccagttg cttgattatt gctaatcgg                    39

<210> SEQ ID NO 200
<211> LENGTH: 22

```
<212> TYPE: DNA
<213> ORGANISM: Artificial Sequence
<220> FEATURE:
<223> OTHER INFORMATION: PCR primer

<400> SEQUENCE: 200
ccaaacagat ctaaagttcc ca                                               22

<210> SEQ ID NO 201
<211> LENGTH: 39
<212> TYPE: DNA
<213> ORGANISM: Artificial Sequence
<220> FEATURE:
<223> OTHER INFORMATION: PCR primer

<400> SEQUENCE: 201
tgtaaaacga cggccagtca aacaggtgac gaggtgaat                              39

<210> SEQ ID NO 202
<211> LENGTH: 21
<212> TYPE: DNA
<213> ORGANISM: Artificial Sequence
<220> FEATURE:
<223> OTHER INFORMATION: PCR primer

<400> SEQUENCE: 202
tacagttgcc catacaggag g                                                21

<210> SEQ ID NO 203
<211> LENGTH: 38
<212> TYPE: DNA
<213> ORGANISM: Artificial Sequence
<220> FEATURE:
<223> OTHER INFORMATION: PCR primer

<400> SEQUENCE: 203
tgtaaaacga cggccagtcg aggacgagtt ctggtcaa                               38

<210> SEQ ID NO 204
<211> LENGTH: 21
<212> TYPE: DNA
<213> ORGANISM: Artificial Sequence
<220> FEATURE:
<223> OTHER INFORMATION: PCR primer

<400> SEQUENCE: 204
taaatgcaag gtaggtggtg g                                                21

<210> SEQ ID NO 205
<211> LENGTH: 38
<212> TYPE: DNA
<213> ORGANISM: Artificial Sequence
<220> FEATURE:
<223> OTHER INFORMATION: PCR primer

<400> SEQUENCE: 205
tgtaaaacga cggccagtcc ctgttgaagc ttttgctg                               38

<210> SEQ ID NO 206
<211> LENGTH: 24
<212> TYPE: DNA
<213> ORGANISM: Artificial Sequence
<220> FEATURE:
<223> OTHER INFORMATION: PCR primer

<400> SEQUENCE: 206
aggcttggta gatactcata acat                                             24
```

<210> SEQ ID NO 207
<211> LENGTH: 39
<212> TYPE: DNA
<213> ORGANISM: Artificial Sequence
<220> FEATURE:
<223> OTHER INFORMATION: PCR primer

<400> SEQUENCE: 207
tgtaaaacga cggccagtta atttcattcg cgatcacac        39

<210> SEQ ID NO 208
<211> LENGTH: 21
<212> TYPE: DNA
<213> ORGANISM: Artificial Sequence
<220> FEATURE:
<223> OTHER INFORMATION: PCR primer

<400> SEQUENCE: 208
aagaccaaga ggaatcaccg t        21

<210> SEQ ID NO 209
<211> LENGTH: 39
<212> TYPE: DNA
<213> ORGANISM: Artificial Sequence
<220> FEATURE:
<223> OTHER INFORMATION: PCR primer

<400> SEQUENCE: 209
tgtaaaacga cggccagtac ccccttcaaa accctatct        39

<210> SEQ ID NO 210
<211> LENGTH: 21
<212> TYPE: DNA
<213> ORGANISM: Artificial Sequence
<220> FEATURE:
<223> OTHER INFORMATION: PCR primer

<400> SEQUENCE: 210
tacaggttgg gaatcaggtt g        21

<210> SEQ ID NO 211
<211> LENGTH: 42
<212> TYPE: DNA
<213> ORGANISM: Artificial Sequence
<220> FEATURE:
<223> OTHER INFORMATION: PCR primer

<400> SEQUENCE: 211
tgtaaaacga cggccagtcc gcctcaaata gttataaact tc        42

<210> SEQ ID NO 212
<211> LENGTH: 21
<212> TYPE: DNA
<213> ORGANISM: Artificial Sequence
<220> FEATURE:
<223> OTHER INFORMATION: PCR primer

<400> SEQUENCE: 212
tgaatgtgag gaagtgggtt t        21

<210> SEQ ID NO 213
<211> LENGTH: 39
<212> TYPE: DNA
<213> ORGANISM: Artificial Sequence
<220> FEATURE:
<223> OTHER INFORMATION: PCR primer

```
<400> SEQUENCE: 213
tgtaaaacga cggccagtcg aacaagacga agaagatgc                              39

<210> SEQ ID NO 214
<211> LENGTH: 21
<212> TYPE: DNA
<213> ORGANISM: Artificial Sequence
<220> FEATURE:
<223> OTHER INFORMATION: PCR primer

<400> SEQUENCE: 214
gatgatgacg aggacgaaag a                                                 21

<210> SEQ ID NO 215
<211> LENGTH: 39
<212> TYPE: DNA
<213> ORGANISM: Artificial Sequence
<220> FEATURE:
<223> OTHER INFORMATION: PCR primer

<400> SEQUENCE: 215
tgtaaaacga cggccagtac aacaagggaa agcatagca                              39

<210> SEQ ID NO 216
<211> LENGTH: 21
<212> TYPE: DNA
<213> ORGANISM: Artificial Sequence
<220> FEATURE:
<223> OTHER INFORMATION: PCR primer

<400> SEQUENCE: 216
cttcatcctc ctcttgctcc t                                                 21

<210> SEQ ID NO 217
<211> LENGTH: 39
<212> TYPE: DNA
<213> ORGANISM: Artificial Sequence
<220> FEATURE:
<223> OTHER INFORMATION: PCR primer

<400> SEQUENCE: 217
tgtaaaacga cggccagtgg tttcgcttgg aattctgat                              39

<210> SEQ ID NO 218
<211> LENGTH: 21
<212> TYPE: DNA
<213> ORGANISM: Artificial Sequence
<220> FEATURE:
<223> OTHER INFORMATION: PCR primer

<400> SEQUENCE: 218
agtactattg caatggcgtg g                                                 21

<210> SEQ ID NO 219
<211> LENGTH: 39
<212> TYPE: DNA
<213> ORGANISM: Artificial Sequence
<220> FEATURE:
<223> OTHER INFORMATION: PCR primer

<400> SEQUENCE: 219
tgtaaaacga cggccagttt ggctttgatt gcttcaact                              39

<210> SEQ ID NO 220
<211> LENGTH: 21
```

```
<212> TYPE: DNA
<213> ORGANISM: Artificial Sequence
<220> FEATURE:
<223> OTHER INFORMATION: PCR primer

<400> SEQUENCE: 220
atcaagatcg actgaaccac g                                           21

<210> SEQ ID NO 221
<211> LENGTH: 40
<212> TYPE: DNA
<213> ORGANISM: Artificial Sequence
<220> FEATURE:
<223> OTHER INFORMATION: PCR primer

<400> SEQUENCE: 221
tgtaaaacga cggccagtgc acatgacaag aggactaagc                       40

<210> SEQ ID NO 222
<211> LENGTH: 21
<212> TYPE: DNA
<213> ORGANISM: Artificial Sequence
<220> FEATURE:
<223> OTHER INFORMATION: PCR primer

<400> SEQUENCE: 222
acaacatttc ctccaccatg a                                           21

<210> SEQ ID NO 223
<211> LENGTH: 39
<212> TYPE: DNA
<213> ORGANISM: Artificial Sequence
<220> FEATURE:
<223> OTHER INFORMATION: PCR primer

<400> SEQUENCE: 223
tgtaaaacga cggccagtca acaatgctgc aaatgaaag                        39

<210> SEQ ID NO 224
<211> LENGTH: 21
<212> TYPE: DNA
<213> ORGANISM: Artificial Sequence
<220> FEATURE:
<223> OTHER INFORMATION: PCR primer

<400> SEQUENCE: 224
tccaactcct cttggttttt g                                           21

<210> SEQ ID NO 225
<211> LENGTH: 38
<212> TYPE: DNA
<213> ORGANISM: Artificial Sequence
<220> FEATURE:
<223> OTHER INFORMATION: PCR primer

<400> SEQUENCE: 225
tgtaaaacga cggccagtct ccatcaactg gttcaccg                         38

<210> SEQ ID NO 226
<211> LENGTH: 21
<212> TYPE: DNA
<213> ORGANISM: Artificial Sequence
<220> FEATURE:
<223> OTHER INFORMATION: PCR primer

<400> SEQUENCE: 226
cacacatcaa agcccctaaa a                                           21
```

<210> SEQ ID NO 227
<211> LENGTH: 40
<212> TYPE: DNA
<213> ORGANISM: Artificial Sequence
<220> FEATURE:
<223> OTHER INFORMATION: PCR primer

<400> SEQUENCE: 227
tgtaaaacga cggccagtcc aaaccctagg agtctgaggt                    40

<210> SEQ ID NO 228
<211> LENGTH: 24
<212> TYPE: DNA
<213> ORGANISM: Artificial Sequence
<220> FEATURE:
<223> OTHER INFORMATION: PCR primer

<400> SEQUENCE: 228
tgcatgtaat atctatcttt ggaa                                    24

<210> SEQ ID NO 229
<211> LENGTH: 39
<212> TYPE: DNA
<213> ORGANISM: Artificial Sequence
<220> FEATURE:
<223> OTHER INFORMATION: PCR primer

<400> SEQUENCE: 229
tgtaaaacga cggccagtca acacaatcat tttgggagc                    39

<210> SEQ ID NO 230
<211> LENGTH: 21
<212> TYPE: DNA
<213> ORGANISM: Artificial Sequence
<220> FEATURE:
<223> OTHER INFORMATION: PCR primer

<400> SEQUENCE: 230
atttttccac ttctggtggg a                                       21

<210> SEQ ID NO 231
<211> LENGTH: 38
<212> TYPE: DNA
<213> ORGANISM: Artificial Sequence
<220> FEATURE:
<223> OTHER INFORMATION: PCR primer

<400> SEQUENCE: 231
tgtaaaacga cggccagtag tatggtggca gaggcaag                     38

<210> SEQ ID NO 232
<211> LENGTH: 21
<212> TYPE: DNA
<213> ORGANISM: Artificial Sequence
<220> FEATURE:
<223> OTHER INFORMATION: PCR primer

<400> SEQUENCE: 232
agagaaacgt tctgtttggc a                                       21

<210> SEQ ID NO 233
<211> LENGTH: 41
<212> TYPE: DNA
<213> ORGANISM: Artificial Sequence
<220> FEATURE:
<223> OTHER INFORMATION: PCR primer

<400> SEQUENCE: 233
tgtaaaacga cggccagtaa aggaagggtc tttatcgaga g          41

<210> SEQ ID NO 234
<211> LENGTH: 21
<212> TYPE: DNA
<213> ORGANISM: Artificial Sequence
<220> FEATURE:
<223> OTHER INFORMATION: PCR primer

<400> SEQUENCE: 234
gggttctgtt ccaaacagtg a          21

<210> SEQ ID NO 235
<211> LENGTH: 42
<212> TYPE: DNA
<213> ORGANISM: Artificial Sequence
<220> FEATURE:
<223> OTHER INFORMATION: PCR primer

<400> SEQUENCE: 235
tgtaaaacga cggccagttc tctctgataa taattctttg aa          42

<210> SEQ ID NO 236
<211> LENGTH: 21
<212> TYPE: DNA
<213> ORGANISM: Artificial Sequence
<220> FEATURE:
<223> OTHER INFORMATION: PCR primer

<400> SEQUENCE: 236
atctcttagc ctcgttggct c          21

<210> SEQ ID NO 237
<211> LENGTH: 42
<212> TYPE: DNA
<213> ORGANISM: Artificial Sequence
<220> FEATURE:
<223> OTHER INFORMATION: PCR primer

<400> SEQUENCE: 237
tgtaaaacga cggccagtaa gataaaataa ttgaatcggt tg          42

<210> SEQ ID NO 238
<211> LENGTH: 21
<212> TYPE: DNA
<213> ORGANISM: Artificial Sequence
<220> FEATURE:
<223> OTHER INFORMATION: PCR primer

<400> SEQUENCE: 238
atctcttagc ctcgttggct c          21

<210> SEQ ID NO 239
<211> LENGTH: 40
<212> TYPE: DNA
<213> ORGANISM: Artificial Sequence
<220> FEATURE:
<223> OTHER INFORMATION: PCR primer

<400> SEQUENCE: 239
tgtaaaacga cggccagttg ctgtagcttt gaacttgtga          40

<210> SEQ ID NO 240
<211> LENGTH: 24

```
<212> TYPE: DNA
<213> ORGANISM: Artificial Sequence
<220> FEATURE:
<223> OTHER INFORMATION: PCR primer

<400> SEQUENCE: 240
cgagaaaatt aatatcactc tgaa                                          24

<210> SEQ ID NO 241
<211> LENGTH: 39
<212> TYPE: DNA
<213> ORGANISM: Artificial Sequence
<220> FEATURE:
<223> OTHER INFORMATION: PCR primer

<400> SEQUENCE: 241
tgtaaaacga cggccagtcc tgatggtcat cactaagcc                          39

<210> SEQ ID NO 242
<211> LENGTH: 23
<212> TYPE: DNA
<213> ORGANISM: Artificial Sequence
<220> FEATURE:
<223> OTHER INFORMATION: PCR primer

<400> SEQUENCE: 242
tcttgttgat ataatctacg gaa                                           23

<210> SEQ ID NO 243
<211> LENGTH: 38
<212> TYPE: DNA
<213> ORGANISM: Artificial Sequence
<220> FEATURE:
<223> OTHER INFORMATION: PCR primer

<400> SEQUENCE: 243
tgtaaaacga cggccagtac agcgacagca gcgacact                           38

<210> SEQ ID NO 244
<211> LENGTH: 21
<212> TYPE: DNA
<213> ORGANISM: Artificial Sequence
<220> FEATURE:
<223> OTHER INFORMATION: PCR primer

<400> SEQUENCE: 244
caggtacgtg aaaactccca a                                             21

<210> SEQ ID NO 245
<211> LENGTH: 39
<212> TYPE: DNA
<213> ORGANISM: Artificial Sequence
<220> FEATURE:
<223> OTHER INFORMATION: PCR primer

<400> SEQUENCE: 245
tgtaaaacga cggccagttt tcaaatccaa gtggtggag                          39

<210> SEQ ID NO 246
<211> LENGTH: 21
<212> TYPE: DNA
<213> ORGANISM: Artificial Sequence
<220> FEATURE:
<223> OTHER INFORMATION: PCR primer

<400> SEQUENCE: 246
tgaggcttaa ccttaggagg c                                             21
```

```
<210> SEQ ID NO 247
<211> LENGTH: 40
<212> TYPE: DNA
<213> ORGANISM: Artificial Sequence
<220> FEATURE:
<223> OTHER INFORMATION: PCR primer

<400> SEQUENCE: 247
tgtaaaacga cggccagttt tgataaacca atctcccaca                              40

<210> SEQ ID NO 248
<211> LENGTH: 21
<212> TYPE: DNA
<213> ORGANISM: Artificial Sequence
<220> FEATURE:
<223> OTHER INFORMATION: PCR primer

<400> SEQUENCE: 248
gggacccaat aaccgaaaat a                                                  21

<210> SEQ ID NO 249
<211> LENGTH: 39
<212> TYPE: DNA
<213> ORGANISM: Artificial Sequence
<220> FEATURE:
<223> OTHER INFORMATION: PCR primer

<400> SEQUENCE: 249
tgtaaaacga cggccagtca gggttaccag aagggtcac                               39

<210> SEQ ID NO 250
<211> LENGTH: 21
<212> TYPE: DNA
<213> ORGANISM: Artificial Sequence
<220> FEATURE:
<223> OTHER INFORMATION: PCR primer

<400> SEQUENCE: 250
acgtgtagca ctgcttgttt t                                                  21
```